(12) United States Patent
Williams et al.

(10) Patent No.: US 7,432,369 B2
(45) Date of Patent: Oct. 7, 2008

(54) PYRIDYL-SUBSTITUTED PORPHYRIN COMPOUNDS AND METHODS OF USE THEREOF

(75) Inventors: William Williams, Ipswich, MA (US); Garry Southan, Lynn, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 171 days.

(21) Appl. No.: 11/090,447

(22) Filed: Mar. 25, 2005

(65) Prior Publication Data

US 2006/0003982 A1   Jan. 5, 2006

Related U.S. Application Data

(60) Provisional application No. 60/628,465, filed on Nov. 16, 2004, provisional application No. 60/557,551, filed on Mar. 29, 2004.

(51) Int. Cl.
*C07B 47/00* (2006.01)
*C07D 487/22* (2006.01)

(52) U.S. Cl. .................................................. 540/145
(58) Field of Classification Search ................ 540/145; 514/185, 410
See application file for complete search history.

(56) References Cited

U.S. PATENT DOCUMENTS

| | | | |
|---|---|---|---|
| 4,822,899 | A | 4/1989 | Groves et al. |
| 5,223,538 | A | 6/1993 | Fridovich et al. |
| 5,227,405 | A | 7/1993 | Fridovich et al. |
| 5,650,137 | A | 7/1997 | Nguyen et al. |
| 5,723,677 | A | 3/1998 | Wijesekera et al. |
| 5,994,339 | A | 11/1999 | Crapo et al. |
| 6,002,026 | A | 12/1999 | Groves et al. |
| 6,013,241 | A | 1/2000 | Marchal et al. |

(Continued)

FOREIGN PATENT DOCUMENTS

AU   200054603 B2   12/2000

(Continued)

OTHER PUBLICATIONS

Batinic-Haberle I, Spasojevic I, Stevens RD, Hambright P, Neta P, Okado-Matsumoto A, Fridovich I. New class of potent catalysts of O2.-dismutation. Mn(III) ortho-methoxyethylpyridyl- and di-ortho methoxyethylimidazolylporphyrins. *Dalton Trans.* Jun. 7, 2004;(11):1696-702.

(Continued)

*Primary Examiner*—James O. Wilson
*Assistant Examiner*—Paul V. Ward
(74) *Attorney, Agent, or Firm*—Lahive & Cockfield, LLP; Jane E. Remillard, Esq.; Cynthia M. Soroos, Esq.

(57) ABSTRACT

The present invention relates to Pyridyl-Substituted Porphyrin Compounds, compositions comprising an effective amount of a Pyridyl-Substituted Porphyrin Compound and methods for treating or preventing injury due to exposure to a reactive species, erectile dysfunction due to surgery, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side effect of cancer chemotherapy, or a radiation-induced injury, or to prolong the half-life of an oxidation-prone compound, comprising administering to a subject in need thereof an effective amount of a Pyridyl-Substituted Porphyrin Compound.

19 Claims, 15 Drawing Sheets

U.S. PATENT DOCUMENTS

| | | | |
|---|---|---|---|
| 6,087,493 | A | 7/2000 | Wheelhouse et al. |
| 6,103,714 | A | 8/2000 | Fridovich et al. |
| 6,127,356 | A | 10/2000 | Crapo et al. |
| 6,194,566 | B1 | 2/2001 | Platzek et al. |
| 6,204,259 | B1 | 3/2001 | Riley et al. |
| 6,245,758 | B1 | 6/2001 | Stern et al. |
| 6,372,727 | B1 | 4/2002 | Crow et al. |
| 6,403,788 | B1 | 6/2002 | Meunier et al. |
| 6,448,239 | B1 | 9/2002 | Groves et al. |
| 6,479,477 | B1 | 11/2002 | Crapo et al. |
| 6,544,975 | B1 | 4/2003 | Crapo et al. |
| 6,573,258 | B2 | 6/2003 | Bommer et al. |
| 6,583,132 | B1 | 6/2003 | Crapo et al. |
| 6,730,666 | B1 | 5/2004 | Yayon et al. |
| 6,916,799 | B2 | 7/2005 | Fridovich et al. |
| 6,969,707 | B2 | 11/2005 | Groves et al. |
| 2002/0042407 | A1 | 4/2002 | Fridovich et al. |
| 2003/0055032 | A1 | 3/2003 | Groves et al. |
| 2003/0069281 | A1 | 4/2003 | Fridovich et al. |
| 2003/0086916 | A1 | 5/2003 | Goligorsky et al. |
| 2004/0019031 | A1 | 1/2004 | Crapo et al. |
| 2004/0023941 | A1 | 2/2004 | Crapo et al. |
| 2004/0039211 | A1 | 2/2004 | Fridovich et al. |
| 2004/0058902 | A1 | 3/2004 | Batinic-Haberle et al. |
| 2006/0199792 | A1 | 9/2006 | Groves et al. |
| 2007/0072825 | A1 | 3/2007 | Williams |

FOREIGN PATENT DOCUMENTS

| | | |
|---|---|---|
| CA | 2 373 336 | 12/2000 |
| DE | 19647640 A1 | 5/1998 |
| EP | 1 185 532 A0 | 12/2000 |
| JP | 03-038587 | 2/1991 |
| WO | WO 95/10185 A1 | 4/1995 |
| WO | WO 96/39409 A1 | 12/1996 |
| WO | WO-99/23097 | 5/1999 |
| WO | WO 99/55388 A1 | 11/1999 |
| WO | WO 00/43395 A1 | 7/2000 |
| WO | WO 00/75144 A2 | 12/2000 |
| WO | WO 02/100994 A1 | 12/2002 |
| WO | WO 03/078436 A1 | 9/2003 |
| WO | WO 2007/064795 A2 | 6/2007 |

OTHER PUBLICATIONS

Batinic-Haberle I, Spasojevic I, Fridovich I. Tetrahydrobiopterin rapidly reduces the SOD mimic Mn(III) ortho-tetrakis(N-ethylpyridinium-2-yl)porphyrin. *Free Radic Biol Med.* Aug. 1, 2004;37(3):367-74.

Batinic-Haberle I, Benov L, Spasojevic I, Fridovich I. The ortho effect makes manganese(III) meso-tetrakis(N-methylpyridinium-2-yl)porphyrin a powerful and potentially useful superoxide dismutase mimic. *J Biol Chem.* Sep. 18, 1998;273(38):24521-8.

Batinic-Haberle I, Liochev SI, Spasojevic I, Fridovich I. A potent superoxide dismutase mimic: manganese beta-octabromo-meso-tetrakis-(N-methylpyridinium-4-yl) porphyrin. *Arch Biochem Biophys.* Jul. 15, 1997;343(2):225-33.

Benov L, Batinic-Haberle I, Spasojevic I, Fridovich I. Isomeric N-alkylpyridylporphyrins and their Zn(II) complexes: inactive as SOD mimics but powerful photosensitizers. *Arch Biochem Biophys.* Jun. 15, 2002;402(2):159-65.

Benov L, Fridovich I. Superoxide dependence of the toxicity of short chain sugars. *J Biol Chem.* Oct. 2, 1998;273(40):25741-4.

Benov L, Fridovich I. The rate of adaptive mutagenesis in *Escherichia coli* is enhanced by oxygen(superoxide). *Mutat Res.* Oct. 25, 1996;357(1-2):231-6.

Benov L, Fridovich I. A superoxide dismutase mimic protects sodA sodB *Escherichia coli* against aerobic heating and stationary-phase death. *Arch Biochem Biophys.* Sep. 10, 1995;322(1):291-4.

Bowler RP, Arcaroli J, Abraham E, Patel M, Chang LY, Crapo JD. Evidence for extracellular superoxide dismutase as a mediator of hemorrhage-induced lung injury. *Am J Physiol Lung Cell Mol Physiol.* Apr. 2003;284(4):L680-7.

Bowler RP, Sheng H, Enghild JJ, Pearlstein RD, Warner DS, Crapo JD. A catalytic antioxidant (AEOL 10150) attenuates expression of inflammatory genes in stroke. *Free Radic Biol Med.* Oct. 15, 2002;33(8):1141-52.

Camhi et al., Induction of Heme Oxygenase-1 Gene Expression by Lipopolysaccharide Is Mediated by AP-1 Activation, *Am. J. Respir. Cell Mol. Biol..*, vol. 13, No. 4, 10 1995, 387-398.

Chang LY, Crapo JD. Inhibition of airway inflammation and hyperreactivity by a catalytic antioxidant. *Chest.* Mar. 2003;123(3 Suppl):446S.

Chang LY, Subramaniam M, Yoder BA, Day BJ, Ellison MC, Sunday ME, Crapo JD. A catalytic antioxidant attenuates alveolar structural remodeling in bronchopulmonary dysplasia. *Am J Respir Crit Care Med.* Jan. 1, 2003;167(1):57-64.

Chang LY, Crapo JD. Inhibition of airway inflammation and hyperreactivity by an antioxidant mimetic. *Free Radic Biol Med.* Aug. 1, 2002;33(3):379-86.

Chaniotakis NA, Chasser AM, Meyerhoff ME, Groves JT. Influence of porphyrin structure on anion selectivities of manganese(III) porphyrin based membrane electrodes. *Anal Chem.* Jan. 15, 1988;60(2):185-8.

Cross et al., A Catalyst of Peroxynitrite Decomposition Inhibits Murine Experimental Autoimmune Encephalomyelitis, *Journal of Neuroimmunology* 107 (2000) 21-28.

Crow, Manganese and Iron Porphyrins Catalyze Peroxynitrite Decomposition and Simultaneously Increase Nitration and Oxidant Yield: Implications for Their Use as Peroxynitrite Scavengers in Vivo, *Archives of Biochemistry and Biophysics*, vol. 371, No. 1, pp. 41-52, 1999.

Cuzzocrea et al., Antioxidant Therapy: A New Pharmacological Approach in Shock, Inflammation, and Ischemia/Reperfusion Injury, *Pharm. Rev.,* 53:135-159 (2001).

Cuzzocrea et al., Beneficial Effects of Peroxynitrite Decomposition Catalyst in a Rat Model of Splanchnic artery Occlusion and Reperfusion, *The FASEB Journal*, vol. 14, 2000, 1061-1072.

Dal Maso et al., Epidemiology of non-Hodgkin Lymphomas and Other Haemolymphopoietic Neoplasms in People With Aids, *Lancet Oncol* (2003) 4(2):110-9.

Day BJ, Batinic-Haberle I, Crapo JD. Metalloporphyrins are potent inhibitors of lipid peroxidation. *Free Radic Biol Med.* Mar. 1999;26(5-6):730-6.

Day BJ, Crapo JD. A metalloporphyrin superoxide dismutase mimetic protects against paraquat-induced lung injury in vivo. *Toxicol Appl Pharmacol.* Sep. 1996;140(1):94-100.

Day BJ, Fridovich I, Crapo JD. Manganic porphyrins possess catalase activity and protect endothelial cells against hydrogen peroxide-mediated injury. *Arch Biochem Biophys.* Nov. 15, 1997;347(2):256-62.

Dirsch et al., Structural Requirements of Sesquiterpene Lactones to Inhibit LPS-Induced Nitric Oxide Synthesis in RAW 264.7 Macrophages, *Bioorganic & Medicinal Chemistry* 8 (2000) 2747-2753.

El-Serag, Hepatocellular Carcinoma, *J Clin Gastroenterol* (2002) 35(5 Suppl 2):S72-8.

Evgenov et al., Parenteral Administration of Glipizide Sodium Salt, An Inhibitor of Adenosine Triphosphate-Sensitive Potassium Channels, Prolongs Short-Term Survival After Severe Controlled Hemorrhage in Rats, *Crit Care Med.,* Oct. 2003;31(10):2429-36.

Faulkner KM, Liochev SI, Fridovich I. Stable Mn(III) porphyrins mimic superoxide dismutase in vitro and substitute for it in vivo. *J. Biol Chem.* Sep. 23, 1994;269(38):23471-6.

Ferdinandy et al, Peroxynitrite Is a Major Contributor to Cytokine-Induced Myocardical Contractile Failure, *Circulation Research* 241-247 (2000).

Ferrer-Sueta G, Vitturi D, Batinic-Haberle I, Fridovich I, Goldstein S, Czapski G, Radi R. Reactions of manganese porphyrins with peroxynitrite and carbonate radical anion. *J Biol Chem.* Jul. 25, 2003;278(30):27432-8.

Ferrer-Sueta G, Batinic-Haberle I, Spasojevic I, Fridovich I, Radi R. Catalytic scavenging of peroxynitrite by isomeric Mn(III) N-methylpyridylporphyrins in the presence of reductants. *Chem Res Toxicol.* May 1999;12(5):442-9.

Gauuan PJ, Trova MP, Gregor-Boros L, Bocckino SB, Crapo JD, Day BJ. Superoxide dismutase mimetics: synthesis and structure-activity relationship study of MnTBAP analogues. *Bioorg Med Chem.* Sep. 2002;3013-21.

Groves JT, Crowley SJ, Shalyaev KV. Paramagnetic 1H-NMR relaxation probes of stereoselectivity in metalloporphyrin catalyzed olefin epoxidation. *Chirality.* 1998;10(1-2):106-19.

Groves JT. Artificial enzymes. The importance of being selective. *Nature.* Sep. 25, 1997;389(6649):329-30.

Groves JT, Fish KM, Avaria-Neisser GE, Imachi M, Kuczkowski RL. A unique deuterium/proton exchange during cytochrome P-450 mediated expoxidation of propene and butene. *Prog Clin Biol Res.* 1988;274:509-24.

Groves JT. Biological strategies for the manipulation of dioxygen. The chemistry of cytochrome P-450. *Ann N Y Acad Sci.* 1986;471:100-107.

Hernandez-Avila et al., Human Papilloma Virus 16-18 Infection and Cervical Cancer in Mexico: A Case-Control Study, *Archives of Medical Research* (1997) 28:265-271.

Herrmann et al., Epstein-Barr Virus-Associated Carcinomas: Facts and Fiction, *J Pathol* (2003) 199(2):140-5.

Howard et al., Intracerebral Drug Delivery in Rats With Lesion-Induced Memory Deficits, Intracerebral Drug Deliver *J. Neurosurg.* 71:105 (1989).

Hunt JA, Lee J, Groves JT. Amphiphilic peroxynitrite decomposition catalysts in liposomal assemblies. *Chem Biol.* Nov. 1997;4(11):845-58.

Imam et al., Methamphetamine Generates Peroxynitrite and Produces Dopaminergic Neurotoxicity in Mice: Protective Effects of Peroxynitrite Decomposition Catalyst, *Brain Research* 837 (1999) 15-21.

Imam et al., Methamphetamine-Induced Dopaminergic Neurotoxicity: Role of Peroxynitrite and Neuroprotective Role of Antioxidants and Peroxynitrite Decomposition Catalysts, *Annals New York Academy of Sciences,* 366-380.

Jiang et al., Tacrolimus and Cyclosporine Differ in Their Capacity to Overcome Ongoing Allograft Rejection as a Result of Their Differential Abilities to Inhibit Interleukin-10 Production, *Transplantation,* Jun. 15, 2002;73(11):1808-17.

Kachadourian et al., High-Performance Liquid Chromatography With Spectrophotometric and Electrochemical Detection of a Series of Manganese(III) Cationic Porphyrins, *Journal of Chromatography B,* 767 (2002) 61-67.

Kadow et al., The Role of Viruses in Human Cancer Development and Antiviral Approaches for Intervention, *Curr Opin Investig Drugs* (2002) 3(11):1574-9.

Kaufmann et al., Separation of the Rotational Isomers of Tetrakis(N-methyl-2-pyridiniumyl)Porphyrin and Crystal Structure of $\alpha,\alpha,\alpha,\beta$-(Tetrakis(N-methyl-2-pyridiniumyl)Porphyrin)Copper Xacyanoferrate, *Inorg. Chem.* 34: 5073-5079 (1995).

Komjati et al., Effects of FP15, a Potent Peroxynitrite Decomposition Catalyst in a Rat Model of Middle Cerebral Artery (MCA) Occlusion Induced Stroke, The FASEB Journal 16(4), A972, Abstract No. 713.4 (2002).

Lamping et al., LPS-Binding Protects Mice From Septic Shock Caused by LPS or Gram-Negative Bacteria, *J. Clin. Invest.* vol. 101, No. 10, May 1998, 2065-2071.

Lee et al., Mechanisms of Iron Porphyrin Reactions With Peroxynitrite, *J. Am. Chem. Soc.* 120:7493-7501 (1998).

Lee et al., Rapid Decomposition of Peroxynitrite by Manganese Porphyrin-Antioxidant Redox Couples, *Bioorg. Med. Chem. Letters* 7:2913-2918 (1997).

Lee et al., Manganese Porphyrins as Redox-Coupled Peroxynitrite Reductases, *J. Am. Chem. Soc.* 120:6053-6061 (1998).

Liaudet et al., The Novel and Potent Peroxynitrite Scavenger, FP 15, Protects Against Development of Colitis in Mice, The FASEB Journal 16(4), A599, Abstract No. 459.5 (2002).

Lindsey, *The Porphyrin Handbook,* Kadish, K.M. Smith, R. Guilard, Eds., vol. 1/Synthesis and Organic Chemistry, 45-118.

Liochev SI, Fridovich I. A cationic manganic porphyrin inhibits uptake of paraquat by *Escherichia coli. Arch Biochem Biophys.* Aug. 1, 1995;321(1):271-5.

Lubbers NL, Polakowski JS, Crapo JD, Wegner CD, Cox BF. Preischemic and postichemic administration of AEOL10113 reduces infarct size in a rat model of myocardial ischemia and reperfusion. *J Cardiovasc Pharmacol.* May 2003;41(5):714-9.

Mabley JG, Liaudet L, Pacher P, Southan GJ, Groves JT, Salzman AL, Szabo C., Part II. beneificial effects of the peroxynitrite decomposition catalyst FP15 in murine models of arthritis and colitis. *Mol Med.* Oct. 2002;8(10):581-90. Erratum in: Mol Med. Dec. 2002;8(12):885.

Mabley, J.G. et al., Part II: Beneficial Effects of the Peroxynitrite Decomposition Catalyst FP15 in Murine Models of Arthritis and Colitis, *Br J Pharmacol.,* Jul. 2001;133(6):909-19.

Mackensen GB, Patel M, Sheng H, Calvi CL, Batinic-Haberle I, Day BJ, LiangLP, Fridovich I, Crapo JD, Pearlstein RD, Warner DS. Neuroprotection from delayed postischemic administration of a metalloporphyrin catalytic antioxidant. *J Neurosci.* Jul. 1, 2001;21(13):4582-92.

Makino et al, Suppressive Effects of a New Anti-Inflammatory Agent, IS-741, on Dextran Sulfate Sodium-Induced Experimental Colitis in Rats, *Int'l Journal of Molecular Medicine* 9:391-396, 2002, pp. 391-396.

Melov S, Schneider JA, Day BJ, Hinerfeld D, Coskun P, Mirra SS, Crapo JD, Wallace DC. A novel neurological phenotype in mice lacking mitochondrial manganese superoxide dismutase. *Nat Genet.* Feb. 1998;18(2):159-63.

Misko et al., Characterization of the Cytoprotective Action of Peroxynitrite Decomposition Catalysts, *J. Biol. Chem.* 273:15646-15653 (1998).

Mortreux et al., Molecular and Cellular Aspects of HTLV-1 Associated Leukemogenesis In Vivo, *Leukemia* (2003) 17(1):26-38.

Naidu BV, Farivar AS, Woolley SM, Fraga C, Salzman AL, Szabo C, Groves JT, Mulligan MS. Enhanced peroxynitrite decomposition protects against experimental obliterative bronchiolitis. *Exp Mol Pathol.* Aug. 2003;75(1):12-7.

Okado-Matsumoto A, Batinic-Haberle I, Fridovich I. Complementation of SOD-deficient *Escherichia coli* by manganese porphyrin mimics of superoxide dismutase activity. *Free Radic Biol Med.* Aug. 1, 2004;37(3):401-10.

Oury TD, Thakker K, Menache M, Chang LY, Crapo JD, Day BJ. Attenuation of bleomycin-induced pulmonary fibrosis by a catalytic antioxidant metalloporphyrin. *Am J Respir Cell Mol Biol.* Aug. 2001;25(2):164-9.

Pacher P, Liaudet L, Bai P, Mabley JG, Kaminski PM, Virag L, Deb A, Szabo E, Ungvari Z, Wolin MS, Groves JT, Szabo C. Potent metalloporphyrin peroxynitrite decomposition catalyst protects against the development of doxorubicin-induced cardiac dysfunction. *Circulation.* Feb. 18, 2003;107(6):896-904.

Pacher et al., A Potent Peroxynitrite Decomposition Catalyst, FP 15, Protects Against the Development of Doxorubicin-Induced Heart Failure, The FASEB Journal 16(4), A177, Abstract No. 165.12 (2002).

Parrillo, Pathogenetic Mechanisms of Septic Shock, *The New England Journal of Medicine,* vol. 328:1471-1478, May 20, 1993, No. 20.

Patel M, Day BJ, Crapo JD, Fridovich I, McNamara JO. Requirement for superoxide in excitotoxic cell death. *Neuron.* Feb. 1996;16(2):345-55.

Penner-Hahn JE, McMurry TJ, Renner M, Latos-Grazynsky L, Eble KS, Davis IM,Balch AL, Groves JT, Dawson JH, Hodgson KO. X-ray absorption spectroscopic studies of high valent iron porphyrins. Horseradish peroxidase compounds I and II and synthetic models. *J Biol Chem.* Nov. 10, 1983;258(21):12761-4.

Perez et al., Antioxidant and Pro-Oxidant Effects of a Manganese Porphyrin Complex Against CYP2E1-Dependent Toxicity, *Free Radical Biology & Medicine,* vol. 33, No. 1, pp. 111-127, 2002.

Phillips-McNaughton K, Groves JT. Zinc-coordination oligomers of phenanthrolinylporphyrins. *Org Lett.* May 29, 2003;5(11):1829-32.

Piganelli JD, Flores SC, Cruz C, Koepp J, Batinic-Haberle I, Crapo J, Day B, Kachadourian R, Young R, Bradley B, Haskins K. A metalloporphyrin-based superoxide dismutase mimic inhibits adoptive transfer of autoimmune diabetes by a diabetogenic T-cell clone. *Diabetes.* Feb. 2002;51(2):347-55.

Robbins and Angell, Neoplasia and Other Disturbances of Cell Growth, *Basic Pathology*, 68-79 (2d ed. 1976).

Robbins and Angell, Neoplasia and Other Disturbances of Cell Growth *Basic Pathology*, 84-90 (2d ed. 1976).

Robbins and Angell, Clinical Aspects of Neoplasia, *Basic Pathology*, 112-113 (2d ed. 1976).

Ross AD, Sheng H, Warner DS, Piantadosi CA, Batinic-Haberle I, Day BJ, Crapo JD. Hemodynamic effects of metalloporphyrin catalytic antioxidants: structure-activity relationships and species specificity. *Free Radic Biol Med.* Dec. 15, 2002;33(12):1657-69.

Salvemini et al., Protective Effects of a Superoxide Dismutase Mimetic and Peroxynitrite Decomposition Catalysts in Endotoxin-Induced Intestinal Damage, British Journal of Pharmacology (1999) 127, 685-692.

Salvemini et al., Peroxynitrite Decomposition Catalysts: Therapeutics for Peroxynitrite-Mediated Pathology, Proc. Natl. Acad. Sci. USA, vol. 95, pp. 2659-2663, Mar. 1998.

Sanford MS, Groves JT. Anti-Markovnikov hydrofunctionalization of olefins mediated by rhodium-porphyrin complexes. *Angew Chem Int Ed Engl.* Feb. 1, 2004;43(5):588-90.

Sheng H, Enghild JJ, Bowler R, Patel M, Batinic-Haberle I, Calvi CL, Day BJ, Pearlstein RD, Crapo JD, Warner DS. Effects of metalloporphyrin catalytic antioxidants in experimental brain ischemia. *Free Radic Biol Med.* Oct. 1, 2002;33(7):947-61.

Shi et al., Quadruplex-Interactive Agents as Telomerase Inhibitors: Synthesis of Porphyrins and Structure-Activity Relationship for the Inhibition of Telomerase, *J. Med. Chem.* 44:4509-4523 (2002).

Shimanovich R, Hannah S, Lynch V, Gerasimchuk N, Mody TD, Magda D, Sessler J, Groves JT. Mn(II)-texaphyrin as a catalyst for the decomposition of peroxynitrite. *J Am Chem Soc.* Apr. 18, 2001;123(15):3613-4.

Shimanovich R, Groves JT. Mechanisms of peroxynitrite decomposition catalyzed by FeTMPS, a bioactive sulfonated iron porphyrin. *Arch Biochem Biophys.* Mar. 15, 2001;387(2):307-17.

Smith KR, Uyeminami DL, Kodavanti UP, Crapo JD, Chang LY, Pinkerton KE. Inhibition of tobacco smoke-induced lung inflammation by a catalytic antioxidant. *Free Radic Biol Med.* Oct. 15, 2002;33(8):1106-14.

Song et al., Synthesis and Selective Tumor Targeting Properties of Water Soluble Porphyrin-Pt(II) Conjugates, *Journal of Inorganic Biochemistry* 83 (2002) 83-88.

Spasojevic et al., Nitrosylation of Manganese(II) Tetrakis(N-ethylpyridinium-2-yl)Porphyrin: A Simple and Sensitive Spectrophotometric Assay for Nitric Oxide, *Biology and Chemistry* 4(5):526-533 (2000).

Spasojevic I, Menzeleev R, White PS, Fridovich I. Rotational isomers of N-alkylpyridylporphyrins and their metal complexes. HPLC separation, (1)H NMR and X-ray structural characterization, electrochemistry, and catalysis of $O(2)(.-)$ disproportionation. *Inorg Chem.* Nov. 4, 2002;41(22):5874-81.

Spasojevic I, Batinic-Haberle I, Reboucas JS, Idemori YM, Fridovich I. Electrostatic contribution in the catalysis of $O_2^*$- dismutation by superoxide dismutase mimics. MnIIITE-2-PyP5+ versus MnIIIBr8T-2-PyP+. *J Biol Chem.* Feb. 28, 2003;278(9):6831-7.

Szabo C, Mabley JG, Moeller SM, Shimanovich R, Pacher P, Virag L, Sorino FG, Van Duzer JH, Williams W, Salzman AL, Groves JT. Part I: pathogenetic role of peroxynitrite in the development of diabetes and diabetic vascular complications: studies with FP15, a novel potent peroxynitrite decomposition catalyst. *Mol Med.* Oct. 2002;8(10):571-80.

Szabo et al., The Novel and Potent Peroxynitrite Scavenger, FP 15, Protects Against Development of Arthritis in Mice, The FASEB Journal 16(4), A327, Abstract No. 243.21 (2002).

Szabo et al., A Novel, Potent Peroxynitrite Decomposition Catalyst: In Vitro Cytoprotective Actions and Protection Against Diabetes Mellitus and Diabetic Cardiovascular Complications, The FASEB Journal 16(4), A1166, Abstract No. 873.5 (2002).

Trova MP, Gauuan PJ, Pechulis AD, Bubb SM, Bocckino SB, Crapo JD, Day BJ. Superoxide dismutase mimetics. Part 2: synthesis and structure-activity relationship of glyoxylate- and glyoxamide-derived metalloporphyriins. *Bioorg Med Chem.* Jul. 3, 2003;11(13):2695-707.

Ungashe SB, Groves JT. Porphyrins and metalloporphyrins in synthetic bilayer membranes. *Adv Inorg Biochem.* 1994;9:317-51.

Vujaskovic Z, Batinic-Haberle I, Rabbani ZN, Feng QF, Kang SK, Spasojevic I, Samulski TV, Fridovich I, Dewhirst MW, Anscher MS. A small molecular weight catalytic metalloporphyrin antioxidant with superoxidedismutase (SOD) mimetic properties protects lungs from radiation-induced injury. *Free Radic Biol Med.* Sep. 15, 2002;33(6):857-63.

Xiao et al., Poly(ADP-Ribose) Polymerase Contributes to the Development of Myocardial Infarction in Diabetic Rats and Regulates the Nuclear Translocation of Apoptosis-Inducing Factor, *J Pharmacol Exp Ther.*, Aug. 2004;310(2):498-504.

Xiao et al., Poly(ADP-Ribose) Polymerase Promotes Cardiac Remodeling, Contractile Failure, and Translocation of Apoptosis-Inducing Factor in a Murine Experimental Model of Aortic Banding and Heart Failure, *J Pharmacol Exp Ther.*, Mar. 2005;312(3):891-8.

Zhang et al., Attenuation of Neointima Formation Through the Inhibition of DNA Repair Enzyme PARP-1 in Balloon-Injured Rat Carotid Artery, *Am J Physiol Heart Circ Physiol.*, Aug. 2004;287(2):H659-66.

Zhang et al., Intranuclear Localization of Apoptosis-Inducing Factor (AIF) And Large Scale DNA Fragmentation After Traumatic Brain Injury in Rats and in Neuronal Cultures Exposed to Peroxynitrite, *Journal of Neurochemistry,* 2002, 82, 181-191.

Zhou H, Groves JT. Hemodextrin: a self-assembled cyclodextrin-porphyrin construct that binds dioxygen. *Biophys Chem.* Sep. 2003;105(2-3):639-48.

Zingarelli B, Day BJ, Crapo JD, Salzman AL, Szabo C. The potential role of peroxynitrite in the vascular contractile and cellular energetic failure in endotoxic shock. *Br J Pharmacol.* Jan. 1997;120(2):259-67.

English-language translation of JP 2003-501432 (published Jan. 14, 2003) obtained from Japanese Patent Office Patent and Utility Model Gazette DB. http://www4.ipdl.inpit.go.jp/Tokujitu/tjsogodbenk.ipdl Accessed Jul. 16, 2007.

FIG. 4

PYRIDYL-SUBSTITUTED PORPHYRIN COMPOUNDS AND METHODS OF USE THEREOF

This application claims the benefit of U.S. Provisional Application No. 60/557,551, filed Mar. 29, 2004 and U.S. Provisional Application No. 60/628,465, filed Nov. 16, 2004, which are incorporated by reference herein in their entirety.

1. FIELD OF THE INVENTION

The present invention relates to Pyridyl-Substituted Porphyrin Compounds, compositions comprising an effective amount of a Pyridyl-Substituted Porphyrin Compound and methods for treating or preventing injury due to exposure to a reactive species, erectile dysfunction due to surgery, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side effect of cancer chemotherapy, or a radiation-induced injury, or to prolong the half-life of an oxidation-prone compound, comprising administering to a subject in need thereof an effective amount of a Pyridyl-Substituted Porphyrin Compound.

2. BACKGROUND OF THE INVENTION

Oxidants are normal by-products of cell metabolism. However, reactive oxygen species such as superoxide ("$O_2^-$") and reactive intermediates formed from $O_2^-$ are known to damage biological targets. For example, J. Lee et al., *J. Am. Chem. Soc.* 120:7493-7501 (1998) discloses that reactive oxygen and nitrogen species play a role in the regulation and inhibition of mitochondrial respiration and apoptosis.

S. Cuzzocrea et al., Pharm. *Rev.*, 53:135-159 (2001) discloses that biologically relevant free-radicals derived from oxygen include $O_2^-$, perhydroxyl radical ("$HO_2^-$"), and nitric oxide ("NO"). One source of $O_2^-$ is a proinflammatory cytokine, which produces $O_2^-$ during reperfusion following ischemia. This reference discloses that reaction of NO with $O_2^-$ forms the reactive peroxynitrite ion ("ONOO$^-$") according to the reaction:

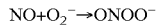

The reference further discloses that formation of ONOO— enhances the cytotoxic potential of NO and $O_2^-$.

In animals, a superoxide dismutase ("SOD") counters the effects of these reactive species. SODs are metalloenzymes that catalyze the conversion of $O_2^-$ to hydrogen peroxide and oxygen according to the reaction:

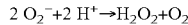

It is reported that certain synthetic metallomacrocyles also catalyze the transformation of reactive species into less reactive products. U.S. Pat. No. 6,204,259 to Riley et al. discloses that a pentazamacrocycle comprising a Mn(II) or Mn(III) metal can catalyze the conversion of $O_2^-$ into oxygen and hydrogen peroxide.

Spasojevic et al., *Biology and Chemistry* 4(5):526-533 (2000) discloses that tetrakis-5,10,15,20-(2-N-ethylpyridinium)porphyrinato complexes of manganese(II) and manganese(III) are catalytic scavengers of oxygen.

J. Lee et al., *J. Am. Chem. Soc.* 120:7493-7501 (1998) discloses that $O_2^-$ and ONOO$^-$ are decomposed by the metalloporphyrin 5,10,15,20-tetrakis(N-methyl-4-pyridyl)porphinatoiron(III).

Lee et al., *Bioorg. Med. Chem. Letters* 7:2913-2918 (1997) discloses that 5,10,15,20-tetrakis(N-methyl-4-pyridinium) porphinatomanganese(III) catalyzes the reduction of ONOO$^-$ in the presence of biological antioxidants such as vitamin C, gluthionate, and vitamin E.

U.S. Pat. No. 5,630,137 to Nguyen et al. discloses a cosmetic composition containing SODs in combination with metalloporphyrins that is allegedly useful to treat skin and hair disorders caused by free radicals. This patent discloses the use of naturally occurring metalloporphyrins such as chlorophyll, chlorophyllin and hemoglobin to allegedly reinforce the anti-free radical action of the SOD.

German Patent Publication No. DE 19647640 A1 discloses a metalloporphyrin dimer in which two metalloporphyrin compounds are covalently joined at the meso position of the porphyrin rings. The patent publication alleges that the dimer is useful for catalyzing oxygen-transfer processes.

International Publication No. WO 99/55388 discloses meso-substituted metalloporphyrin complexes in which the meso substituents are ester, alkyl, alkyl halide, and amide groups. This publication further alleges that such compounds are useful for modulating the cellular levels of oxidants and the processes in which these oxidants participate.

Metalloporphyrins are also reported to inhibit telomerase activity by binding to quadraplex DNA. For example, Shi et al., *J. Med. Chem.* 44:4509-4523 (2002) discloses that cationic forms of meso-tetrakis(N-methylpyridinium)metalloporphyrins interact with the quadraplex structure of DNA.

U.S. Pat. No. 6,087,493 to Wheelhouse et al. discloses meso-tetrakis(pyridyl)metalloporphyrins in which the nitrogen atom of the pyridyl rings are substituted with hydrogen, alkyl, alkylhydroxy, alkylamine, alkylacetate or alkylsulfate groups. This patent alleges that such compounds are useful as telomerase inhibitors.

U.S. Pat. No. 6,204,259 to Riley et al. discloses that pentazamacrocycles comprising a Mn(II) or Mn(III) metal are allegedly useful for treating inflammatory disease states and reperfusion injury.

U.S. Pat. No. 6,127,356 to Crapo et al. discloses meso-substituted metalloporphyrins in which the meso substituents are aryl, substituted aryl, cycloalkyl, 4-pyridyl or N-substituted 4-pyridyl groups. This patent further discloses meso-tetrakis(pyridinium)metalloporphyrins in which the nitrogen atom of the pyridyl ring is substituted with an alkyl group, alkylhydroxy, alkylamine, alkylcarboxylate, alkysulfate or alkylphospate. The patent alleges that the disclosed metalloporphyrins act as mimetics of SODs.

Misko et al., *J. Biol. Chem.* 273:15646-15653 (1998) discloses that 5,10,15,20-tetrakis(N-methyl-4-pyridinium)porphinatoiron(III) catalyzes the conversion of ONOO$^-$ into nitrate. The authors also disclose that 5,10,15,20-tetrakis(N-methyl-4-pyridinium) porphinatoiron(III) is allegedly useful for reducing cellular damage at sites of inflammation.

International Publication No. WO 00/75144 A2 discloses 5,10,15,20-tetrakis(N-alkylpyridinum)metalloporphyrins in which the pyridyl fragments are joined to the meso carbon atoms of the porphyrin ring at the 2("ortho"), 3("meta") or 4("para") position of the pyridyl ring relative to the nitrogen atom. The publication alleges that the meso-tetrakis(N-alkylpyridinium)metalloporphyrins are useful for treating inflammation diseases including arthritis, inflammatory bowel disease and acute respiratory disease syndrome, and for the treatment of ischemia-reperfusion injury.

U.S. Pat. No. 5,994,339 to Crapo et al. discloses Mn—, Fe— and Cu-based 5,10,15,20-tetrakis(N-alkyl-4-pyridinium)metalloporphyrins in which the nitrogen atom of the pyridyl ring is substituted with an alkyl, alkylhydroxy, alkylamine, alkylcarboxylate, alkylsulfate or alkyphosphate group. This patent also alleges that 5,10,15,20-tetrakis(N-alkyl-4-pyridinium)metalloporphyrins are useful as mimetics of SODs and for the treatment of an inflammatory condition.

U.S. Pat. No. 6,245,758 B1 to Stern et al. discloses the use of 5,10,15,20-tetrakis(pyridyl)metalloporphyrins, and their corresponding N-alkylpyridinium salts, to allegedly treat disorders including inflammation disease and ischemic reperfusion. Metals allegedly useful in the metalloporphyrins include Mn, Fe, Ni and V.

U.S. patent application Publication 2002/0042407 to Fridovich et al. discloses that 5,10,15,20-tetrakis(N-alkylpyridinium)metalloporphyrins are allegedly useful for modulating the intra-or extracellular levels of oxidants such as $O_2^-$. Metals allegedly useful in the metalloporphyrins include Fe, Mn, Co, Ni and Zn. The publication also discloses methods for using these 5,10,15,20-tetrakis(N-alkylpyridinium)metalloporphyrins to allegedly treat disorders such as inflammatory diseases of the skin and lungs, ischemia reperfusion injury; eye disorders such as glaucoma, macular degeneration and cataracts; and diseases of the central nervous system.

There remains, however, a clear need for compounds, compositions and methods for that are useful for treating or preventing injury due to exposure to a reactive species, erectile dysfunction due to surgery, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side-effect of cancer chemotherapy, or a radiation-induced injury, or to prolong the half-life of an oxidation-prone compound.

Citation of any reference in Section 2 of this application is not an admission that the reference is prior art to this application.

3. SUMMARY OF THE INVENTION

The present invention encompasses compounds having the Formula (A):

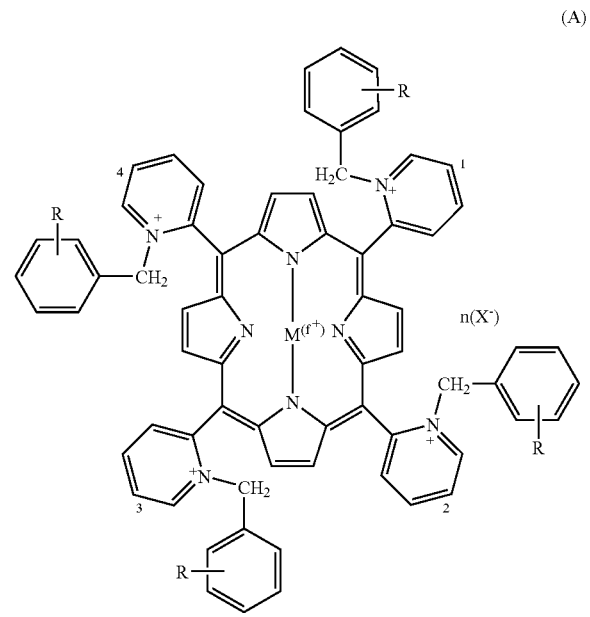

(A)

wherein:
M is Fe or Mn;
f is 0 or 1;
each R is independently —C(O)OH or —C(O)O$^-$;
each X$^-$ is independently a negatively-charged counterion; and
n=(f)+(the total number of R groups where R is —C(O)OH).

A compound of Formula (A) (a "Pyridyl-Substituted Porphyrin Compound") is useful for treating or preventing injury due to exposure to a reactive species, erectile dysfunction due to surgery, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side effect of cancer chemotherapy, or a radiation-induced injury, or to prolong the half-life of an oxidation-prone compound, (each being a "Condition") in a subject.

The invention also relates to compositions comprising an effective amount of a Pyridyl-Substituted Porphyrin Compound, and a physiologically acceptable carrier or vehicle. The compositions are useful for treating or preventing a Condition in a subject.

The invention further relates to methods for treating or preventing a Condition, comprising administering to a subject in need thereof an effective amount of a Pyridyl-Substituted Porphyrin Compound.

The present invention may be understood more fully by reference to the following detailed description, figures, and illustrative examples, which are intended to exemplify non-limiting embodiments of the invention.

4. BRIEF DESCRIPTION OF THE FIGURES

FIG. 1 shows a survival curve for Balb/c mice that were pre-treated with Compound 3A, prior to exposure to 6 Gy of ionizing radiation. The x-axis represents days post-irradiation and the y-axis represents the ratio of surviving mice to the total number of irradiated mice. Line -■- represents mice (n=10) treated with Compound 3A, administered at a dose of 2 mg/kg, two hours prior to irradiation followed by administration of post-irradition doses of 2 mg/kg every 12 hours until death. Line -□- represents a non-treated control group of mice (n=10).

FIG. 2 shows a survival curve for Balb/c mice that were treated with Compound 3A, after being exposed to 6 Gy of ionizing radiation. The x-axis represents days post-irradition and the y-axis represents the ratio of surviving mice to the total number of irradiated mice. Line -■- represents mice (n=10) treated with Compound 3A, administered at a dose of 2 mg/kg, ten minutes post-irradiation, followed by repeated administration of 2 mg/kg doses every 12 hours until death. Line -□- represents a non-treated control group of mice (n=10).

FIG. 3 shows a survival curve for Balb/c mice that were treated with Compound 3A, after being exposed to 6 Gy of ionizing radiation. The x-axis represents days post-irradition and the y-axis represents the ratio of surviving mice to the total number of irradiated mice. Line -■- represents mice (n=10) treated with Compound 3A, administered at a dose of 10 mg/kg, ten minutes post-irradiation, followed by repeated administration of 10 mg/kg doses every 12 hours for a time period of 30 days. Line -□- represents a non-treated control group of mice (n=10).

FIG. 4 shows the effect of Compound 3 on mitochondrial respiration in human A549 and murine RAW cells exposed to hydrogen peroxide, peroxynitrite, superoxide generated from xanthine oxidase and hypoxanthine, or nitroxyl radical generated by Angeli's salt. The four right-hand most bar graphs represent cytotoxin plus μM of Compound 3.

Figure 8:
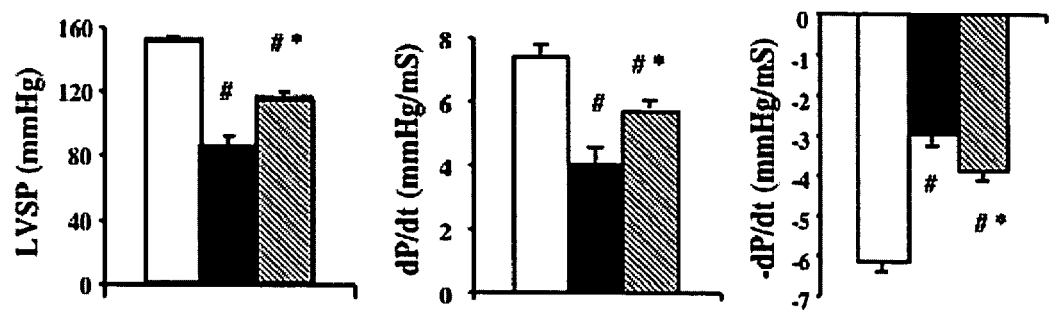

FIG. 8 shows cardiac function in vehicle treated and Compound 3 treated rats at 1 hour after resuscitation. The three bars in each graph represent, from left to right, sham, vehicle treated rats, and Compound 3 treated (6 mg/kg, i.v.) rats. Values are means±SEM. Sham (n=4), vehicle (n=8), Compound 3 (n=7); *, $P<0.05$ vs. vehicle treated rats; #, $P<0.05$ vs. rats.

Figure 9:
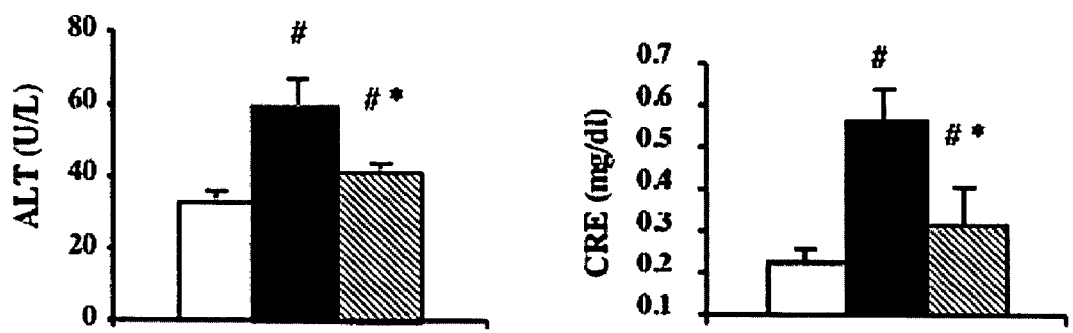

FIG. 9 shows plasma levels of alanine aminotransferase (ALT) and creatine (CRE) in vehicle treated and Compound 3 treated groups. The three bars in each graph represent, from left to right, sham, vehicle treated rats, and Compound 3 treated (6 mg/kg, i.v.) rats. Values are means±SEM. Sham (n=4), vehicle (n=8), Compound 3 (n=7); *, $P<0.05$ vs. vehicle treated rats; #, $P<0.05$ vs. sham rats.

Figure 10:
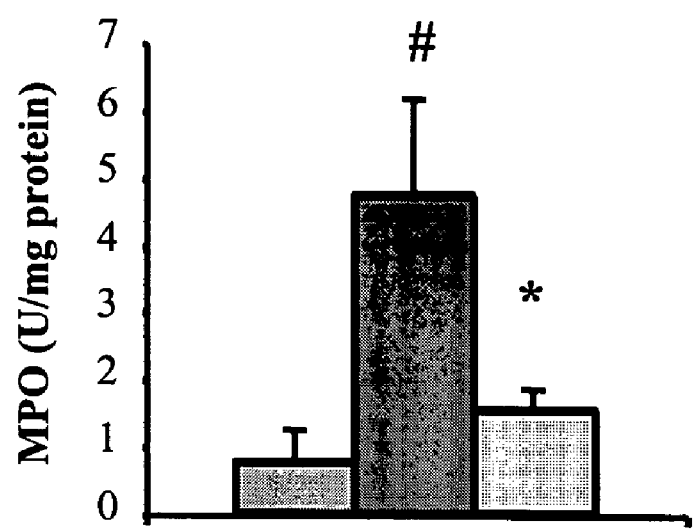

FIG. 10 shows pulmonary myeloperoxidase level (MPO) in sham animals in vehicle treated and Compound 3 treated hemorrhagic shock groups. The three bars in the graph represent, from left to right, sham, vehicle treated, and Compound 3 treated rats. Values are means±SEM. Sham (n=4), vehicle (n=8), Compound 3 (n=7); *, $P<0.05$ vs. vehicle treated rats; #, $P<0.05$ vs. sham rats.

Figure 11:
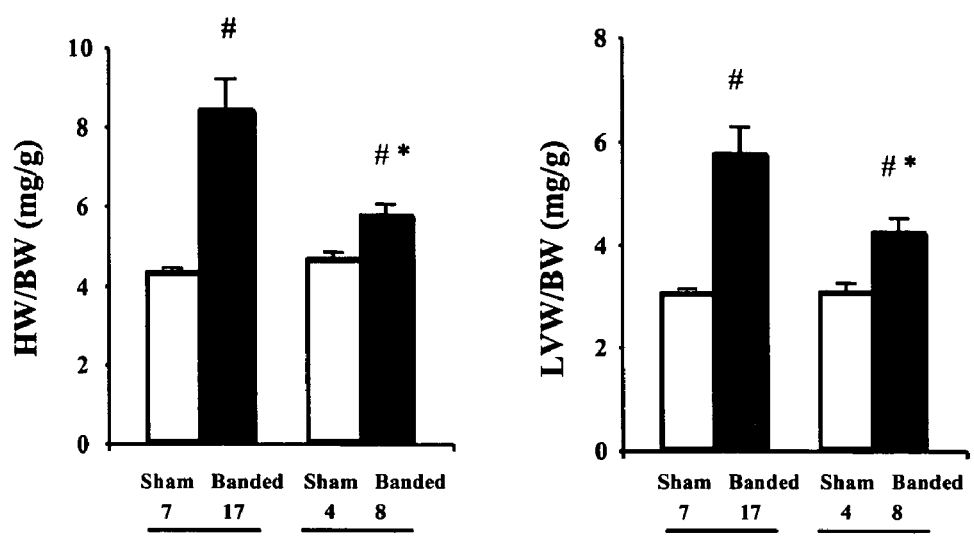

FIG. 11 shows cardiac hypertrophy (heart weight (HW)/body weight (BW) ratio, or left ventricular weight (LVW)/body weight (BW) ratio) in sham and banded animals with and without Compound 3 treatment for 2 months. The left-hand most set of bars in each graph represents vehicle treated and the right-hand most set of bars in each graph represents Compound 3 treated. Values are means±SEM. Sham (n=4), vehicle (n=8), Compound 3 (n=7); *, $P<0.05$ vs. vehicle treated rats; #, $P<0.05$ vs. sham rats.

Figure 12:
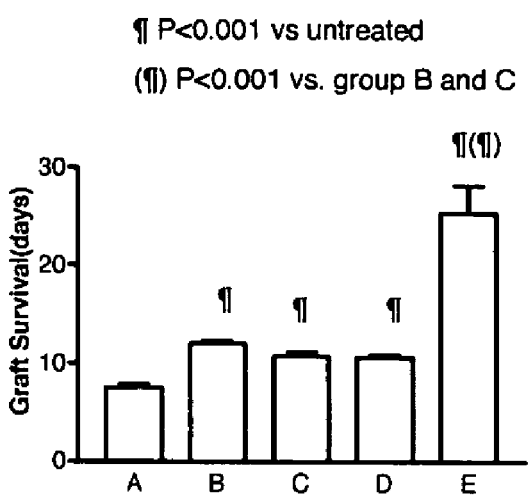

FIG. 12 shows the effect of Compound 3 at 0.3 mg/kg/day, i.p., and low-dose cyclosporine (2.5 mg/kg i.p.) on rat allografts. A: untreated, B: low-dose cyclosporine (2.5 mg/kg), C: Compound 3 at 0.3 mg/kg/day, D: Compound 3 at 1 mg/kg/day, E: Combination of Compound 3 at 0.3 mg/kg/day and cyclosporine at 2.5 mg/kg/day.

Figure 13:
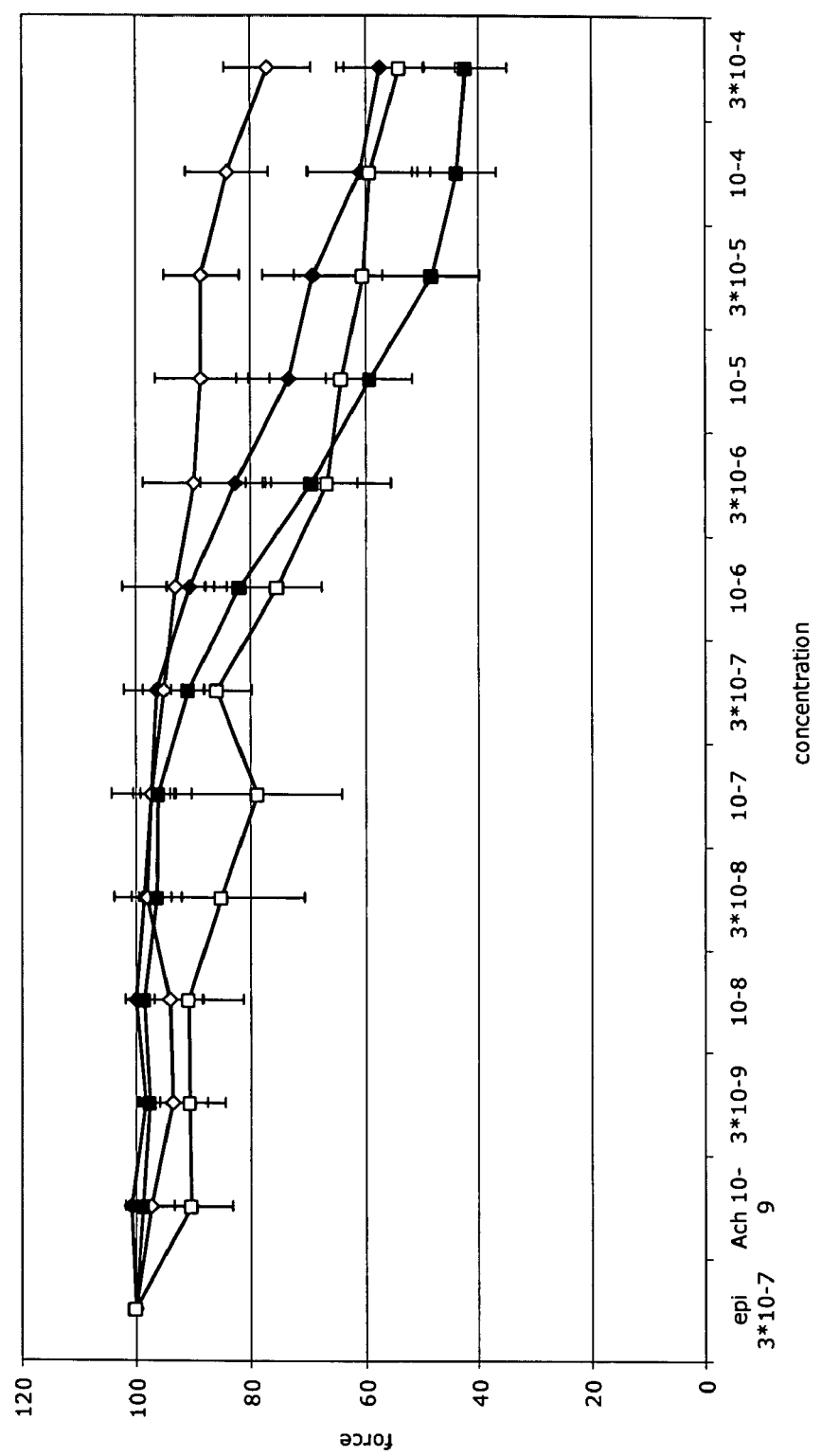

FIG. 13 shows the effect of Compound 3 at 1 mg/kg b.i.d., s.c., on a balloon-induced vascular injury in the rat. Line -♦- represents control right (control) side, n=6. Line -◇- represents control left (injured) side, n=5. Line -■- represents Compound 3 right (control) side, n=7.5. Line -□- represents Compound 3 left (injured) side, n=4.5.

Figure 14:
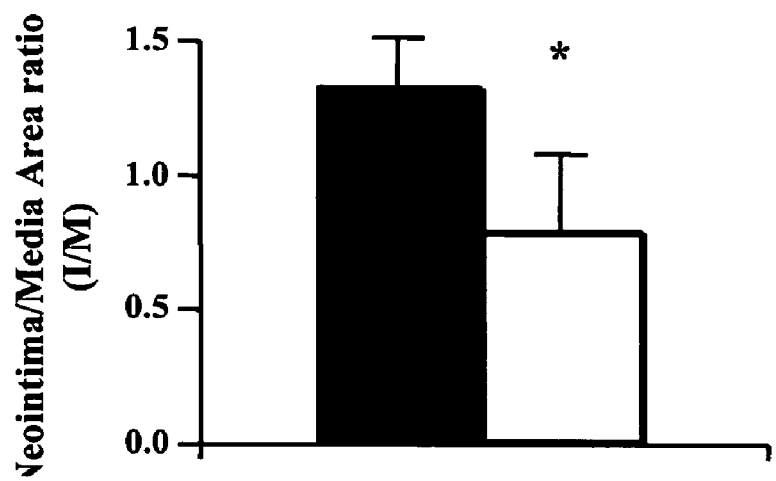

FIG. 14 shows the effect of Compound 3 at 1 mg/kg b.i.d., s.c., on balloon-induced vascular injury in the rat (n=4-7). The left bar indicates control and the right bar indicates Compound 3.

Figure 15:
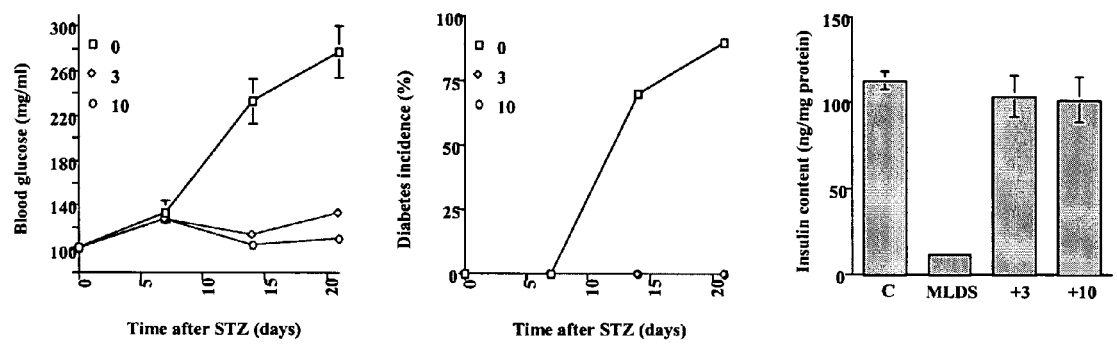

FIG. 15 shows the effect of Compound 3 (3 and 10 mg/kg/day i.p.) on streptozotocin (STZ)-induced hyperglycemia (left and middle panels) and loss of pancreatic insulin content (right panel), (n=20).

5. DETAILED DESCRIPTION OF THE INVENTION

5.1 Pyridyl-Substituted Porphyrin Compounds of Formula (A)

As stated above, the present invention encompasses Pyridyl-Substituted Porphyrin Compounds of Formula (A)

(A)

[Chemical structure of pyridyl-substituted porphyrin with central metal $M^{(f+)}$, four pyridyl groups labeled 1, 2, 3, 4 each bearing $CH_2$-phenyl-R substituents, and $n(X^-)$ counterion]

wherein M, f, R, $X^-$ and n are defined above.

In one embodiment M is Fe.

In another embodiment, M is Mn.

In one embodiment, f is 1.

In another embodiment, f is 0.

In one embodiment, $X^-$ is $Cl^-$ or $Br^-$.

In one embodiment, $X^-$ is $CH_3C(O)O^-$, 2-methylbenzoate, 3-methylbenzoate, or 4-methylbenzoate.

In one embodiment, an $X^-$ forms a bond with M.

In one embodiment, an $X^-$ that forms a bond with M is the same as an $X^-$ that does not form a bond with M.

In one embodiment, an $X^-$ that forms a bond with M is different from an $X^-$ that does not form a bond with M.

In one embodiment, an $X^-$ that does not form a bond with M is different from another $X^-$ that does not form a bond with M.

In another embodiment, each $X^-$ is independently $F^-$, $Cl^-$, $Br^-$, $I^-$, $HO^-$, or $CH_3C(O)O^-$.

In one embodiment, each R is $—C(O)O^-$.

In another embodiment, each R is $—C(O)OH$.

In one embodiment, n is 0.

In one embodiment, n is 1.

In another embodiment, n is 5.

In one embodiment M is Fe, f is 1, and $X^-$ is $Cl^-$.

In another embodiment, M is Fe, f is 1, $X^-$ is $Cl^-$, and each occurrence of R is $—C(O)O^-$.

In one embodiment, each R is in the ortho position.

In one embodiment, each R is in the meta position.

In one embodiment, each R is in the para position.

In one embodiment, the total number of —C(O)OH R groups is 4.

In another embodiment, the total number of —C(O)OH R groups is 3.

In another embodiment, the total number of —C(O)OH R groups is 2.

In a further embodiment, the total number of —C(O)OH R groups is 1.

In another embodiment, the total number of —C(O)OH R groups is 0.

In one embodiment, the Pyridyl-Substituted Porphyrin Compounds of Formula (A) are in isolated and purified form.

The Pyridyl-Subsituted Porphyrin Compounds of Formula (A) contain four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the Pyridyl-Subsituted Porphyrin Compounds of Formula (A) can exist in one of the following isomeric forms, denoted as Isomer Nos. 1-8, as described in the table below, or a mixture thereof, with the pyridyl groups being numbered 1-4 as shown in Formula (A):

| Isomer No. | Pyridyl Group # | | | |
| --- | --- | --- | --- | --- |
| | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the $X^-$ that forms a bond with M exists above the plane of the porphyrin ring. In another embodiment, the $X^-$ that forms a bond with M exists below the plane of the porphyrin ring.

In one embodiment, a Pyridyl-Subsituted Porphyrin Compound of Formula (A) is substantially free of its corresponding other isomers.

In another embodiment, a Pyridyl-Subsituted Porphyrin Compound of Formula (A) exists as a mixture of two or more isomers.

5.1.1 Pyridyl-Substituted Porphyrin Compounds of Formula (I)

In one embodiment, the Pyridyl-Substituted Porphyrin Compounds have the Formula (I)

wherein M, f, R, $X^-$ and n are defined above for the Pyridyl-Substituted Porphyrin Compounds of Formula (A).

In one embodiment M is Fe.

In another embodiment, M is Mn.

In one embodiment, f is 1.

In another embodiment, f is 0.

In one embodiment, $X^-$ is $Cl^-$ or $Br^-$.

In one embodiment, $X^-$ is $CH_3C(O)O^-$ or 4-methylbenzoate.

In one embodiment, an $X^-$ forms a bond with M.

In one embodiment, an $X^-$ that forms a bond with M is the same as an $X^-$ that does not form a bond with M.

In one embodiment, an $X^-$ that forms a bond with M is different from an $X^-$ that does not form a bond with M.

In one embodiment, an $X^-$ that does not form a bond with M is different from another $X^-$ that does not form a bond with M.

In another embodiment, each $X^-$ is independently $F^-$, $Cl^-$, $Br^-$, $I^-$, $HO^-$, or $CH_3C(O)O^-$.

In one embodiment, each R is —C(O)O$^-$.

In another embodiment, each R is —C(O)OH.

In one embodiment, n is 0.

In one embodiment, n is 1.

In another embodiment, n is 5.

In one embodiment M is Fe, f is 1, and $X^-$ is $Cl^-$.

In another embodiment, M is Fe, f is 1, $X^-$ is $Cl^-$, and each occurrence of R is —C(O)O$^-$.

In one embodiment, the total number of —C(O)OH R groups is 4.

In another embodiment, the total number of —C(O)OH R groups is 3.

In another embodiment, the total number of —C(O)OH R groups is 2.

In a further embodiment, the total number of —C(O)OH R groups is 1.

In another embodiment, the total number of —C(O)OH R groups is 0.

In one embodiment, the Pyridyl-Substituted Porphyrin Compounds of Formula (I) are in isolated and purified form.

Illustrative examples of the compounds of Formula (I) are as set forth below:
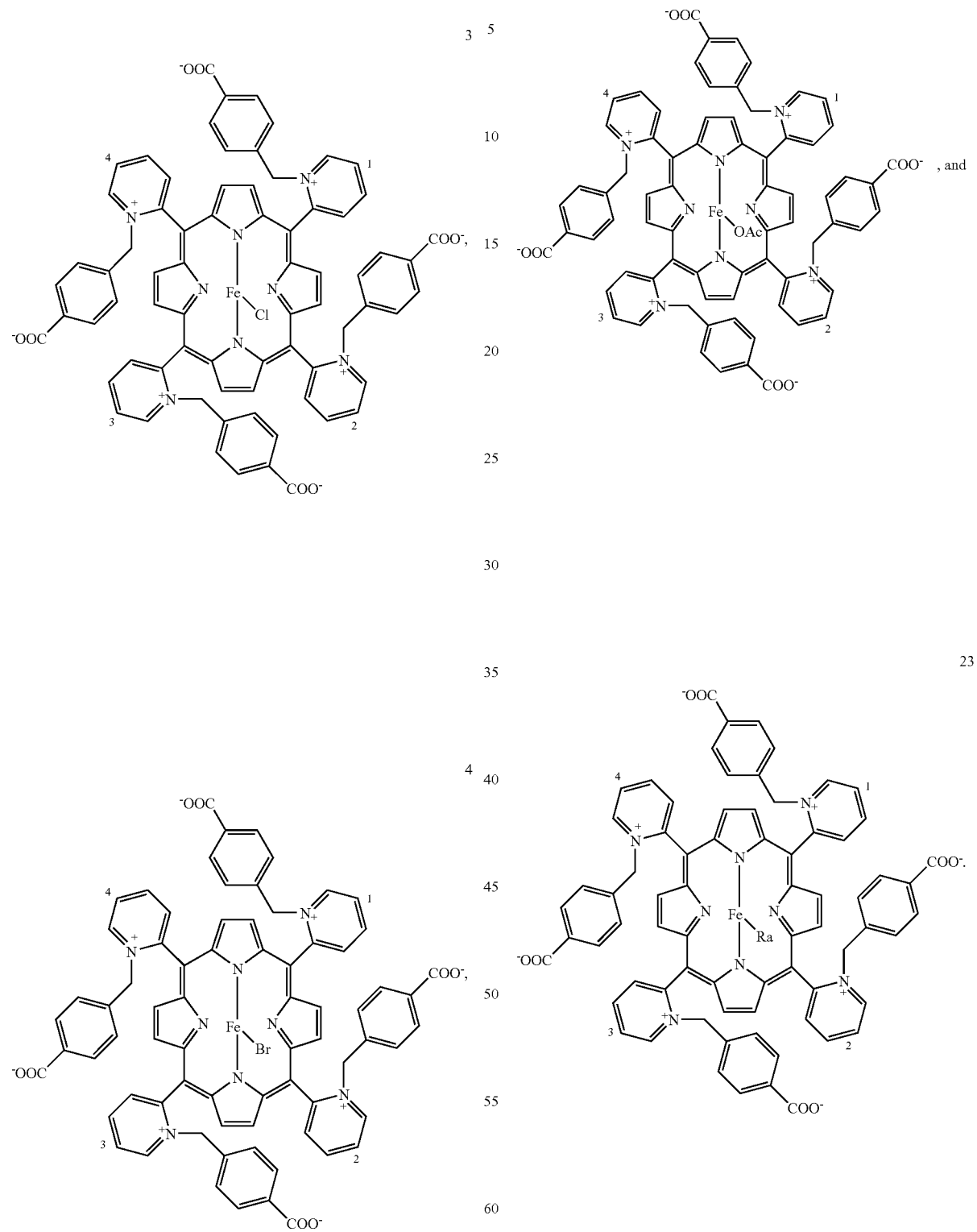
$R_a$ = 4-methylbenzoate
Additional illustrative examples of the compounds of Formula (I) are as set forth below:

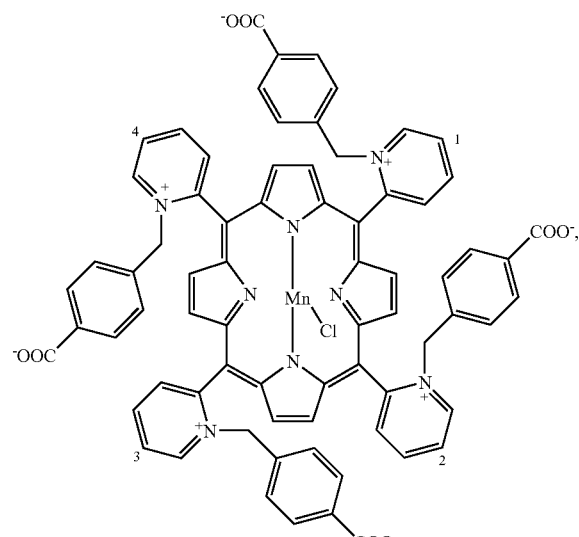

6

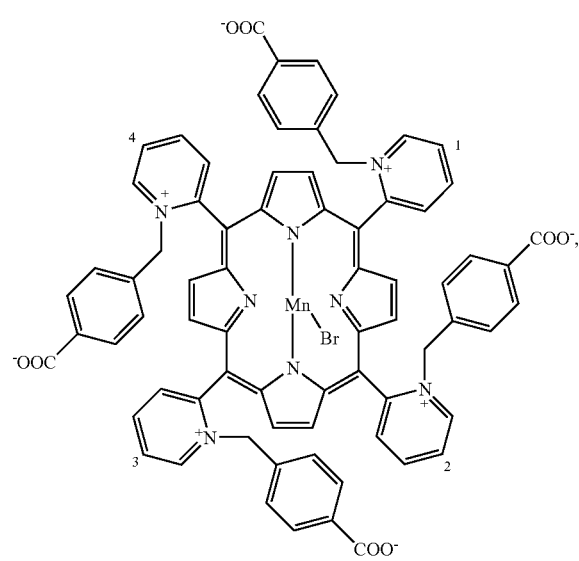

7

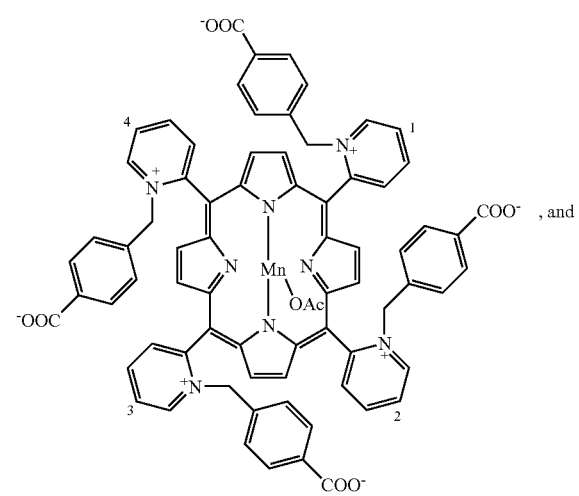

8

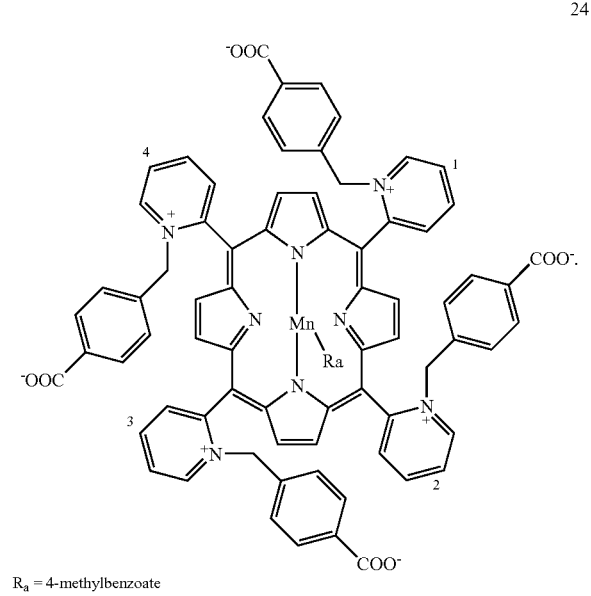

24

$R_a$ = 4-methylbenzoate

The Pyridyl-Subsituted Porphyrin Compounds of Formula (I) contain four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the Pyridyl-Subsituted Porphyrin Compounds of Formula (I) can exist in one of the following isomeric forms, denoted as Isomer Nos. 1-8, as described in the table below, or a mixture thereof, with the pyridyl groups being numbered 1-4 as shown in Formula (I):

| | Pyridyl Group # | | | |
|---|---|---|---|---|
| Isomer No. | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the X⁻ that forms a bond with M exists above the plane of the porphyrin ring. In another embodiment, the X⁻ that forms a bond with M exists below the plane of the porphyrin ring.

In one embodiment, a Pyridyl-Subsituted Porphyrin Compound of Formula (I) is substantially free of its corresponding other isomers.

In another embodiment, a Pyridyl-Subsituted Porphyrin Compound of Formula (I) exists as a mixture of two or more isomers.

5.1.2 Pyridyl-Substituted Porphyrin Compounds of Formula (II)

In one embodiment, the Pyridyl-Substituted Porphyrin Compounds have the Formula (II)

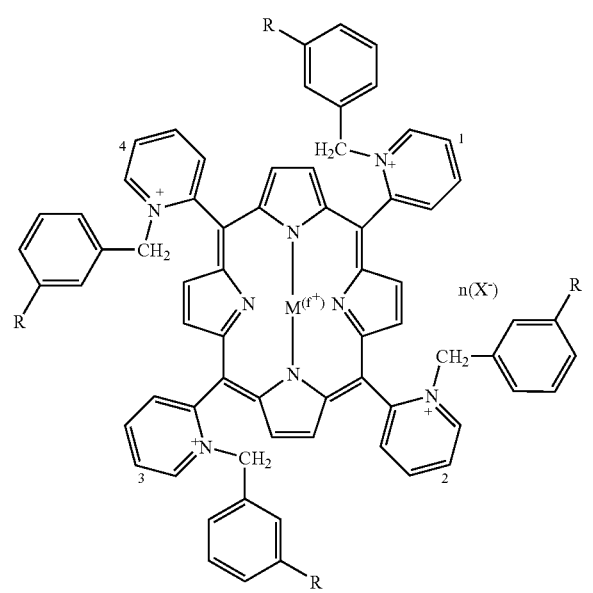

wherein M, f, R, $X^-$ and n are defined above for the Pyridyl-Substituted Porphyrin Compounds of Formula (A).

In one embodiment M is Fe.
In another embodiment, M is Mn.
In one embodiment, f is 1.
In another embodiment, f is 0.
In one embodiment, $X^-$ is $Cl^-$ or $Br^-$.
In one embodiment, $X^-$ is $CH_3C(O)O^-$ or 3-methylbenzoate.
In one embodiment, an $X^-$ forms a bond with M.
In one embodiment, an $X^-$ that forms a bond with M is the same as an $X^-$ that does not form a bond with M.
In one embodiment, an $X^-$ that forms a bond with M is different from an $X^-$ that does not form a bond with M.
In one embodiment, an $X^-$ that does not form a bond with M is different from another $X^-$ that does not form a bond with M.
In another embodiment, each $X^-$ is independently $F^-$, $Cl^-$, $Br^-$, $I^-$, $HO^-$, or $CH_3C(O)O^-$.
In one embodiment, each R is $-C(O)O^-$.
In another embodiment, each R is $-C(O)OH$.
In one embodiment, n is 0.
In one embodiment, n is 1.
In another embodiment, n is 5.
In one embodiment M is Fe, f is 1, and $X^-$ is $Cl^-$.
In another embodiment, M is Fe, f is 1, $X^-$ is $Cl^-$, and each occurrence of R is $-C(O)O^-$.

In one embodiment, the total number of $-C(O)OH$ R groups is 4.
In another embodiment, the total number of $-C(O)OH$ R groups is 3.
In another embodiment, the total number of $-C(O)OH$ R groups is 2.
In a further embodiment, the total number of $-C(O)OH$ R groups is 1.
In another embodiment, the total number of $-C(O)OH$ R groups is 0.

In one embodiment, the Pyridyl-Substituted Porphyrin Compounds of Formula (II) are in isolated and purified form.

Illustrative examples of the compounds of Formula (II) are as set forth below:

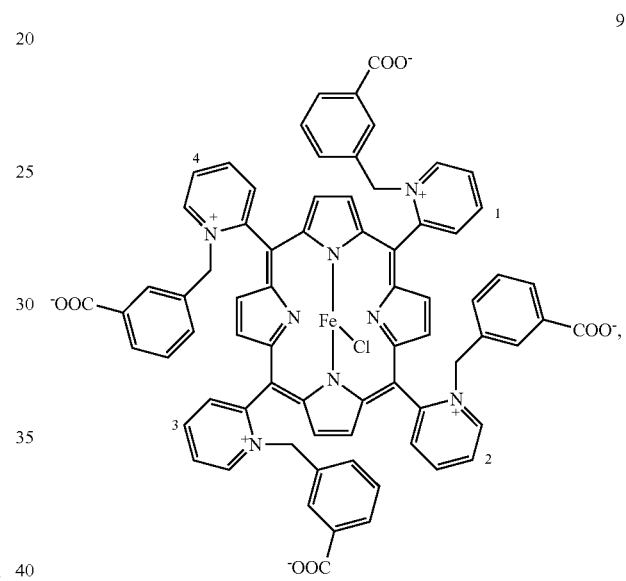

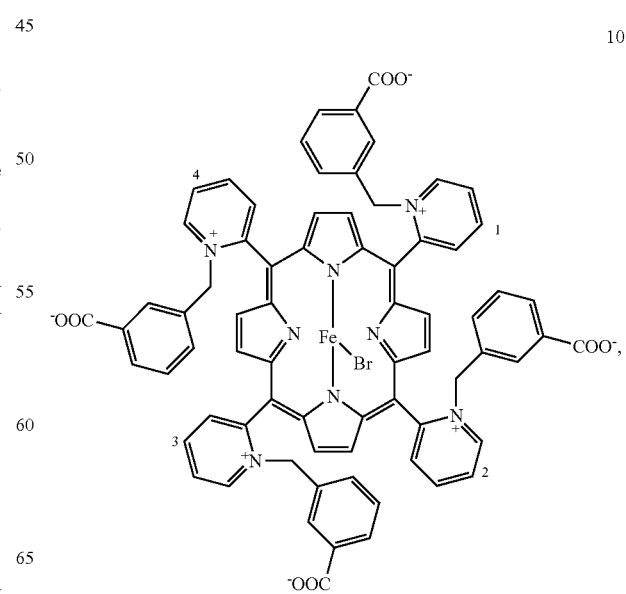

11
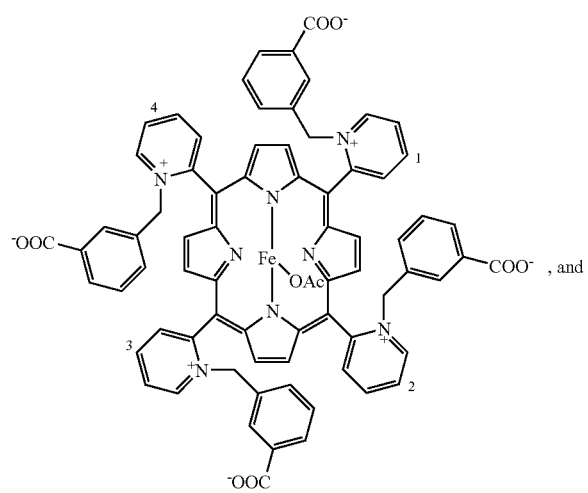
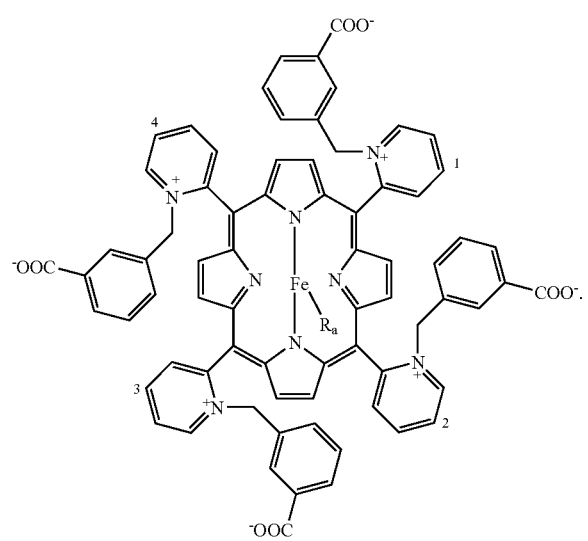
Ra = 3-methylbenzoate
Additional illustrative examples of the compounds of Formula (II) are as set forth below:
12
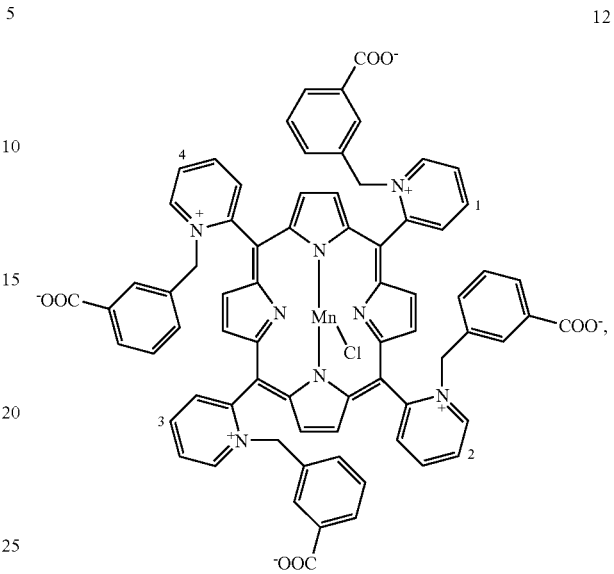
13
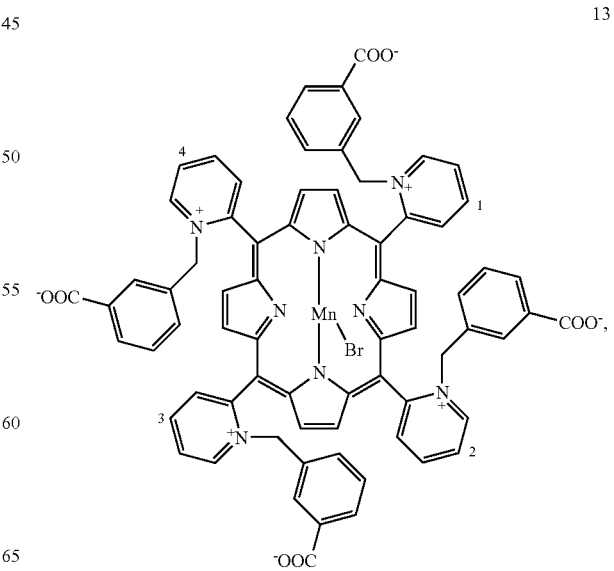

-continued

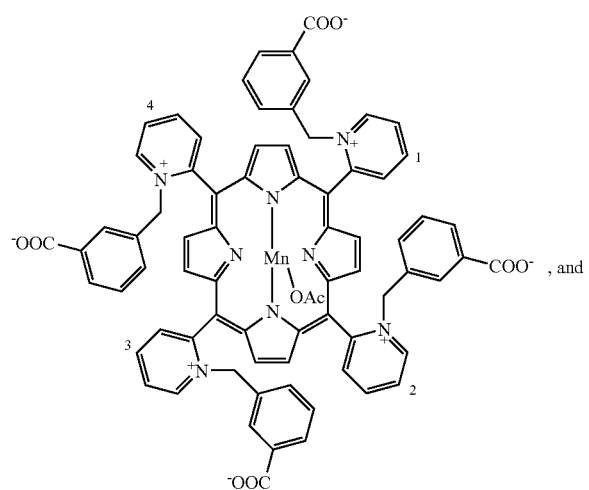

14

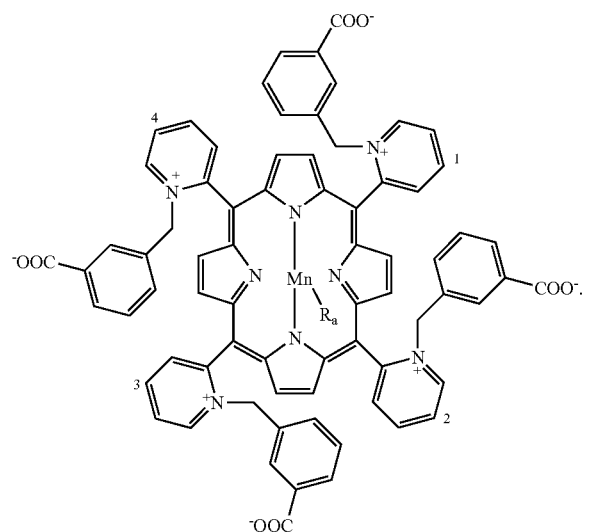

$R_a$ = 3-methylbenzoate

The Pyridyl-Subsituted Porphyrin Compounds of Formula (II) contain four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the Pyridyl-Subsituted Porphyrin Compounds of Formula (II) can exist in one of the following isomeric forms, denoted as Isomer Nos. 1-8, as described in the table below, or a mixture thereof, with the pyridyl groups being numbered 1-4 as shown in Formula (I):

| | Pyridyl Group # | | | |
| Isomer No. | 1 | 2 | 3 | 4 |
| --- | --- | --- | --- | --- |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the $X^-$ that forms a bond with M exists above the plane of the porphyrin ring. In another embodiment, $X^-$ that forms a bond with M exists below the plane of the porphyrin ring.

In one embodiment, a Pyridyl-Subsituted Porphyrin Compound of Formula (II) is substantially free of its corresponding other isomers.

In another embodiment, a Pyridyl-Subsituted Porphyrin Compound of Formula (II) exists as a mixture of two or more isomers.

5.1.3 Pyridyl-Substituted Porphyrin Compounds of Formula (III)

In one embodiment, the Pyridyl-Substituted Porphyrin Compounds have the Formula (III)

(III)

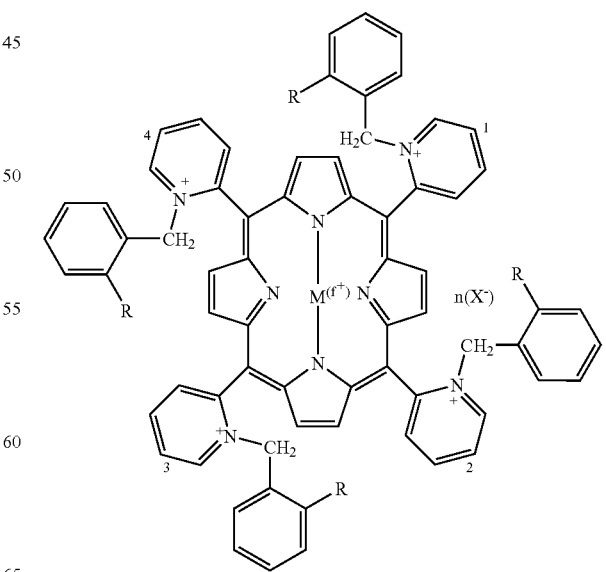

wherein M, f, R, X⁻ and n are defined above for the Pyridyl-Substituted Porphyrin Compounds of Formula (A).

In one embodiment M is Fe.

In another embodiment, M is Mn.

In one embodiment, f is 1.

In another embodiment, f is 0.

In one embodiment, X⁻ is Cl⁻ or Br⁻.

In one embodiment, X⁻ is $CH_3C(O)O^-$ or 2-methylbenzoate.

In one embodiment, an X⁻ forms a bond with M.

In one embodiment, an X⁻ that forms a bond with M is the same as an X⁻ that does not form a bond with M.

In one embodiment, an X⁻ that forms a bond with M is a different from an X⁻ that does not form a bond with M.

In one embodiment, an X⁻ that does not form a bond with M is different from another X⁻ that does not form a bond with M.

In another embodiment, each X⁻ is independently F⁻, Cl⁻, Br⁻, I⁻, HO⁻, or $CH_3C(O)O^-$.

In one embodiment, each R is —C(O)O⁻.

In another embodiment, each R is —C(O)OH.

In one embodiment, n is 0.

In one embodiment, n is 1.

In another embodiment, n is 5.

In one embodiment M is Fe, f is 1, and X⁻ is Cl⁻.

In another embodiment, M is Fe, f is 1, X⁻ is Cl⁻, and each occurrence of R is —C(O)O⁻.

In one embodiment, the total number of —C(O)OH R groups is 4.

In another embodiment, the total number of —C(O)OH R groups is 3.

In another embodiment, the total number of —C(O)OH R groups is 2.

In a further embodiment, the total number of —C(O)OH R groups is 1.

In another embodiment, the total number of —C(O)OH R groups is 0.

In one embodiment, the Pyridyl-Substituted Porphyrin Compounds of Formula (III) are in isolated and purified form.

Illustrative examples of the compounds of Formula (III) are as set forth below:

15

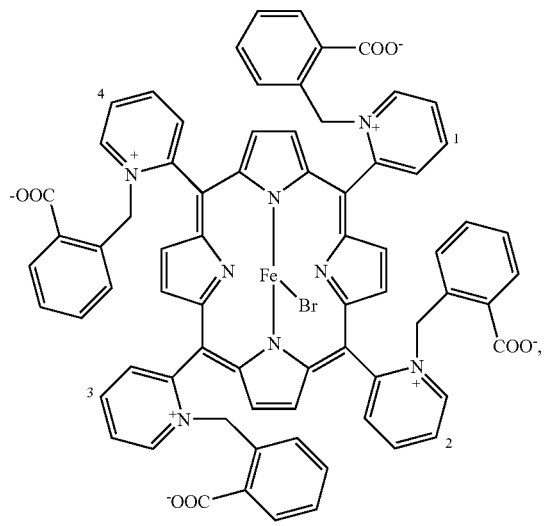

16

-continued

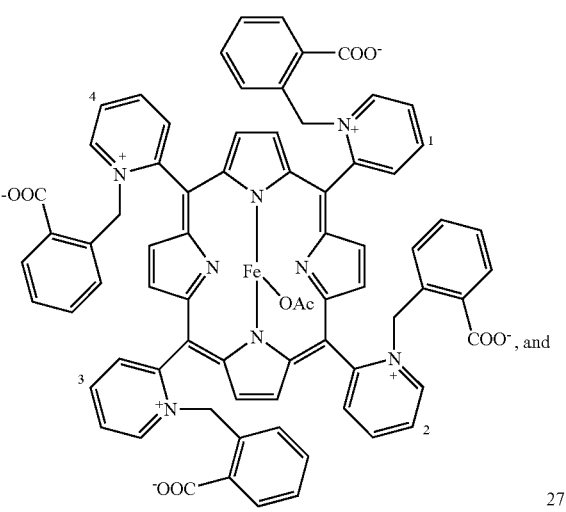

17

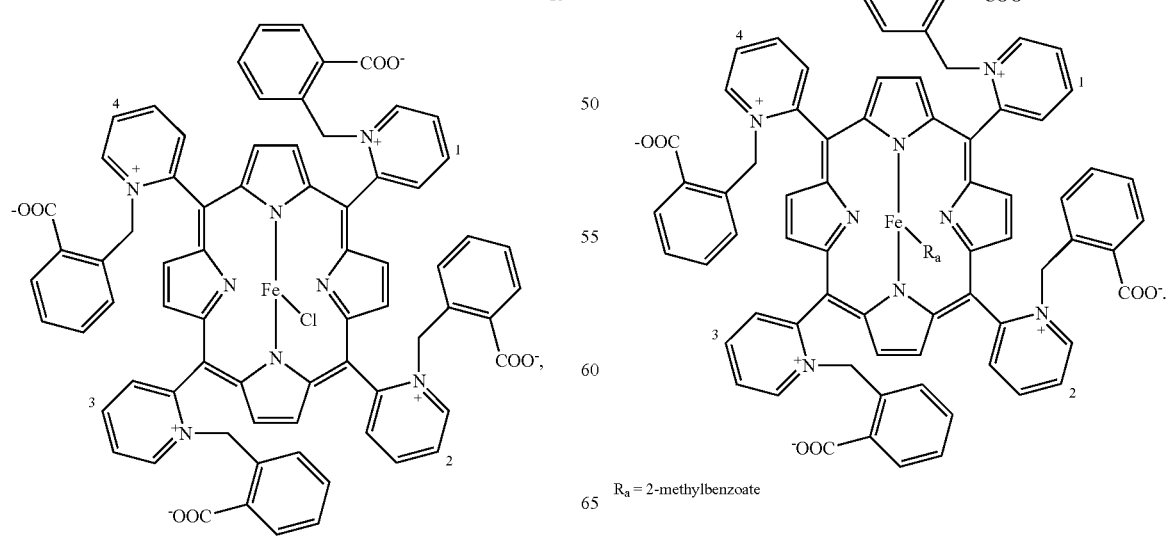

27

$R_a$ = 2-methylbenzoate

Additional illustrative examples of the compounds of Formula (III) are as set forth below:

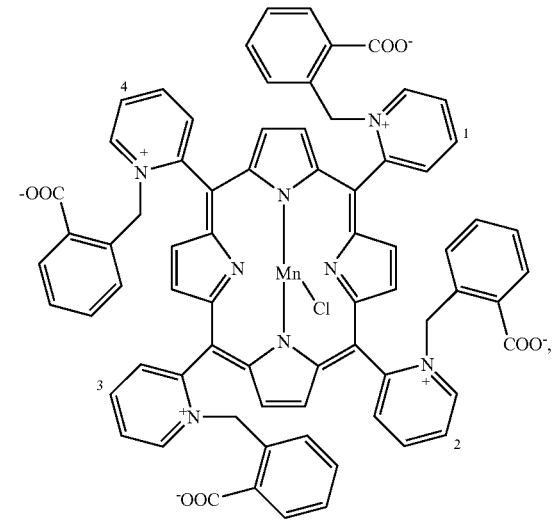

18

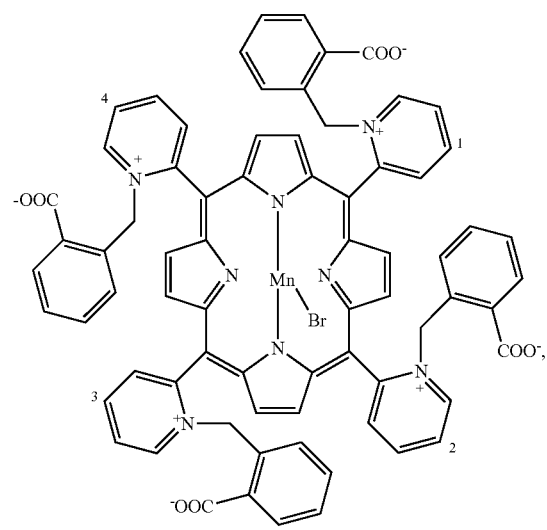

19

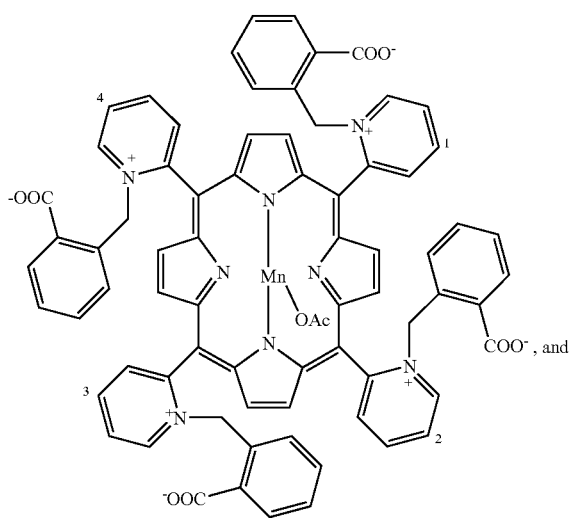

20

-continued

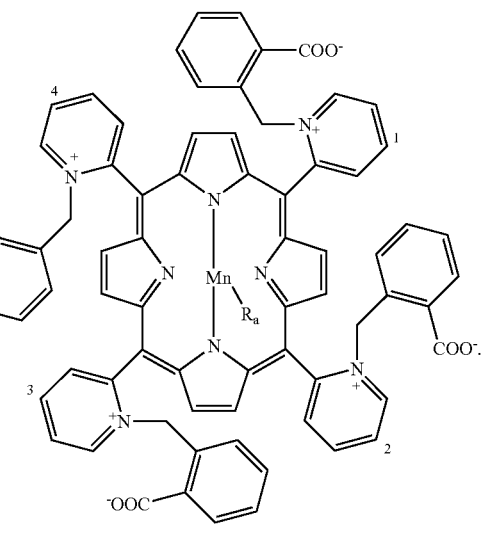

$R_a$ = 2-methylbenzoate

The Pyridyl-Subsituted Porphyrin Compounds of Formula (III) contain four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the Pyridyl-Subsituted Porphyrin Compounds of Formula (I) can exist in one of the following isomeric forms, denoted as Isomer Nos. 1-8, as described in the table below, or a mixture thereof, with the pyridyl groups being numbered 1-4 as shown in Formula (III):

| Isomer No. | Pyridyl Group # | | | |
| --- | --- | --- | --- | --- |
| | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the α-position.

In one embodiment, the X⁻ that forms a bond with M exists above the plane of the porphyrin ring. In another embodiment, the X⁻ that forms a bond with M exists below the plane of the porphyrin ring.

In one embodiment, a Pyridyl-Subsituted Porphyrin Compound of Formula (III) is substantially free of its corresponding other isomers.

In another embodiment, a Pyridyl-Subsituted Porphyrin Compound of Formula (III) exists as a mixture of two or more isomers.

5.2 Definitions

As used above and below have the following meaning:

The term "subject," as used herein, includes, but is not limited to, a cow, monkey, horse, sheep, pig, chicken, turkey, quail, cat, dog, mouse, rat, rabbit, guinea pig and human. In one embodiment, a subject is a human.

Illustrative counterions include but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, pamoate (i.e., 1,1'-methylene-bis-(2-hydroxy-3-naphthoate)), camphorsulfonate, 2-methylbenzoate, 3-methylbenzoate, and 4-methylbenzoate counterions.

The term "effective amount" when used in connection with a Pyridyl-Substituted Porphyrin Compound is an amount that is effective to treat or prevent a Condition in a subject.

The term "isolated and purified" as used herein means separated from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Pyridyl-Substituted Porphyrin Compound by weight of the isolate. In one embodiment, the isolate contains at least 95% of a Pyridyl-Substituted Porphyrin Compound by weight of the isolate.

The term "is substantially free of its corresponding other isomers" as used herein means no more than about 10% by weight of its corresponding other isomers; in one embodiment, no more than about 5% by weight, in another embodiment, no more than about 2% by weight, in another embodiment, no more than about 1% by weight, and in another embodiment, no more than about 0.1% by weight of its corresponding other isomers.

The term "reactive species" as used herein means a species that can injure a cell or tissue. Exemplary reactive species include oxidants and free radicals. Further exemplary reactive species include a reactive oxygen species, such as superoxide or peroxide, and a reactive nitrogen species, such as $^-ONOO$, nitric oxide, $NO^-$, NOH, or ONO.

In the Pyridyl-Substituted Porphyrin Compounds it is to be understood that the number of R groups where each R is —C(O)OH is an integer ranging from 0 to 4. Accordingly, n is the sum of f and an integer ranging from 0 to 4. It is to be further understood that n=f when all four R groups are —C(O)O$^-$. Whether each R group is —C(O)O$^-$ or —C(O)OH can vary due to factors including pH.

5.3 Methods for Making the Pyridyl-Substituted Porphyrin Compounds

The Pyridyl-Substituted Porphyrin Compounds can be made using conventional organic synthesis or by the following illustrative methods shown in Schemes 1-4 below.

Scheme 1 below illustrates a procedure useful for synthesizing porphyrin intermediate 1, which is useful for making the Pyridyl-Substituted Porphyrin Compounds of Formula (I).

Scheme 1

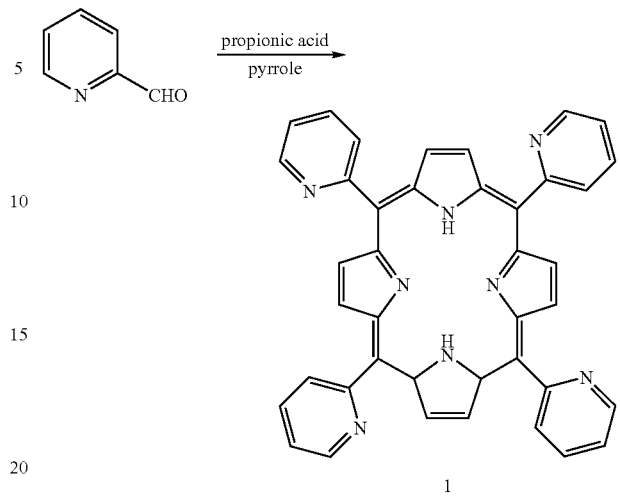

Pyridine-2-carboxaldehyde can be reacted with propionic acid and pyrrole in the presence of about 10% xylene or toluene at a temperature of from about 120° C. to reflux, for example at a temperature in the range of from about 130° C. to about 140° C., to provide the pyridyl porphyrin 1, which is useful for making the Pyridyl-Substituted Porphyrin Compounds of Formula (A).

Scheme 2 below illustrates a method useful for making the hydroxymetallo-porphyrin intermediates of Formula (IV), which are useful for making the Pyridyl-Substituted Porphyrin Compounds of Formula (I) wherein f is 1 and M is defined above for the Pyridyl-Substituted Porphyrin Compounds of Formula (I).

Scheme 2

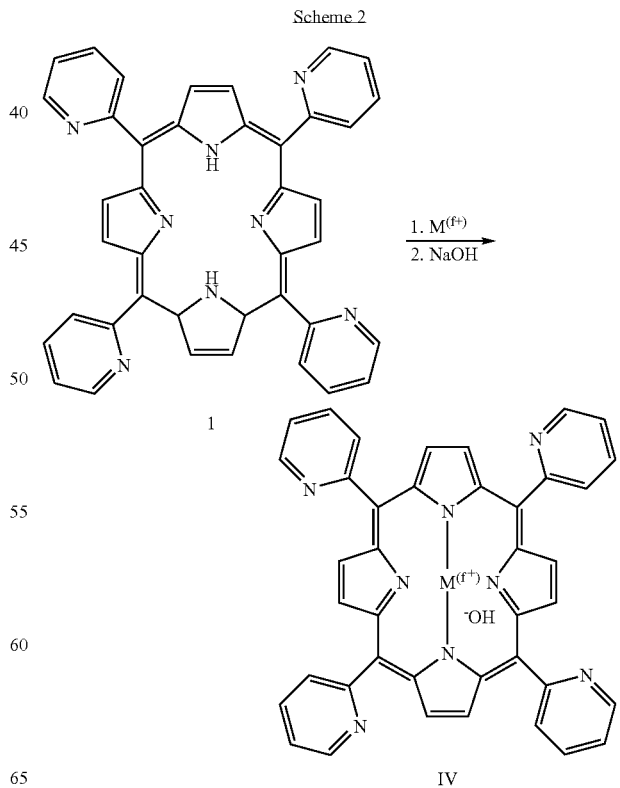

The porphyrin intermediate 1 can be reacted with a metallating agent in refluxing hydrochloric acid to form a metallated porphyrin complex that can be treated at room temperature with a hydroxide base, such as sodium hydroxide or potassium hydroxide, to provide the hydroxy-metallated porphyrin intermediates of Formula (IV). Metallating agents useful in the method of Scheme 2 include, but are not limited to, ferrous chloride, ferric chloride, ferric sulfate, ferrous acetate, ferrous ammonium sulfate, manganese(III) acetate, manganese(II) acetate, and manganese(II) chloride.

Scheme 3 below shows a method for making the Pyridyl-Substituted Porphyrin Compounds of Formula (A) wherein R is —COOH; n is 4 or 5; and M, f and $X^-$ are as defined above for the Pyridyl-Substituted Porphyrin Compounds of Formula (A).

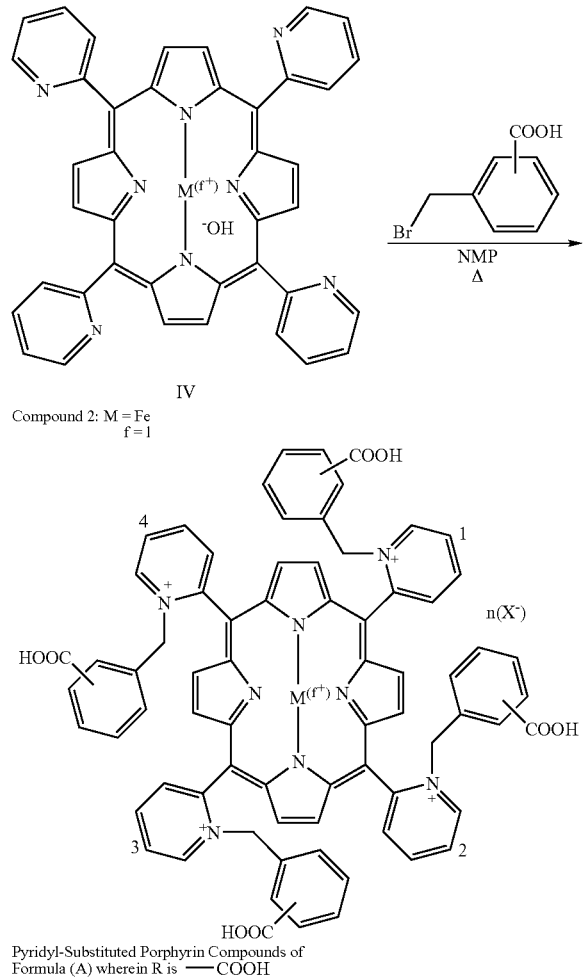

The pyridyl groups of the hydroxy-metallated porphyrin intermediates of Formula (IV) can be N-benzylated using excess α-bromo toluic acid in N-methylpyrrolidinone (NMP) at elevated temperature (about 50° C.-130° C.). This method provides Pyridyl-Substituted Porphyrin Compounds of Formula (A) wherein R=—COOH; n=f; $X^-$ is $Br^-$; and M, f, and n are as defined above for the Pyridyl-Substituted Porphyrin Compounds of Formula (A).

Scheme 4 below shows a method for ion exchange of a Pyridyl-Substituted Porphyrin Compound of Formula (A) having a $Br^-$ metal counterion. This method is useful for making Pyridyl-Substituted Porphyrin Compounds of Formula (A) wherein R is —COO$^-$; n=f; $X^-$ is other than $Br^-$; and M, f, and n are as defined above for the Pyridyl-Substituted Porphyrin Compounds of Formula (A).

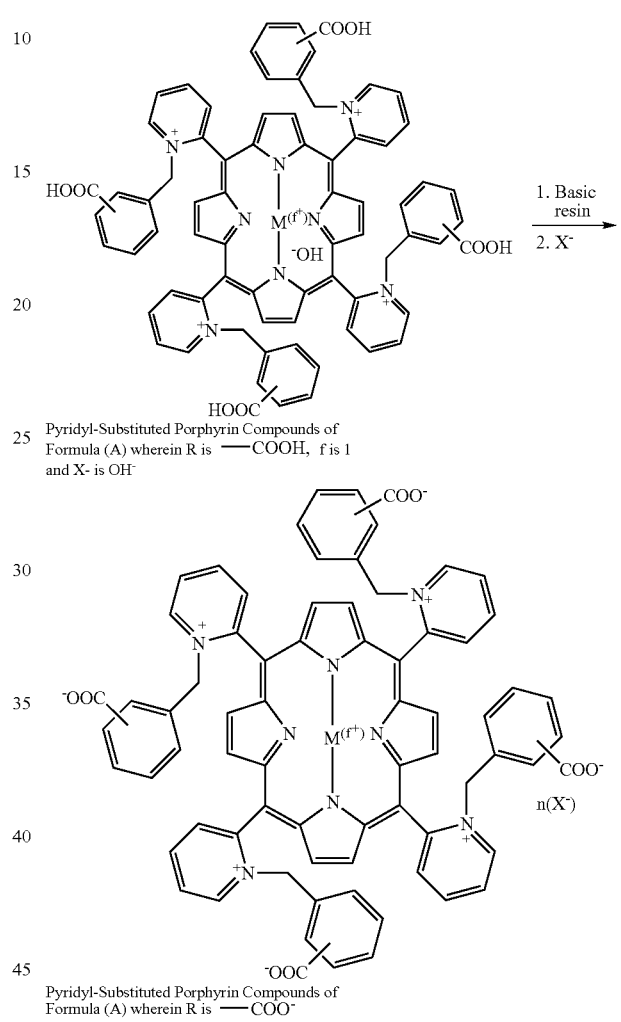

The Pyridyl-Substituted Porphyrin Compounds of Formula (A) wherein R is —COOH can be further derivatized by deprotonation of the carboxylic acid units using a basic resin (e.g., Dowex Marathon WBA-2 resin), followed by counterion exchange using a negative counterion source, including, but not limited to, an alkali metal halide; or a resin that can act as a source of a negative counterion, such as Amberlite IRA-402 chloride resin, to provide the Pyridyl-Substituted Porphyrin Compounds of Formula (A) wherein R is —COO$^-$ and $X^-$ is other than $Br^-$.

If desired, the Pyridyl-Substituted Porphyrin Compounds of Formula (A) can be purified using methods well-known to one of ordinary skill in the relevant art including, but not limited to, flash column chromatography, high-performance liquid chromatograpy (HPLC), medium-pressure liquid chromatography (MPLC), preparative thin-layer chromatograpy, anion-exchange chromatography, and recrystallization.

5.4 Therapeutic Uses of the Pyridyl-Substituted Porphyrin Compounds

In accordance with the invention, the Pyridyl-Substituted Porphyrin Compounds can be administered to a subject in need of treatment or prevention of a Condition.

In one embodiment, the Pyridyl-Substituted Porphyrin Compounds treat or prevent a Condition by scavenging or neutralizing one or more reactive species that are generated in vivo due to the interaction of ionizing radiation with a subject's tissue. Such reactive species include, but are not limited to, reactive oxygen species, including superoxides and peroxides; and reactive nitrogen species, including $^-ONOO$, nitric oxide, and nitroxyl species, such as $NO^-$, NOH, or ONO.

5.4.1 Treatment of Prevention of Injury Due to Exposure to a Reactive Species The Pyridyl-Substituted Porphyrin Compounds can be used to treat or prevent cell or tissue injury due to exposure to a reactive species. In one embodiment, the reactive species is an oxidant or a free radical, including, but not limited to reactive oxygen species, such as superoxides and peroxides, and reactive nitrogen species, such as $^-ONOO$, nitric oxide, and nitroxyl species, such as $NO^-$, NOH, and ONO.

Examples of injury due to exposure to a reactive species are skin wrinkling, skin aging, sunburn erythema, UV-induced skin injury, and UV-induced skin disease.

5.4.2 Prolonging the Half-Life of an Oxidation-Prone Compound

The Pyridyl-Substituted Porphyrin Compound can be used to prolong the half-life of an oxidation-prone compound in vivo. In another embodiment, a Pyridyl-Substituted Porphyrin Compound can be administered to a subject in combination with an oxidation-prone drug or biomaterial to treat or prevent oxidative injury due to, or biodegradation of, the oxidation-prone drug or biomaterial in vivo or in vitro. In one embodiment, the oxidation-prone drug or biomaterial is hyaluronic acid.

5.4.3 Treatment or Prevention of Erectile Dysfunction Due to Surgery

The Pyridyl-Substituted Porphyrin Compounds can be used to treat or prevent erectile dysfunction caused by surgery. In one embodiment, the surgery is surgery of the prostate or the colon.

5.4.4 Treatment or Prevention of Lung Disease

The Pyridyl-Substituted Porphyrin Compounds can be used to treat or prevent a lung disease. In one embodiment, the lung disease is cystic fibrosis, hyperoxic lung injury, emphysema, or adult respiratory distress syndrome.

5.4.5 Treatment or Prevention of Hyperoxia

The Pyridyl-Substituted Porphyrin Compounds can be used to treat or prevent injury due to hyperoxia. In one embodiment, the injury due to hyperoxia is hyperoxia-induced eye injury or hyperoxia-induced lung injury.

5.4.6 Treatment or Prevention of Neurodegenerative Disease

The Pyridyl-Substituted Porphyrin Compounds can be used to treat or prevent a neurodegenerative disease. In one embodiment, the neurodegenerative disease is Parkinson's disease, Alzheimer's disease, Huntington's disease, or amyotrophic lateral sclerosis.

5.4.7 Treatment or Prevention of Liver Disease

The Pyridyl-Substituted Porphyrin Compound can be used to treat or prevent a liver disease. In one embodiment, the liver disease is hepatitis, liver failure, or drug-induced liver injury.

5.4.8 Protecting a Subject's Heart Against Myocardial Damage During Cardioplegia In one embodiment, the invention provides methods for inducing cardioplegia comprising administering to a subject in need thereof an effective amount of a cardioplegia-inducing agent and a Pyridyl-Substituted Porphyrin Compound. Cardioplegia-inducing agents useful in the present invention include, but are not limited to, potassium chloride, procaine, lidocaine, novocaine, bupivocaine, nicorandil, pinacidil, halothane, St. Thomas solution, Fremes solution, 2,3-butanedione monoxime, or esmolol.

In one embodiment, the cardioplegia-inducing agent is lidocaine.

In one embodiment, a cardioplegia-inducing agent and a Pyridyl-Substituted Porphyrin Compound are present within the same composition. The present methods for inducing cardioplegia are useful for preventing or minimizing myocardial damage from occurring during cardioplegia.

In still another embodiment, the invention provides methods for protecting a subject's heart against myocardial damage during cardioplegia, the method comprising administering to an animal in need thereof an effective amount of:

(a) a cardioplegia-inducing agent; and
(b) a Pyridyl-Substituted Porphyrin Compound.

In one embodiment, the cardioplegia-inducing agent is administered prior to the administration of the Pyridyl-Substituted Porphyrin Compound.

In another embodiment, Pyridyl-Substituted Porphyrin Compound is administered prior to the administration of the cardioplegia-inducing agent.

In a further embodiment, the cardioplegia-inducing agent and the Pyridyl-Substituted Porphyrin Compound are administered concurrently.

In another embodiment, the cardioplegia-inducing agent and the Pyridyl-Substituted Porphyrin Compound are administered such that the Pyridyl-Substituted Porphyrin Compound exerts its prophylactic effect of protection against myocardial damage while the cardioplegia-inducing agent exerts its cardioplegic effect.

5.4.9 Treatment or Prevention of an Inflammatory Condition

The Pyridyl-Substituted Porphyrin Compounds can be used to treat or prevent an inflammatory condition. Inflammatory conditions can arise where there is an inflammation of the body tissue. Examples of inflammatory conditions treatable or preventable using the Pyridyl-Substituted Porphyrin Compounds include, but are not limited to, transplant rejection; chronic inflammatory disorders of the joints, such as arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome (ARDS), and chronic obstructive airway disease; inflammatory disorders of the eye such as corneal dystrophy, trachoma, onchocerciasis, uveitis, sympathetic ophthalmitis and endophthalmitis; chronic inflammatory disorders of the gum, such as gingivitis and periodontitis; tuberculosis; leprosy; inflammatory diseases of the kidney such as uremic complications, glomerulonephritis and nephrosis; inflammatory disorders of the skin such as sclerodermatitis, psoriasis and eczema; inflammatory diseases of the central nervous system, such as chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases such as diabetes mellitus, immune-complex vasculitis, systemic lupus erythematosus (SLE); inflammatory diseases of the heart such as cardiomyopathy, ischemic heart disease hypercholesterolemia, and atherosclerosis; as well as inflammation resulting from various diseases such as preeclampsia, chronic liver failure, brain and spinal cord trauma, and cancer. The Pyridyl-Substituted Porphyrin Compounds can also be used to treat or prevent reduce the progression of an inflammatory condition and/or to reduce the symptoms of the inflammatory condition. In one embodiment, the Pyridyl-Substituted Porphyrin Compounds are useful for treating or preventing pain associated with an inflammatory condition.

The inflammatory condition treatable or preventable by administration of an effective amount of a Pyridyl-Substituted Porphyrin Compound can also be a systemic inflammation of the body. Examples of systemic inflammation include but are not limited to, gram-positive or gram negative shock, sepsis, septic shock, hemorrhagic or anaphylactic shock, (SIRS), or shock induced by cancer chemotherapy in response to a pro-inflammatory cytokine such as IL-2, interferon-γ, or GM-CSF.

In one embodiment, the inflammatory condition is circulatory shock, sepsis, systemic inflammatory response syndrome, hemorrhagic shock, cardiogenic shock, or systemic inflammation induced by an anticancer immunotherapy such as IL-2.

In one embodiment, a Pyridyl-Substituted Porphyrin Compound can be used to treat or prevent an inflammatory skin disease. In one embodiment, the inflammatory skin disease is contact dermatitis, erythema, or psoriasis.

In one embodiment, the inflammatory condition is in a cell or tissue that is exposed to a reactive species.

5.4.10 Treatment or Prevention of a Reperfusion Injury

A reperfusion injury can be treated or prevented by administration of an effective amount of a Pyridyl-Substituted Porphyrin Compound. Reperfusion injury can result following a naturally occurring episode, such as a myocardial infarction, stroke, or during a surgical procedure where blood flow in vessels is intentionally or unintentionally blocked.

Reperfusion injuries that can be treated or prevented by administering an effective amount of a Pyridyl-Substituted Porphyrin Compound include, but are not limited to, intestinal reperfusion injury, stroke, neurotrauma, neuroinjury, myocardial infarction, and reperfusion injury resulting from cardiopulmonary bypass surgery, organ transplantation surgery, thoracoabrominal aneurysm repair surgery, carotid endarerectomy surgery, or hemorrhagic shock.

In one embodiment, the reperfusion injury results from cardiopulmonary bypass surgery, thoracoabrominal aneurysm repair surgery, carotid endarerectomy surgery or hemorrhagic shock.

In one embodiment, a Pyridyl-Substituted Porphyrin Compound is administered during myocardial reperfusion. In one embodiment, the reperfusion results from cardiopulmonary bypass. In another embodiment, the reperfusion results in a myocardial infarction injury.

In one embodiment, the reperfusion injury is a reoxygenation injury resulting from surgery, particularly organ transplantation surgery.

In one embodiment, the organ transplantation is cardiac transplantation or kidney transplantation.

In another embodiment, the organ transplantation is heart transplantation, kidney transplantation, liver transplantation, or lung transplantation.

In one embodiment, the reperfusion injury is in a cell or tissue that is exposed to a reactive species.

5.4.11 Treatment or Prevention of an Ischemic Condition

An ischemic condition can be treated or prevented by administration of an effective amount of a Pyridyl-Substituted Porphyrin Compound.

Ischemic conditions that can be treated or prevented by administering an effective amount of a Pyridyl-Substituted Porphyrin Compound include, but are not limited to, stable angina, unstable angina, myocardial ischemia, hepatic ischemia, mesenteric artery ischemia, intestinal ischemia, critical limb ischemia, chronic critical limb ischemia, erebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

In one embodiment, the ischemic condition is in a cell or tissue that is exposed to a reactive species.

5.4.12 Treatment or Prevention of a Cardiovascular Disease

A cardiovascular disease can be treated or prevented by administration of an effective amount of a Pyridyl-Substituted Porphyrin Compound.

Cardiovascular diseases that can be treated or prevented by administering an effective amount of a Pyridyl-Substituted Porphyrin Compound include, but are not limited to, chronic heart failure, atherosclerosis, congestive heart failure, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

In one embodiment, the cardiovascular disease is a cardiac arrhythmia, congestive heart failure, circulatory shock or cardiomyopathy.

In another embodiment, the cardiac arrhythmia is atrial fibrillation, supraventricular tachycardia, atrial flutter or paroxysmal atrial tachycardia.

In one embodiment, the cardiovascular disease is heart failure.

In another embodiment, the cardiovascular disease is balloon-induced vascular injury, coronary stenting, atherosclerosis, or restenosis.

In another embodiment, the cardiovascular disease is acute heart failure, chronic heart failure, ischemic heart failure, drug-induced heart failure, idiopathic heart failure, alcoholic heart failure, or cardiac arrhythmia.

In one embodiment, the cardiovascular disease is in a cell or tissue that is exposed to a reactive species.

5.4.13 Treatment or Prevention of Diabetes or a Diabetic Complication

Diabetes or a diabetic complication can be treated or prevented by administration of an effective amount of a Pyridyl-Substituted Porphyrin Compound.

Types of diabetes that can be treated or prevented by administering an effective amount of a Pyridyl-Substituted Porphyrin Compounds include, but are not limited to, Type I diabetes (Insulin Dependent Diabetes Mellitus), Type II diabetes (Non-Insulin Dependent Diabetes Mellitus), gestational diabetes, an insulinopathy, diabetes resulting from pancreatic disease, diabetes resulting from another endocrine disease (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

The Pyridyl-Substituted Porphyrin Compounds can also be used to treat or prevent a diabetic complication. Examples of diabetic complications treatable or preventable by administering an effective amount of a Pyridyl-Substituted Porphyrin Compound include, but are not limited to, diabetic cataract, glaucoma, retinopathy, nephropathy (such as microaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathy, autonomic neuropathy, a skin or mucous membrane complication (such as an infection, a shin spot, a candidal infection or necrobiosis lipoidica diabeticorumobesity), a peripheral vascular disease, hyperlipidemia, hypertension, syndrome of insulin resistance, coronary artery disease, diabetic neuropathy, mononeuropathy, a foot ulcer, a joint disease, a fungal infection, a bacterial infection, neuropathy, angiopathy, cardiomyopathy, and erectile dysfunction.

5.4.14 Treatment or Prevention of a Side Effect of Cancer Chemotherapy

A side effect of cancer chemotherapy can be treated or prevented by administration of an effective amount of a Pyridyl-Substituted Porphyrin Compound.

Examples of a side effect of cancer chemotherapy include, but are not limited to, nausea, vomiting, alopecia, myelosuppression, anorexia, neuropathy, headache, pain, dry mouth, mouth sores, bone marrow suppression, hyperpigmentation, skin rash, fluid retention, diarrhea, cardiotoxicity, anaphylaxis, fever and chills, leucopenia, thrombocytopenia, lethargy, nephrotoxicity, ototoxicity, hot flashes, hyperglycemia, and pancreatitis.

In one embodiment, the cancer chemotherapy comprises administering a platinum-based antitumor agent. Accordingly, the present invention encompasses methods for treating or preventing a side effect resulting from administration of a platinum-based antitumor agent, comprising administering to a subject in need thereof an effective amount of a Pyridyl-Substituted Porphyrin Compound. Side effects resulting from administration of a platinum-based antitumor agent are those side effects of cancer chemotherapy listed above. In certain embodiments, platinum-based antitumor agents include, but are not limted to, cisplatin, carboplatin, aroplatin, and oxaliplatin.

In one embodiment, the cancer chemotherapy comprises admininstering doxorubicin.

In a specific embodiment, a Pyridyl-Substituted Porphyrin Compound is administered to a subject in need of treatment or prevention of a side effect of doxorubicin.

In another specific embodiment, a Pyridyl-Substituted Porphyrin Compound is administered to a subject in need of treatment or prevention of a side effect of cisplatin.

5.4.15 Treatment or Prevention of a Radiation-Induced Injury

A radiation-induced injury can be treated or prevented by administration of an effective amount of a Pyridyl-Substituted Porphyrin Compound to a subject.

Examples of a radiation-induced injury treatable or preventable using the present methods include, but are not limited to, an acute radiation syndrome, such as a cerebral syndrome; a gastrointestinal syndrome; a hematopoietic syndrome; acute radiation sickness; pulmonary fibrosis; radiation proctitis; neuropathy; nausea; vomiting; alopecia; pain; headache; esophageal stricture; gastric ulcer; radiation pneumonitis; and cardiomyopathy.

In one embodiment, treating a radiation-induced injury includes increasing a subject's survival time following exposure to radiation.

In another embodiment, death is an example of a radiation-induced injury that is preventable according to the present invention.

The Pyridyl-Substituted Porphyrin Compounds are also useful for protecting bystander healthy tissue from a radiation-induced injury during administration of therapeutic radiation.

A radiation-induced injury may result from exposure of a subject to ionizing radiation from numerous sources including, but not limited to, a nuclear weapon, such as an atomic bomb, a neutron bomb, or a "dirty bomb;" an industrial source, such as a nuclear power plant, a nuclear submarine, or a nuclear waste disposal site; a diagnostic or therapeutic medical or dental application, such as x-rays, CT scans, external radiation therapy, internal radiation therapy (e.g., radioactive "seed" implants used in cancer therapy). The injury might result from an accident, an act of war or terrorism, cumulative exposure at the home or workplace, or purposeful exposure during medical diagnosis or treatment.

In one embodiment, the injury is induced by radiation from a nuclear weapon.

In another embodiment, the injury is induced by radiation from a nuclear power plant.

In still another embodiment, the injury is induced by radiation from radiation therapy that the subject is receiving for the treatment of a non-radiation related disorder.

In still another embodiment, the injury is induced by radiation from radiation therapy that the subject is receiving for the treatment of cancer.

In one embodiment, the injury is induced by radiation from a radioactive material that is ingested by a subject.

In one embodiment, the radiation-induced injury is in a cell or tissue that is exposed to a reactive species.

5.4.16 Treatment or Prevention of Cancer

The invention encompasses methods for treating or preventing cancer, comprising administering to a subject in need thereof an effective amount of a Pyridyl-Substituted Porphyrin Compound.

Examples of cancers treatable or preventable using the Pyridyl-Substituted Porphyrin Compounds include, but are not limited to, the cancers disclosed below in Table 1 and metastases thereof.

TABLE 1

Solid tumors, including but not limited to:
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon cancer
    colorectal cancer
    kidney cancer
    pancreatic cancer
    bone cancer
    breast cancer
    ovarian cancer
    prostate cancer
    esophageal cancer
    stomach cancer
    oral cancer
    nasal cancer
    throat cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    uterine cancer
    testicular cancer
    small cell lung carcinoma
    bladder carcinoma
    lung cancer
    epithelial carcinoma
    glioma
    glioblastoma multiforme
    astrocytoma
    medulloblastoma
    craniopharyngioma
    ependymoma
    pinealoma
    hemangioblastoma
    acoustic neuroma
    oligodendroglioma
    meningioma
    skin cancer
    melanoma TABLE 1-continued neuroblastoma
    retinoblastoma
blood-borne cancers, including but not limited to:
    acute lymphoblastic leukemia ("ALL")
    acute lymphoblastic B-cell leukemia
    acute lymphoblastic T-cell leukemia
    acute myeloblastic leukemia ("AML")
    acute promyelocytic leukemia ("APL")
    acute monoblastic leukemia
    acute erythroleukemic leukemia
    acute megakaryoblastic leukemia
    acute myelomonocytic leukemia
    acute nonlymphocytic leukemia
    acute undifferentiated leukemia
    chronic myelocytic leukemia ("CML")
    chronic lymphocytic leukemia ("CLL")
    hairy cell leukemia
    multiple myeloma
acute and chronic leukemias:
    lymphoblastic
    myelogenous
    lymphocytic
    myelocytic leukemias
Lymphomas:
    Hodgkin's disease
    non-Hodgkin's Lymphoma
    Multiple myeloma
    Waldenstrom's macroglobulinemia
    Heavy chain disease
    Polycythemia vera In one embodiment, the cancer is pancreatic cancer, colorectal cancer, mesothelioma, a malignant pleural effusion, peritoneal carcinomatosis, peritoneal sarcomatosis, renal cell carcinoma, small cell lung cancer, non-small cell lung cancer, testicular cancer, bladder cancer, breast cancer, head and neck cancer, or ovarian cancer.

In still another embodiment, the subject in need of treatment has previously undergone treatment for cancer. Such previous treatments include, but are not limited to, prior chemotherapy, radiation therapy, surgery or immunotherapy, such as cancer vaccines.

The Pyridyl-Substituted Porphyrin Compounds are also useful for the treatment or prevention of a cancer caused by a virus. For example, human papilloma virus can lead to cervical cancer (see, e.g., Hernandez-Avila et al., Archives of Medical Research (1997) 28:265-271), Epstein-Barr virus (EBV) can lead to lymphoma (see, e.g., Herrmann et al., J Pathol (2003) 199(2):140-5), hepatitis B or C virus can lead to liver carcinoma (see, e.g., El-Serag, J Clin Gastroenterol (2002) 35(5 Suppl 2):S72-8), human T cell leukemia virus (HTLV)-I can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11):1574-9), and Human Immune deficiency Virus (HIV) infection contribute to cancer development as a consequence of immunodeficiency (see, e.g., Dal Maso et al., Lancet Oncol (2003) 4(2): 110-9).

The Pyridyl-Substituted Porphyrin Compounds can also be administered to prevent the progression of a cancer, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 68-79 (2d ed. 1976). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of a Pyridyl-Substituted Porphyrin Compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions that can be treated or prevented according to the present invention.

In another embodiment, fibrocystic disease (e.g., cystic hyperplasia, mammary dysplasia, particularly adenosis (benign epithelial hyperplasia)) that can be treated or prevented according to the present invention.

In other embodiments, cancer in a subject who exhibits one or more of the following predisposing factors for malignancy can be treated by administration of an effective amount of a Pyridyl-Substituted Porphyrin Compound: a chromosomal translocation associated with a malignancy, e.g., the Philadelphia chromosome for chronic myelogenous leukemia or t(14;18) for follicular lymphoma; familial polyposis or Gardner's syndrome; benign monoclonal gammopathy; a first degree kinship with persons having a cancer or precancerous disease showing a Mendelian (genetic) inheritance pattern, e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome (see Robbins and Angell, Basic Pathology, 112-112 (2d ed. 1976); and exposure to carcinogens, e.g., smoking, and inhalation of or contacting with certain chemicals.

In another specific embodiment, the Pyridyl-Substituted Porphyrin Compounds are administered to a human subject to prevent progression to breast, colon, ovarian, or cervical cancer.

5.5 Therapeutic/Prophylactic Administration and Compositions of the Invention Due to their activity, the Pyridyl-Substituted Porphyrin Compounds are advantageously useful in veterinary and human medicine. As described above, the Pyridyl-Substituted Porphyrin Compounds are useful for treating or preventing a Condition in a subject in need thereof.

When administered to a subject, the Pyridyl-Substituted Porphyrin Compounds can be administered as a component of a composition that comprises a physiologically acceptable carrier or vehicle. The present compositions, which comprise a Pyridyl-Substituted Porphyrin Compound, can be administered orally. The Pyridyl-Substituted Porphyrin Compounds of the invention can also be administered by any other convenient route, for example, by infusion or bolus injection, by absorption through epithelial or mucocutaneous linings (e.g., oral, rectal, and intestinal mucosa) and can be administered together with another biologically active agent. Administration can be systemic or local. Various delivery systems are known, e.g., encapsulation in liposomes, microparticles, microcapsules, capsules, and can be administered.

Methods of administration include, but are not limited to, intradermal, intramuscular, intraperitoneal, intravenous, ocular, subcutaneous, intranasal, epidural, oral, sublingual, intracerebral, intravaginal, transdermal, rectal, by inhalation, or topical, particularly to the ears, nose, eyes, or skin. In some instances, administration will result in the release of the Pyridyl-Substituted Porphyrin Compounds into the bloodstream. The mode of administration can be left to the discretion of the practitioner.

In one embodiment, the Pyridyl-Substituted Porphyrin Compounds are administered orally.

In other embodiments, it can be desirable to administer the Pyridyl-Substituted Porphyrin Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Pyridyl-Substituted Porphyrin Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the Pyridyl-Substituted Porphyrin Compounds can be formulated as a suppository, with traditional binders and excipients such as triglycerides.

In another embodiment the Pyridyl-Substituted Porphyrin Compounds can be delivered in a vesicle, in particular a liposome (see Langer, *Science* 249:1527-1533 (1990) and Treat or prevent et al., *Liposomes in the Therapy of Infectious Disease and Cancer* 317-327 and 353-365 (1989)).

In yet another embodiment the Pyridyl-Substituted Porphyrin Compounds can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-

1533 (1990) can be used. In one embodiment a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J Med.* 321: 574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the Pyridyl-Substituted Porphyrin Compounds, e.g., the spinal column, brain, skin, lung, thyroid gland, colon or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment the pharmaceutically acceptable excipients are sterile when administered to a subject. Water is a particularly useful excipient when the Pyridyl-Substituted Porphyrin Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment the composition is in the form of a capsule (see e.g. U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In one embodiment the Pyridyl-Substituted Porphyrin Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a Pyridyl-Substituted Porphyrin Compound are also suitable for orally administered compositions. In these latter platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the Pyridyl-Substituted Porphyrin Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the Pyridyl-Substituted Porphyrin Compounds are to be administered by infusion, they can be dispensed, for example, with an infusion bottle containing sterile pharmaceutical grade water or saline. Where the Pyridyl-Substituted Porphyrin Compounds are administered by injection, an ampule of sterile water for injection or saline can be provided so that the ingredients can be mixed prior to administration.

The Pyridyl-Substituted Porphyrin Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of a Pyridyl-Substituted Porphyrin Compound to treat or prevent the Condition in a minimal amount of time. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Pyridyl-Substituted Porphyrin Compound, and can thus reduce the occurrence of adverse side effects.

Controlled- or sustained-release compositions can initially release an amount of a Pyridyl-Substituted Porphyrin Compound that promptly produces the desired therapeutic or prophylactic effect, and gradually and continually release other amounts of the Pyridyl-Substituted Porphyrin Compound to maintain this level of therapeutic or prophylactic effect over an extended period of time. To maintain a constant level of the Pyridyl-Substituted Porphyrin Compound in the body, the Pyridyl-Substituted Porphyrin Compound can be released from the dosage form at a rate that will replace the amount of Pyridyl-Substituted Porphyrin Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Pyridyl-Substituted Porphyrin Compound that is effective in the treatment or prevention of a Condition can be determined by standard clinical techniques. In addition, in vitro or in vivo assays can optionally be employed to help identify optimal dosage ranges. The precise dose to be employed can also depend on the route of administration, the time of the subject's exposure to radiation, the amount of radiation that a subject is exposed to, or the seriousness of the Condition being prevented or treated. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Pyridyl-Substituted Porphyrin Compound is administered, the effective dosage amounts correspond to the total amount administered.

When the Pyridyl-Substituted Porphyrin Compounds are administered for prevention of a radiation-inducted therapy injury, the Pyridyl-Substituted Porphyrin Compounds can be administered 48 hours or less time prior to exposure to radiation. Administration may be repeated at regular intervals as set forth above.

In one embodiment, an intial dose of a Pyridyl-Substituted Porphyrin Compound is administered from about 5 minutes to about one hour prior to exposure to radiation with repeated doses optionally administered at regular intervals thereafter.

The Pyridyl-Substituted Porphyrin Compounds can be assayed in vitro or in vivo for the desired therapeutic or prophylactic activity prior to use in humans. Animal model systems can be used to demonstrate safety and efficacy.

The present methods for treating or preventing a Condition in a subject in need thereof can further comprise administering another therapeutic agent to the subject being administered a Pyridyl-Substituted Porphyrin Compound. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where another therapeutic agent is administered to a subject, the effective amount of the Pyridyl-Substituted Porphyrin Compound is less than its effective amount would be where the other therapeutic agent is not administered. In this case, without being bound by theory, it is believed that the Pyridyl-Substituted Porphyrin Compounds and the other therapeutic agent act synergistically to treat or prevent a Condition.

The other therapeutic agent can be an anti-inflammatory agent. Examples of useful anti-inflammatory agents include, but are not limited to, adrenocorticosteroids, such as cortisol, cortisone, fludrocortisone, prednisone, prednisolone, 6a-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

The other therapeutic agent can be an anti-diabetic agent. Examples of useful anti-diabetic agents include, but are not limited to, glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

The other therapeutic agent can be an anti-cardiovascular disease agent. Examples of useful anti-cardiovascular disease agents include, but are not limited to, carnitine; thiamine; and muscarinic receptor antagonists, such as atropine, scopolamine, homatropine, tropicamide, pirenzipine, ipratropium, tiotropium, and tolterodine.

The other therapeutic agent can be an immunosuppressive agent. Examples of useful immunosuppressive agents include a corticosteroid, a calcineurin inhibitor, an antiproliferative agent, a monoclonal antilymphocyte antibody, a polyclonal antilymphocyte antibody, prednisone, methylprednisolone, cyclosporine, tacrolimus, mycophenolate mofetil, azathioprine, sirolimus, muromonab-CD3, interleukin-2 receptor antagonist, daclizumab, antithymocyte globulin-equine, and antithymocyte globulin-rabbit. In one embodiment, the methods for treating or preventing a reoxygenation injury resulting from organ transplantation further comprises administering an immunosuppressive agent.

The other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

The other therapeutic agent can be an anticancer agent. The Pyridyl-Substituted Porphyrin Compound and the other anticancer agent can act additively or synergistically. A synergistic use of a Pyridyl-Substituted Porphyrin Compound and another anticancer agent permits the use of lower dosages of one or more of these agents and/or less frequent administration of the agents to a subject with cancer. The ability to utilize lower dosages of a Pyridyl-Substituted Porphyrin Compound and/or additional anticancer agents and/or to administer the agents less frequently can reduce the toxicity associated with the administration of the agents to a subject without reducing the efficacy of the agents in the treatment of cancer. In addition, a synergistic effect can result in the improved efficacy of these agents in the treatment of cancer and/or the reduction of adverse or unwanted side effects associated with the use of either agent alone.

In one embodiment, the Pyridyl-Substituted Porphyrin Compound and the anticancer agent can act synergistically when administered in doses typically employed when such agents are used as monotherapy for the treatment of cancer. In another embodiment, the Pyridyl-Substituted Porphyrin Compound and the anticancer agent can act synergistically when administered in doses that are less than doses typically employed when such agents are used as monotherapy for the treatment of cancer.

In one embodiment, the additional anticancer agent can be, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum containing complexes: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| Anti-metabolites | |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |
| Pyrimidine analogs: | |
| Uracil analogs: | 5-Fluorouracil |
| | Fluoxuridine |
| | Doxifluridine |
| | Ralitrexed |
| Cytosine analogs: | Cytarabine (ara C) |
| | Cytosine arabinoside |
| | Fludarabine |
| | Gemcitabine |
| | Capecitabine |

TABLE 2-continued

| Purine analogs: | Mercaptopurine |
|---|---|
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goscrclin |
| | Leuprolide acetate |
| Anti-androgens: | Flutamide |
| | Bicalutamide |
| Retinoids/Deltoids | |
| | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |

TABLE 2-continued

|  |  |
|---|---|
|  | NM-3 |
|  | Panzem |
|  | PI-88 |
|  | Placental ribonuclease inhibitor |
|  | Plasminogen activator inhibitor |
|  | Platelet factor-4 (PF4) |
|  | Prinomastat |
|  | Prolactin 16 kD fragment |
|  | Proliferin-related protein (PRP) |
|  | PTK 787/ZK 222594 |
|  | Retinoids |
|  | Solimastat |
|  | Squalamine |
|  | SS 3304 |
|  | SU 5416 |
|  | SU6668 |
|  | SU11248 |
|  | Tetrahydrocortisol-S |
|  | Tetrathiomolybdate |
|  | Thalidomide |
|  | Thrombospondin-1 (TSP-1) |
|  | TNP-470 |
|  | Transforming growth factor-beta (TGF-β) |
|  | Vasculostatin |
|  | Vasostatin (calreticulin fragment) |
|  | ZD6126 |
|  | ZD 6474 |
|  | farnesyl transferase inhibitors (FTI) |
|  | Bisphosphonates |
| Antimitotic agents: | Allocolchicine |
|  | Halichondrin B |
|  | Colchicine |
|  | colchicine derivative |
|  | dolstatin 10 |
|  | Maytansine |
|  | Rhizoxin |
|  | Thiocolchicine |
|  | trityl cysteine |
| Others: |  |
| Isoprenylation inhibitors: |  |
| Dopaminergic neurotoxins: | 1-methyl-4-phenylpyridinium ion |
| Cell cycle inhibitors: | Staurosporine |
| Actinomycins: | Actinomycin D |
|  | Dactinomycin |
| Bleomycins: | Bleomycin A2 |
|  | Bleomycin B2 |
|  | Peplomycin |
| Anthracyclines: | Daunorubicin |
|  | Doxorubicin (adriamycin) |
|  | Idarubicin |
|  | Epirubicin |
|  | Pirarubicin |
|  | Zorubicin |
|  | Mitoxantrone |
| MDR inhibitors: | Verapamil |
| $Ca^{2+}$ATPase inhibitors: | Thapsigargin |

5.5.1 Multi-Therapy for Cancer

The Pyridyl-Substituted Porphyrin Compounds can be administered to a subject that has undergone, is currently undergoing, or is about to undergo one or more additional anticancer treatments including, but not limited to, surgery, radiation therapy, or immunotherapy, such as administration of a cancer vaccine.

The present methods for treating cancer can further comprise administering surgery, radiation therapy, or immunotherapy.

In one embodiment, the anticancer treatment is immunotherapy.

In one embodiment, the immunotherapy is a cancer vaccine.

In one embodiment, the anticancer treatment is radiation therapy.

In another embodiment, the anticancer treatment is surgery.

In a specific embodiment, a Pyridyl-Substituted Porphyrin Compound is administered concurrently with radiation therapy. In another specific embodiment, the additional anticancer treatment is administered prior or subsequent to the administration of the Pyridyl-Substituted Porphyrin Compound, in one embodiment at least an hour, five hours, 12 hours, a day, a week, a month, or several months (e.g., up to three months), prior or subsequent to administration of the Pyridyl-Substituted Porphyrin Compounds.

When the additional anticancer treatment is radiation therapy, any radiation therapy protocol can be used depending upon the type of cancer to be treated or prevented. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered.

Additionally, the invention provides methods of treatment of cancer using the Pyridyl-Substituted Porphyrin Compounds as an alternative to chemotherapy or radiation therapy where the chemotherapy or the radiation therapy results in negative side effects in the subject being treated. The subject being treated can, optionally, be treated with another anticancer treatment modality such as surgery, radiation therapy, or immunotherapy.

The Pyridyl-Substituted Porphyrin Compounds can also be used in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of a Pyridyl-Substituted Porphyrin Compound and/or radiation therapy, and the stem cell graft is infused back into the subject.

A Pyridyl-Substituted Porphyrin Compound and the other therapeutic agent can act additively or, in one embodiment synergistically. In one embodiment a Pyridyl-Substituted Porphyrin Compound is administered concurrently with another therapeutic agent. In one embodiment a composition comprising an effective amount of a Pyridyl-Substituted Porphyrin Compound and an effective amount of another therapeutic agent can be administered. Alternatively, a composition comprising an effective amount of a Pyridyl-Substituted Porphyrin Compound and a different composition comprising an effective amount of another therapeutic agent can be concurrently administered. In another embodiment, an effective amount of a Pyridyl-Substituted Porphyrin Compound is administered prior or subsequent to administration of an effective amount of another therapeutic agent. In this embodiment the Pyridyl-Substituted Porphyrin Compound is administered while the other therapeutic agent exerts its therapeutic effect, or the other therapeutic agent is administered while the Pyridyl-Substituted Porphyrin Compound exerts its preventative or therapeutic effect for treating or preventing a Condition.

A composition of the invention can be prepared by a method comprising admixing a Pyridyl-Substituted Porphyrin Compound and a physiologically acceptable carrier or vehicle. Admixing can be accomplished using methods well known for admixing a compound and a physiologically acceptable carrier or vehicle. In one embodiment the Pyridyl-Substituted Porphyrin Compound is present in the composition in an effective amount.

5.6 Kits

The invention encompasses kits that can simplify the administration of a Pyridyl-Substituted Porphyrin Compound to a subject.

A typical kit of the invention comprises a unit dosage form of a Pyridyl-Substituted Porphyrin Compound. In one embodiment the unit dosage form is within a container, which can be sterile, containing an effective amount of a Pyridyl-Substituted Porphyrin Compound and a physiologically acceptable carrier or vehicle. The kit can further comprise a label or printed instructions instructing the use of the Pyridyl-Substituted Porphyrin Compound to treat or prevent a Condition. The kit can also further comprise a unit dosage form of another therapeutic agent, for example, a container containing an effective amount of the other therapeutic agent. In one embodiment the kit comprises a container containing an effective amount of a Pyridyl-Substituted Porphyrin Compound and an effective amount of another therapeutic agent. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

6. EXAMPLES

General Methods

Proton NMR spectra were obtained using a Varian 300 MHz spectrophotometer and chemical shift values (δ) are reported in parts per million (ppm). TLC was performed using TLC plates precoated with silica gel 60 F-254. Intermediates and final compounds were characterized on the basis of $^1$H NMR and MS data, HPLC, elemental analysis.

6.1 Example 1

Synthesis of Compound 1

A 50 L three-neck reaction flask containing propionic acid (30 L) was equipped with two addition funnels and a reflux condenser. One addition funnel was charged with a solution of pyrrole (417 mL, 6.0 mol) in toluene (583 mL), and the second addition funnel was charged with a solution of 2-pyridinecarboxaldehyde (568 mL, 6.0 mol) in toluene (432 mL). The propionic acid was heated to reflux and then the contents of the addition funnels were added simultaneously at approximately equal rates over 2 hours, with vigorous stirring to the refluxing propionic acid. The resultant dark red-brown reaction mixture was heated at reflux for 1 hour, then the heat source was removed and the reaction mixture was allowed to stir for about 18 hours at room temperature. The resultant black solution was filtered through #1 filter paper and concentrated in vacuo to provide a black oily residue. The black oily residue was diluted with toluene (5 L) and the resultant solution was stirred for 1 minute, then concentrated in vacuo. This dilution/concentration was repeated three times and the resultant black solid residue was diluted with ethyl acetate (5 L) and the resultant solution was stirred at room temperature for about 18 hours. The resultant solution was filtered through #1 filter paper, the collected solids were diluted with dichloromethane (2 L) and the resultant solution was purified using flash column chromatography on silica gel (10 kg) using dichloromethane: triethylamine (98:2 vol:vol) as eluent. The relevant fractions were combined and concentrated in vacuo, and the resultant black granular solid was diluted with 10% aqueous ammonium hydroxide (2 L), and the resultant suspension was stirred vigorously for 2 hours. The resultant suspension was filtered through #1 filter paper, and the collected black solids were washed with deionized water (4×1 L). The washed solids were then suspended in ethyl acetate (2 L), and the resultant solution was stirred for 1 hour then filtered through #1 filter paper. The collected eggplant-colored granular solid was diluted with 1,2-dichloroethane (1 L) and the resultant solution was stirred for 2 hours, then filtered through #1 filter paper. The collected solids were washed with 1,2-dichloroethane (4×200 mL), then dried in vacuo overnight to provide Compound 1 as a brilliant deep metallic purple solid. Yield=64.26 g (7%). $R_f$=0.56 (silica, 9:1 dichloromethane: 7 N ammonia in methanol); $^1$H NMR (CDCl$_3$) δ 9.14 (d, J=3.9 Hz, 4H), 8.87 (S, 8H), 8.21 (d, J=7.5 Hz, 4H), 8.10 (dt, J$_1$=1.8 Hz, J$_2$=7.8 Hz, 4H), 7.71 (dd, J$_1$=5.1 Hz, J$_2$=7.5 Hz, 4H); $^{13}$C NMR (CDCl$_3$) δ 160.7, 148.8, 134.9, 132.2, 130.6, 122.6, 122.6, 119.0; mass spectrum ("MS") m/z=619 (M+H).

6.2 Example 2

Synthesis of Compound 2

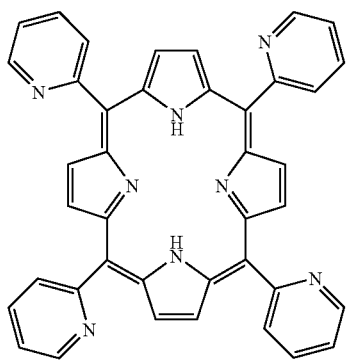

1

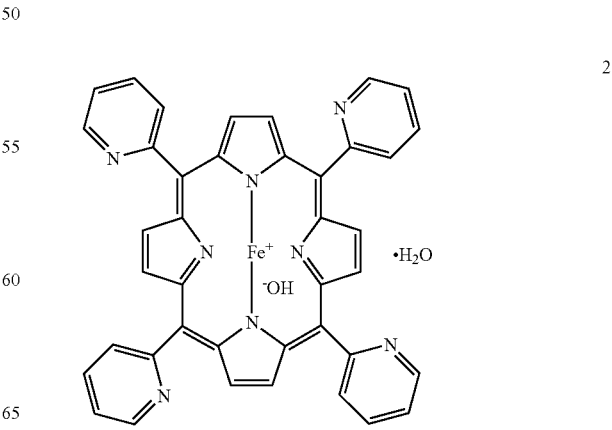

2

Ferric chloride (14.3 g; 88.89 mmol) was added to a suspension of Compound 1 (50.0 g, 80.39 mmol) in 1 N hydrochloric acid (245 mL, 3 eq.) and the resultant reaction mixture was heated to reflux and stirred for about 18 hours. The resultant dark brown reaction mixture was cooled to room temperature and basified using 5N sodium hydroxide (160 mL). The resultant precipitate was vacuum filtered through Whatman #50 filter paper and washed sequentially with deionized water (4×1.5 L) and diethyl ether (1.5 L). The resultant purple-black solid was subsequently dried in vacuo for 3 days at 100° C., then dissolved in dichloromethane (200 mL) and vacuum filtered through a one-inch pad of Celite. The Celite cake was washed with a solution of 9:1 (vol:vol) dichloromethane: methanol until the filtrate was nearly colorless. The filtrate was then concentrated in vacuo to provide Compound 2 as its monohydrate as a purple-black iridescent powdered solid. Yield=25.74 g (47%). MS m/z=672(M+). Anal. Calc. for $C_{40}H_{27}FeN_8O_2$: 67.91% C, 3.82% H, 7.90% Fe, 15.85% N, 4.53% O. Found: 67.84% C, 3.63% H, 7.70% Fe, 15.92% N.

6.3 Example 3

Synthesis of Compound 3

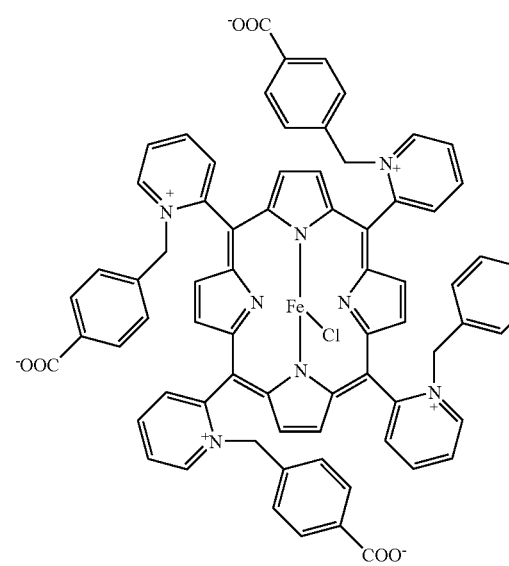

Method 1:

Compound 2 (25 g) was diluted in N-methyl pyrrolidinone (250 mL) and stirred to form a slurry. α-Bromo-p-toluic acid (157 g, 20 eq.) was then added to the slurry and the resultant reaction mixture was stirred under nitrogen atmosphere at 130° C. for about 70 hours. The reaction mixture was cooled to room temperature and poured slowly into a vigorously stirring volume of chloroform (2.75 L). The resultant suspension was filtered through a three-inch pad of Celite and the dark-brown precipitate was removed from the filter funnel along with the top one-inch of the Celite pad. The combined precipitate and Celite were extracted with chloroform (1.5 L) in a Soxhlet extractor for about 55 hours. The extracted solid was removed from the Soxhlet thimble and diluted in 2.5 L of a mixture of MeOH:H₂O (1:1) and the resultant solution was filtered through a medium porosity glass fritted funnel. The filtrate was mixed with Dowex Marathon WBA-2 weakly basic anion exchange resin (340 mL, 16 eq.) and the resultant solution was stirred for about 20 hours, then filtered. The resin was washed with 500 mL of 1:1 MeOH:H₂O and the combined filtrate was eluted down a one-inch O.D. glass column of 340 mL of Dowex Marathon WBA-2 resin at a flow rate of 15-20 mL/min. using 500 mL of 1:1 MeOH:H₂O as eluent. The combined filtrates were mixed with 240 mL (8 eq.) of Amberlite IRA-402 chloride form strongly basic anion-exchange resin and stirred for about 4 hours. The resultant solution was filtered using a coarse porosity glass fritted funnel and the resin resin was washed with 500 mL of 1:1 MeOH:H₂O and the combined filtrate was eluted down a one-inch O.D. glass column of 340 mL of Dowex Marathon WBA-2 resin at a flow rate of 15-20 mL/min. using 500 mL of 1:1 MeOH:H₂O as eluent. The filtrate was passed through a one-inch O.D. glass column of 240 mL of Amberlite IRA-402 chloride resin at a flow rate of 15-20 mL/min. The resin was then washed with 500 mL of 1:1 MeOH:H₂O and the combined filtrates were vacuum filtered though a 0.22 μm membrane and concentrated in vacuo to a volume of about 2 L. This solution was then shell-frozen and lyophilized to provide Compound 3 as a black solid.

Method 2:

A 12 L reactor was charged with with 7.9 L of N-methyl pyrrolidinone (NMP) and heated to 120° C. 787.5 g of Compound 21 (Example 11) was added, followed by 4.521 kg of α-bromo-p-toluic acid. The reaction mixture was stirred under nitrogen atmosphere at 120° C. for 6-7 hours, then poured slowly into a 30 L flask containing 10 L of vigorously stirred chloroform. The remaining residue in the 12 L reactor was rinsed into the stirred chloroform mixture with 6 L of chloroform. The resultant suspension was filtered through a 3" thick celite bed in an 18 inch filter funnel, and the black, product-containing layer of celite was removed from the filter bed and transferred to a 12 L reactor equipped with a mechanical stirrer. 5 L of chloroform was added to the reactor, and the resultant mixture was stirred and heated at reflux for 15 minutes. The chloroform suspension was hot-filtered, the filtered solids were returned to the 12 L reactor, and the aforementioned extraction procedure was repeated twice. The solids were again returned to the 12 L reactor, 5 L of methanol was added, and the resultant mixture stirred for 15 minutes at ambient temperature. The solids were removed by vacuum filtration and returned to the 12 L reactor, and the methanol extraction was repeated until the filtrate was substantially clear. The combined methanol extracts were concentrated in vacuo to provide 1.544 kg of crude Compound 3.

HPLC Analysis of Compound 3

The black solid Compound 3 (1 mg, prepared using Method 1, described above) was dissolved in 1 mL of 0.1M HCl. 10 μL of the resultant solution was injected onto a Phenomenex Synergi POLAR-RP HPLC column (4 μM, 80 Å, 105 mm×4.6 mm). The column was eluted at 1 mL/minute using a two-component mixture of (1) water with 0.1% trifluoroacetic acid ("solvent 1"); and (2) methanol with 0.1% trifluoroacetic acid ("solvent 2") in the following gradient:

| Time (min) | Solvent 1 | Solvent 2 | Flow Rate (mL/min) |
| --- | --- | --- | --- |
| 0 | 65% | 35% | 1 |
| 13 | 65% | 35% | 1 |
| 20 | 40% | 60% | 1 |
| 21 | 10% | 90% | 1 |
| 25 | 10% | 90% | 1 |

Results show that the Compound 3 comprises three isomers: an isomer (Compound 3A) having a retention time of about 4 minutes; an isomer (Compound 3B) having a retention time of about 10 minutes; and an isomer (Compound 3C) having a retention time of about 17.2 minutes. Each of Compounds 3A, 3B, and 3C is one of Isomer Nos. 1-8 of Compound 3

6.4 Example 4

Isolation of Compound 3A

Method 1:

Step 1—pH Titration

A Compound 3 mixture of isomers (5 g, prepared using the method described in Example 3, Method 1) was diluted using 0.1M HCl (100 mL), and to the resultant solution was added 1M NaOH (about 18 mL) dropwise until the pH was about 6.0. This solution was then filtered through a 0.2 µM nylon filter and the collected solid was washed with water (about 50 mL). The filtrate and wash were combined and concentrated in vacuo, then further dried in a vacuum oven to provide 4.2 g of a solid crude residue.

Step 2—Removal of Hydrophobes Via Water Elution

The solid crude residue (1 g, prepared using the method of Step 1) was dissolved in water (10 mL), and the resultant solution was loaded onto a polymeric resin column (8-inch effective length, 0.5-inch internal diameter, 12 cm packed bed length, packed with 10 g of MCI gel CHP20P stryene divinylbenzene polymeric resin) and equilibrated using 300 mL of water). The column was eluted at a flow rate of about 5 mL/minute using water as the mobile phase and 20 mL fractions were collected. After collecting 15 fractions, the column was sequentially eluted with methanol (15 mL), and 0.1M HCl (25 mL), and then flushed with methanol and stored for subsequent use. Fractions 2-12 were combined and concentrated in vacuo to provide a residue. The residue was analyzed using HPLC and shown to comprise Compound 3A, Compound 3C, and a few minor unidentified impurities.

Step 3—Isolation and Purification of Compound 3A and Compound 3C

The residue obtained from reduced fractions 2-12 (150 mg), as described in Step 2, was dissolved in 5 mM HCl (3 mL), and the resultant solution was loaded onto an equilibrated flash chromatograpy column (12-inch effective length, 0.5-inch internal diameter) using Phenomenex Sepra Phenyl resin (50 mM, 65 Å) as stationary phase (20 g of resin was packed as a slurry in methanol and equilibrated using 500 mL of 5 mM HCl prior to loading). The column was eluted at a flow rate of about 3 mL/minute using 5 mM HCl (pH of about 2.5, degassed for about 30 minutes prior to elution) as the mobile phase and 30 mL fractions were collected from the point of loading. Fractions shown by HPLC analysis to contain Compound 3A (at >95 are % using the HPLC analysis described in Example 3) were combined to provide the "Compound 3A pool" (total volume of combined fractions=about 600 mL). The stationary phase was then sequentially washed using 0.1M HCl (30 mL), methanol (300 mL) and stored for subsequent use. The washes were then combined to provide the "Compound 3C pool" (about 100 mL total volume).

Step 4—Solvent Exchange of the Compound 3A Pool

A Compound 3A (600 mL) pool obtained using the method described in Step 3, was adjusted to pH 1.0 using concentrated HCl (about 30 mL), and the resultant solution was loaded onto a polymeric resin column (12 inch effective length, 1.0 inch internal diameter, packed with 35 g of MCI gel CHP20P stryene divinylbenzene polymeric resin (Supelco, St. Louis, Mo.)) and equilibrated using 500 mL of 0.1M HCl. After loading, additional 0.1M HCl (100 mL) was loaded onto the column to complete adsorption. The column was then eluted at a flow rate of about 5 mL/minute using methanol as the mobile phase and all fractions containing Compound 3A were combined to provide a subsequent Compound 3A pool of 300 mL (in methanol).

Step 5—Counterion Removal Using Ion-Exchange

A Compound 3A pool (300 mL), obtained using the method described in Step 4, was concentrated in vacuo to a final volume of about 300 mL and then stirred with DOWEX Marathon WBA-2 weakly basic ion-exchange resin (50 mL of aqueous solution of settled resin) for about 18 hours at room temperature and vacuum filtered through a 0.2 µM nylon filter. The filtrate was then passed through a column containing fresh DOWEX Marathon WBA-2 weakly basic ion-exchange resin (50 mL of aqueous solution of settled resin) and the filtrate was pooled. The resin was then washed with methanol and the methanol wash was added to the pooled filtrate.

Step 6—Chlorine Counterion Bonding to Iron

The filtrate pool obtained using the method described in Step 5 was stirred with Amberlite IRA-402 strongly basic ion-exchange resin (10 mL of aqueous solution of settled resin) for about 3 hours at room temperature and vacuum filtered through a 0.2 µM nylon filter. The filtrate was then passed through a column containing fresh Amberlite IRA-402 strongly basic ion-exchange resin (10 mL of aqueous solution of settled resin) and the filtrate was collected and pooled. The resin was then washed with methanol and the methanol wash was added to the pooled filtrate. The pooled filtrate was concentrated in vacuo and dried on high vacuum for about 18 hours to provide a solid residue which was pulverized into a fine powder, transferred to a drying dish and dried in a vacuum oven at 45° C. for about 72 hours to provide Compound 3A as a powdered solid (50 mg, >96% purity by HPLC).

Method 2:

1.544 kg of crude Compound 3 (Example 3, Method 2) was dissolved in 50 L of 0.1 N aqueous hydrochloric acid, and the resultant solution was stirred and titrated to pH 6 with 5 N aqueous sodium hydroxide and stirred for 1 h. The resultant suspension was vacuum filtered through a 3" thick bed of celite in an 18" filter funnel, and the filtered solids were washed with 20 L of water. The solids were highly enriched in Compound 3B (approximately 80% by HPLC), which was extracted from the celite with 1:1 1 N HCl:MeOH. The solvent was removed in vacuo to provide Compound 3B in sufficient purity for further purification by preparatory HPLC.

The aqueous filtrate was subsequently titrated to pH 0.5 with concentrated (12.1 N) aqueous HCl. 23.5 L of the pH 0.5 aqueous solution was loaded onto a column of 5.0 kg of MCI-gel divinylbenzene polymeric resin in 0.1 N HCl. Compounds 3A and 3C adsorbed to the column in a narrow band, and were eluted with 0.1 N HCl. Fractions of 20L, then 4×5 L, then 20 L were collected. Fractions containing greater than 50% of Compound 3A (retention time=4 min) were combined, as were fractions containing greater than 50% of Compound 3C (retention time=17 min). The column was then washed with 20 L of 1:1 MeOH: IN HCl, followed by 20 L of methanol, and 10 L of 0.1 N HCl.

This procedure was repeated twice with 23.3 L volumes of the pH 0.5 aqueous solution. Fractions containing Compound 3A and those containing Compound 3C were combined and concentrated in vacuo to provide 217 g of Compound 3A in sufficient purity for further purification by preparatory HPLC.

8.0 grams of Compound 3A fraction pool were then dissolved in 425 mL of water having 0.1% trifluoroacetic acid (vol/vol) and mixed for no less than 15 minutes. The solution was filtered through a 0.22 μm nylon membrane providing 450 mL of a column-injectable solution.

The column used for purification was packed with 345 grams of Phenomenex, Synergi, POLAR-RP, 10 μm particle size, 80 Å pore size resin. The column dimensions were 310 mm×50 mm (diam.) and the resin was packed into the column via a Dynamic Axial Compression method.

The column was equilibrated before injection by using water with 0.1% trifluoroacetic acid (vol/vol) and at a flow rate of 80 mL/min for a minimum period of 45 minutes.

The column injectable solution was injected as outlined below, and the chromatographic separation was carried out using a two-component system of water with 0.1% trifluoroacetic acid ("solvent 1") and methanol with 0.1% trifluoroacetic acid ("Solvent 2") under the following gradient conditions:

| Time (min:sec) | Solvent 1 | Solvent 2 | Flow Rate (mL/min) |
| --- | --- | --- | --- |
| 0:00 | 100% | 0% | 80 |
| 0:30 | 100% | 0% | 80 |
| 0:31 - injection until fully loaded (about 8 minutes) | 100% | 0% | 80 |
| 10:00 | 100% | 0% | 80 |
| 50:00 | 70% | 30% | 80 |
| 58:00 | 70% | 30% | 80 |
| 60:00 | 10% | 90% | 80 |
| 80:00 | 10% | 90% | 80 |
| 82:00 | 100% | 0% | 80 |

Fractions were collected beginning at about 24 minutes (run time), when Compound 3A began to elute. The first fraction volume taken was 100 mL; all subsequent fraction volumes were 320 mL. Fraction collection ended at about 58 minutes.

Fractions that contained Compound 3A at >98 area % (using the HPLC analysis method described in Example 3) were combined to provide the "Compound 3A Prep LC Pool." The total volume of combined fractions was about 2.5 L.

The Compound 3A Prep LC Pool (2.5L) was concentrated in vacuo to a final volume of 300 mL and then stirred with AMBERLITE IRA-402 (Chloride form) strongly-basic anion-exchange resin (120 mL of aqueous solution of settled resin) for a period of 3 hours at room temperature, and subsequently vacuum filtered through a 0.22 μm nylon membrane. The filtrate was passed through a column containing fresh AMBERLITE IRA-402 (Chloride form) strongly-basic anion-exchange resin (120 mL of aqueous solution of settled resin) and the product effluent was collected. The resin was washed with methanol and the methanol wash was added to the collected product effluent.

The product effluent was vacuum filtered through a 0.22 μm nylon membrane, concentrated in vacuo, and dried under high vacuum for about 18 hours. The resultant solid residue was pulverized into a fine powder, transferred to a drying dish and dried in vacuo at 45° C. for about 72 hours to provide Compound 3A as a powdered solid, pentachloride salt (n=5) (5.5 grams, >98% purity by HPLC).

6.5 Example 5

Isolation and Purification of Compound 3C

Step 1—Solvent Exchange on Compound 3C Pool 30 mg of a residue obtained from in vacuo concentration of the Compound 3C pool (obtained using the method described in Example 4, Step 3) was dissolved in about 6 mL of water. The resultant solution was filtered through a 0.2 μM nylon syringe filter. The filtered solution was then injected onto a Phenomenex Synergi POLAR-RP HPLC column (10 μM, 80 Å, 250 mm×50 mm). The column was eluted at 120 mL/minute using a two-component mixture of (1) water with 0.1% trifluoroacetic acid ("solvent 1"); and (2) methanol with 0.1% trifluoroacetic acid ("solvent 2") in the following gradient:

| Time (min) | Solvent 1 | Solvent 2 | Flow Rate (mL/min) |
| --- | --- | --- | --- |
| 0 | 65% | 35% | 120 |
| 13 | 65% | 35% | 120 |
| 20 | 40% | 60% | 120 |
| 21 | 10% | 90% | 120 |
| 25 | 10% | 90% | 120 |

Fractions (30 mL each) eluting between 13 and 17 minutes at the sustained flow rate of 120 mL/min were collected and analyzed. Fractions shown to contain Compound 3C at >95 area % (using the HPLC analysis method described in Example 3) were combined to provide the "Compound 3C prep LC pool" (total volume of combined fractions=about 240 mL).

Step 2—Counterion Removal Using Ion-Exchange

The Compound 3C prep LC pool (240 mL, obtained in Step 1) was concentrated in vacuo to a final volume of about 50 mL and then sirred with DOWEX Marathon WBA-2 weakly basic ion-exchange resin (10 mL of aqueous solution of settled resin) for about 18 hours at room temperature and vacuum filtered through a 0.2 μM nylon filter. The filtrate was then passed through a column containing fresh DOWEX Marathon WBA-2 weakly basic ion-exchange resin (10 mL of aqueous solution of settled resin) and the filtrate was collected and pooled. The resin was then washed with methanol and the methanol wash was added to the pooled filtrate.

Step 3—Chlorine Ligand Attachment to Iron Center

The pooled filtrate from Step 2 was concentrated in vacuo to a final volume of about 10 mL and then stirred with Amberlite IRA-402 strongly basic ion-exchange resin (1 mL of aqueous solution of settled resin) for about 3 hours at room temperature and vacuum filtered through a 0.2 μM nylon filter. The filtrate was then passed through a column containing fresh Amberlite IRA-402 strongly basic ion-exchange resin (1 mL of aqueous solution of settled resin) and the filtrate was collected and pooled. The resin was then washed with methanol and the methanol wash was added to the pooled filtrate. The pooled filtrate was concentrated in vacuo and dried on high vacuum for about 18 hours to provide a solid residue which was pulverized into a fine powder, transferred to a drying dish and dried in a vacuum oven at 45° C. for about 72 hours to provide Compound 3C as a powdered solid (6.1 mg, >96% purity by HPLC).

6.6 Example 6

Synthesis of Compound 4

4

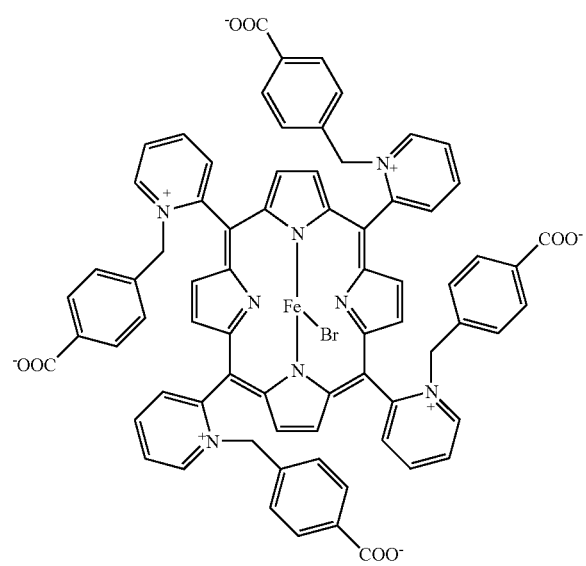

Following the procedure described in Example 3, but omitting the step of adding the Amberlite IRA-402 chloride form strongly basic anion-exchange resin, Compound 4 was obtained.

6.7 Example 7

Synthesis of Compound 9

9

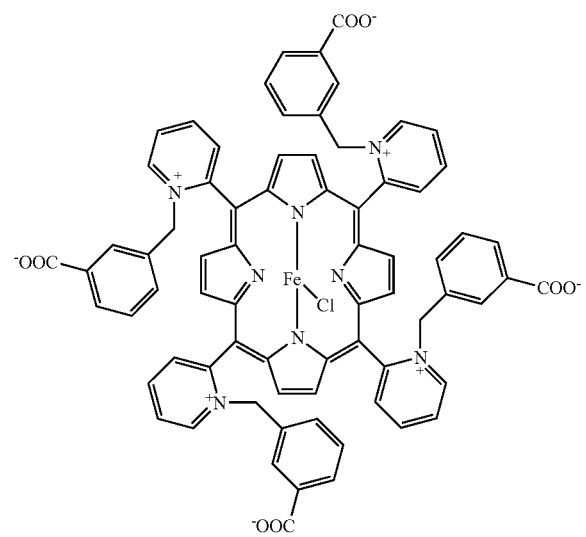

Synthesis of 3-bromomethylbenzoic acid:
In a 1 L round bottom flask fitted with a reflux condenser, a stirred suspension of 10.00 g of m-toluic acid and 14.37 g (1.1 eq.) N-bromosuccinimide in 735 mL chloroform was sparged for 0.5 h with nitrogen. The sparging was discontinued, and the suspension was stirred and irradiated under nitrogen atmosphere using a 500 W quartz halogen lamp at 75% power, causing the solids to dissolve and the chloroform to reflux. The red color of the reaction mixture disappeared after 1.25 h, and 14.37 g of N-bromosuccinimide was added. The reaction mixture was stirred and irradiated under nitrogen atmosphere with a 500 W quartz halogen lamp at 75% power for another 1.5 h, at which time the solution became colorless. The solvent volume was reduced in vacuo to about 100 mL, and then cooled to −20° C. The resultant suspension was vacuum filtered through a bed of dry silica. The silica was washed with 800 mL of chloroform. The chloroform filtrate was reduced in vacuo to about 100 mL, and then cooled to −20° C. The resultant crystals were vacuum filtered, washed with 30 mL of chloroform followed by 50 mL of hexanes, then dissolved in 250 mL chloroform and washed in a separatory funnel with 3×300 mL volumes of water followed by one 300 mL volume of brine to remove traces of succinimide. The organic phase was dried with magnesium sulfate, vacuum filtered, and the solvent was removed in vacuo to provide 9.56 g (61%) of 3-bromomethylbenzoic acid as a white crystalline power.

Formation of Compound 9:
Compound 9 is obtained according to Method 2 in Example 3, but by substituting 3-bromomethylbenzoic acid for α-Bromo-p-toluic acid.

Isolation of Compound 9:
Compound 9 is isolated as set forth in Example 4, Method 2, but the initial titration is pH 6 and the precipitation of Compound 9 is omitted. Crude Compound 9 is dissolved in 0.1 N HCl and loaded onto the MCI-gel column directly.

6.8 Example 8

Synthesis of Compound 12

12

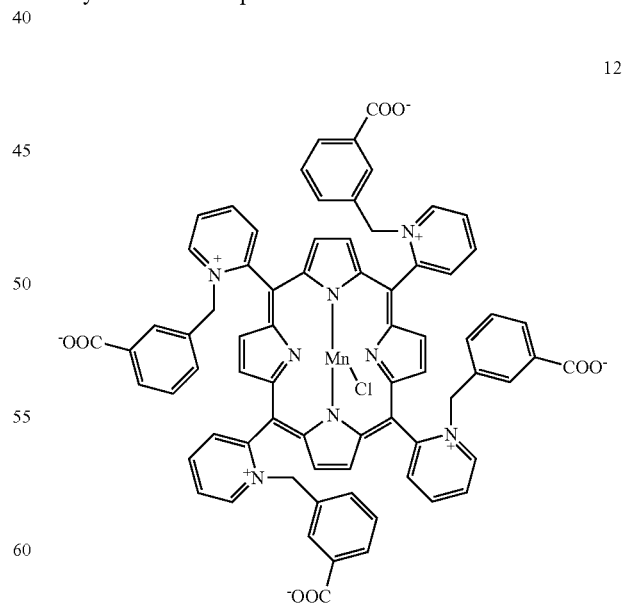

Formation of Compound 12:
Compound 12 is obtained according to Examples 12, 3 (Method 2), and 7.

Isolation of Compound 12:

Compound 12 is isolated as set forth in Example 4, Method 2, but the initial titration to pH 6 and the precipitation of Compound 12 was omitted. Crude Compound 12 was dissolved in 0.1 N HCl and loaded onto the MCI-gel column directly.

6.9 Example 9

Synthesis of Compound 27 and Compound 15

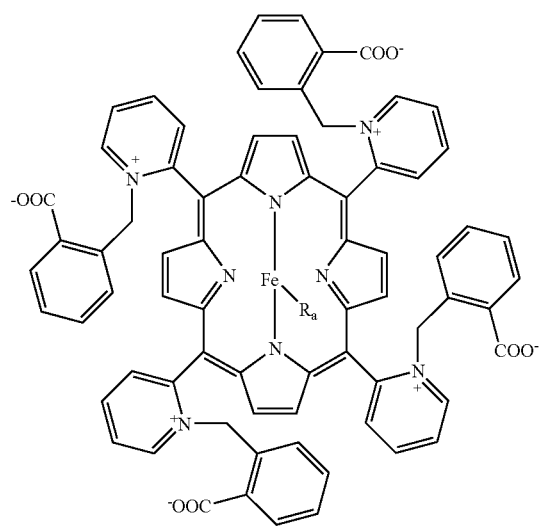

27

Ra = 2-methylbenzoate

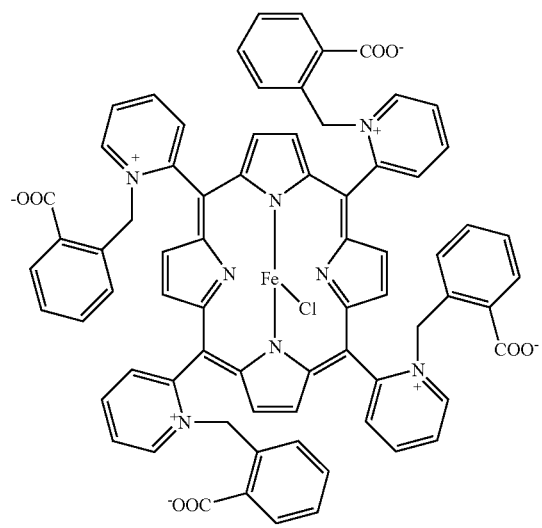

15

Synthesis of 2-bromomethylbenzoic acid:

In a 1 L round bottom flask fitted with a reflux condenser, a stirred suspension of 10.00 g of o-toluic acid and 19.56 g (1.5 eq.) N-bromosuccinimide in 735 mL chloroform was sparged for 0.5 h with nitrogen. The sparging was discontinued, and the suspension was stirred and irradiated under nitrogen atmosphere using a 500 W quartz halogen lamp at 75% power, causing the solids to dissolve and the chloroform to reflux. The red color of the reaction mixture disappeared after 1.5 h, and 6.52 g (0.5 eq.) of N-bromosuccinimide was added. The reaction mixture was stirred and irradiated under nitrogen atmosphere with a 500 W quartz halogen lamp at 75% power for another 1.5 h, at which time the solution became colorless. The solvent volume was reduced in vacuo to about 100 mL, and then cooled to −20° C. The resultant suspension was vacuum filtered through a 1 cm bed of dry silica in a 150 mL fritted funnel. The silica was washed with 2.5 L of chloroform. The chloroform filtrate was reduced in vacuo to about 1 L, washed in a separatory funnel with 3×1 L volumes of water followed by one 3×1 L volume of brine to remove traces of succinimide, then dried with magnesium sulfate and vacuum filtered. The chloroform was reduced by rotary evaporation at reflux at 1 atmosphere to 250 mL and cooled at −20° C. for 3 days. The resultant crystals were vacuum filtered, washed with 30 mL of chloroform followed by 50 mL of hexanes, then dried in a vacuum oven at room temperature overnight, providing 8.48 g (54%) 2-bromomethylbenzoic acid as a white crystalline power.

Formation of Compound 27:

Compound 27 was obtained according to Method 2 in Example 3, but by substituting 2-bromomethylbenzoic acid for α-Bromo-p-toluic acid.

Isolation of Compound 27:

816 mg of Compound 27 obtained above was dissolved in 25 mL of 0.1 N HCl and loaded onto a column of 9.5 g MCI-gel prepared in 0.1 N HCl. The column was eluted with 250 mL of 0.1 N HCl, followed by 250 mL of 0.5 N HCl, and 250 mL of 1 N HCl. Fractions having purity greater than 95% were combined and concentrated in vacuo to provide 436 mg (44% yield) of Compound 27 (95% purity).

Formation of Compound 15:

Compound 15 is obtained by passing a solution of Compound 27 through a column containing chloride-form anion-exchange resin, e.g., AMBERLITE IRA-402 (chloride form) strongly-basis anion-exchange resin. The effluent is concentrated in vacuo to provide Compound 15.

6.10 Example 10

Synthesis of Compound 28 and Compound 18

28

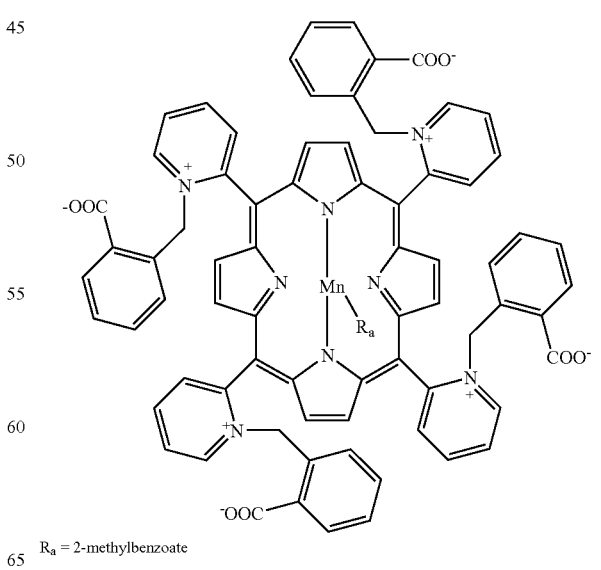

Ra = 2-methylbenzoate

-continued

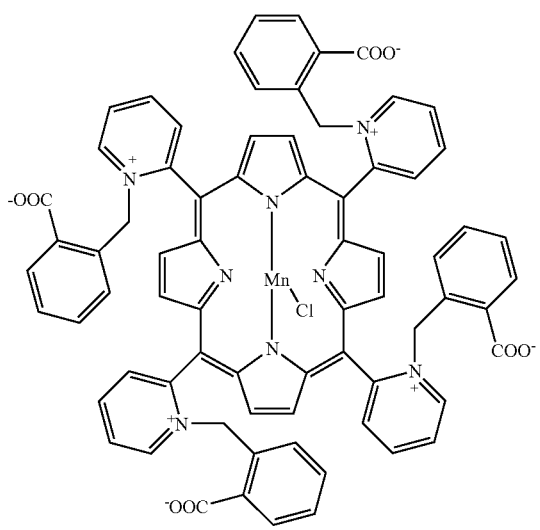

18

Formation of Compound 28:
Compound 28 was obtained according to Examples 12, 3 (Method 2), and 9.

Isolation of Compound 28:
Compound 28 was isolated as set forth in Example 9, but Compound 28 was isolated as its pentachloride salt (n=5) (95% purity).

Formation of Compound 18:
Compound 18 is obtained by passing a solution of Compound 28 through a column containing chloride-form anion-exchange resin, e.g., AMBERLITE IRA-402 (chloride form) strongly-basis anion-exchange resin. The effluent is concentrated in vacuo to provide Compound 18.

6.11 Example 11

Synthesis of Compound 21

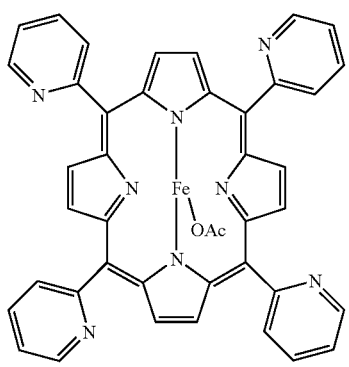

21

Compound 1 (200.0 g) was suspended in 3.2 L of acetic acid and 800 mL of deionized water, and 253.3 g (2.0 eq.) of ferrous ammonium sulfate hexahydrate were added. Air was bubbled slowly through the reaction mixture, which was then refluxed overnight. The hot reaction mixture was transferred to a rotary evaporator, and the solvent was removed in vacuo. The resultant solids were suspended with vigorous stirring for 3 hours in 4 L of 10% ammonium hydroxide, vacuum filtered through #50 paper, and washed four times with 1 L portions of deionized water. The slightly damp solids were stirred for 1 hour in 24 L ethanol and vacuum filtered through 500 g celite in a medium fritted funnel. The filtrate was transferred to the rotary evaporator and concentrated in vacuo. The resultant solids were dried under vacuum at 40° C. for 1 day to provide 164.0 g (68%) of Compound 21 as a deep-purple solid. MS m/z=672 (M$^+$).

6.12 Example 12

Synthesis of Compound 22

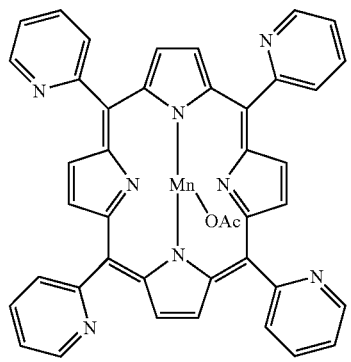

22

Compound 1 (1.00 g) was suspended in 10 mL of acetic acid, and 440 mg (1.01 eq.) of manganese (III) acetate dihydrate was added. The reaction mixture was refluxed overnight, cooled to room temperature, and the solvent was transferred to an evaporator flask and removed in vacuo. Ammonium hydroxide (30% aqueous, 20 mL) was added to the evaporator flask and subsequently removed in vacuo. The resultant solids were twice dissolved in methanol (20 mL), which was subsequently evaporated. The resultant black solid was dissolved in 50 mL of dichloromethane and vacuum filtered through a 3 cm thick bed of celite. The filtrate was concentrated in vacuo and the resultant solid was dried overnight to provide 1.28 g (95%) of Compound 22 as a metallic black solid. MS m/z=671 (M$^+$).

6.13 Example 13

In Vivo Efficacy of an Illustrative Porphyrin Compound Against Radiation-Induced Death Materials and Methods
Balb/c mice used in the following experiments were 8 weeks old, either male or female, and had an average body weight of 24 g. Compound 3A (obtained using the methods outlined in Examples 3 and 4) was administered to the treated animals subcutaneously as a solution in 0.9% normal saline with each individual dose administered in a total solution volume of 0.1 mL. Both treated and control mice were exposed to a 6 Gy dose of ionizing radiation, delivered via a Gammacell 3000 Elan Irradiator (MDS Nordion, Ontario, Canada). To administer the radiation dose, a mouse was placed in a beaker in the irradiation chamber with the sealed radiation source for approximately one minute to deliver a dose of 6 Gy. The animals' "survival ratio" was calculated by dividing the number of surviving mice by the total number of irradiated mice.

Pre-irradiation Treatment of Animals with Compound 3A

Figure 1:
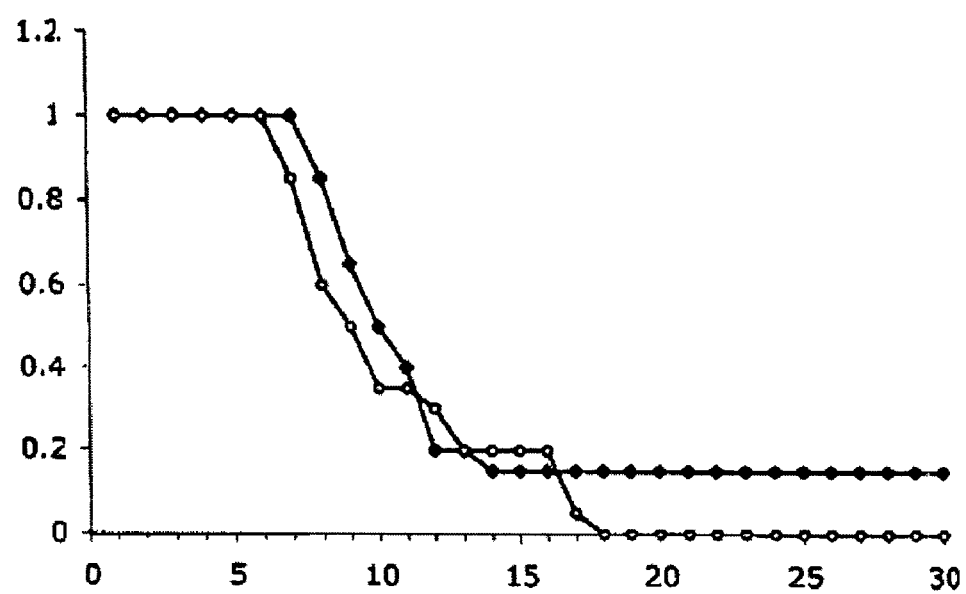

Balb/c mice were divided into two groups of about ten mice each: a control group and a treatment group. Each mouse in the control group was subcutaneously administered 0.1 mL saline two hours prior to irradiation, followed by repeated subcutaneous administrations of 0.1 mL saline every 12 hours afterward. Each mouse in the treatment group was subcutaneously administered a 2 mg/kg dose of Compound 3A (in 0.1 mL saline) two hours prior to irradiation, followed by repeated subcutaneous administrations of a 2 mg/kg dose of Compound 3A (in 0.1 mL saline) every 12 hours afterward. Dosing was continued in each animal in both the control and treatment groups until the death of all of the mice in the control group. Mice in the treatment group survived longer than the control mice with mortality being prevented in 20% of treated animals (FIG. 1). Accordingly, Compound 3A, an illustrative Pyridyl-Substituted Porphyrin Compound, is useful for preventing radiation-induced death in a subject.

Post-irradiation Treatment of Mice with Compound 3A at Dosage of 2 mg/kg

Figure 2:
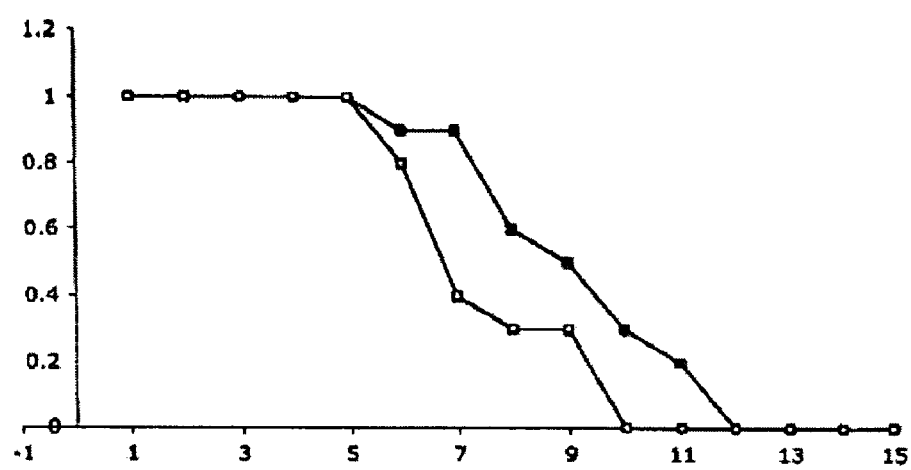

Balb/c mice were divided into two groups of about ten mice each: a control group and a treatment group. Each mouse in the control group was subcutaneously administered 0.1 mL saline ten minutes after irradition, followed by repeated subcutaneous administrations of 0.1 mL saline every 12 hours afterward. Each mouse in the treatment group was subcutaneously administered a 2 mg/kg dose of Compound 3A (in 0.1 mL saline) ten minutes after irradiation, followed by repeated subcutaneous administrations of a 2 mg/kg dose of Compound 3A (in 0.1 mL saline) every 12 hours afterward. Dosing was continued in each animal in both the control and treatment groups until the death of all of the mice in the control group. Mice in the treatment group survived longer than the control mice by approximately 2-4 days (FIG. 2). Accordingly, Compound 3A, an illustrative Pyridyl-Substituted Porphyrin Compound, is useful for increasing a subject's survival time following exposure to radiation.

Post-irradiation Treatment of Mice with Compound 3A at Dosage of 10 mg/kg

Figure 3:
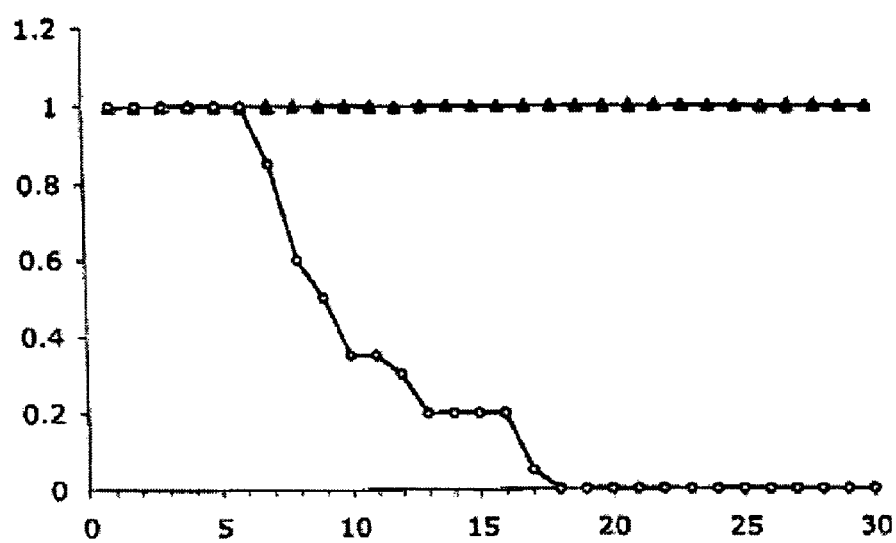

Balb/c mice were divided into two groups of about ten mice each; a control group and a treatment group. Each mouse in the control group was subcutaneously administered 0.1 mL saline ten minutes after irradition, followed by repeated subcutaneous administrations of 0.1 mL saline every 12 hours afterward. Each mouse in the treatment group was subcutaneously administered a 10 mg/kg dose of Compound 3A (in 0.1 mL saline) ten minutes after irradiation, followed by repeated subcutaneous administrations of a 10 mg/kg dose of Compound 3A (in 0.1 mL saline) every 12 hours afterward. Dosing was continued in each animal in both the control and treatment groups until the death of all of the mice in the control group. This dosing regimen prevented radiation-induced death in all of the treated mice, while all mice in the control group died (FIG. 3). Accordingly, Compound 3A, an illustrative Pyridyl-Substituted Porphyrin Compound, is useful for preventing radiation-induced death in a subject.

Figure 4:
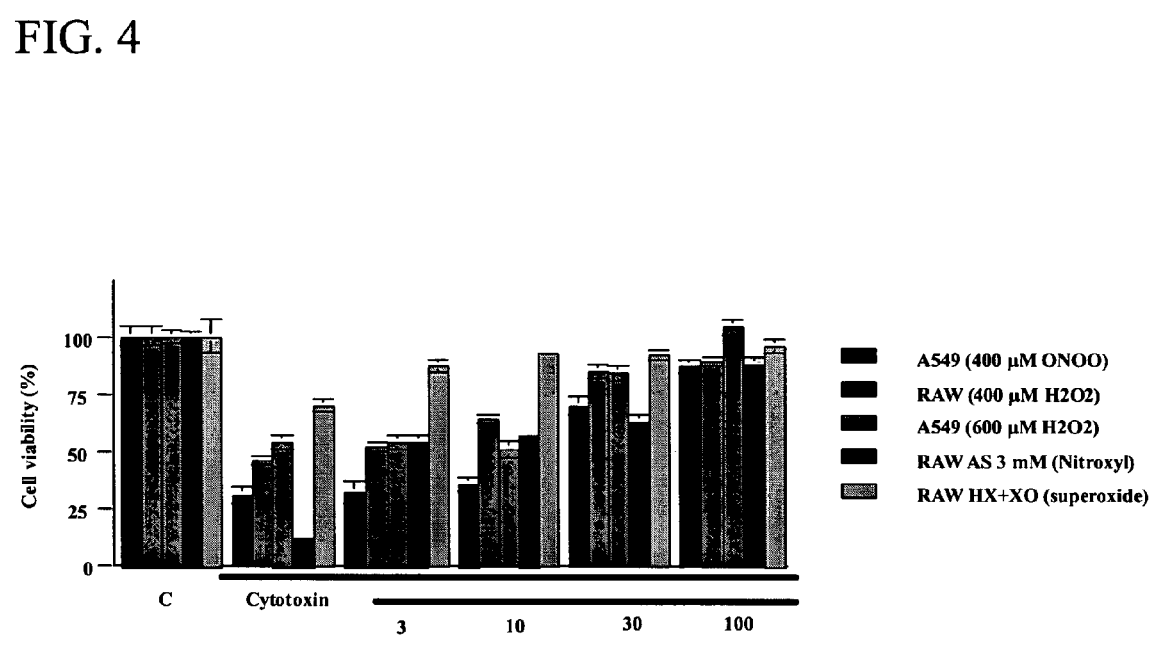

6.14 Effect of an Illustrative Pyridyl-Substituted Porphyrin Compound in Various Disease Models Effect of Compound 3 on Oxidant or Free-radical Damage A549 human epithelial cells and RAW murine macrophages were grown and cultured, then treated with oxidants and free radicals in the presence or absence of varying concentrations of Compound 3 according to the method of C. Szabo et al., *Mol Med.*, October 2002;8(10):571-80. Compound 3 dose-dependently protected against the suppression of cell viability (FIG. 4). Protection is by 3-100 µM of Compound 3.

These data indicate that Compound 3 is useful for protecting cells or tissue from damage from reactive species including oxidants and free radicals, and for treating or preventing various forms of shock, inflammation, reperfusion injury, heart failure, vascular disease, or radiation-induced injury.

Effect of Compound 3 on Myocardial Infarction in Rats

Figure 5:
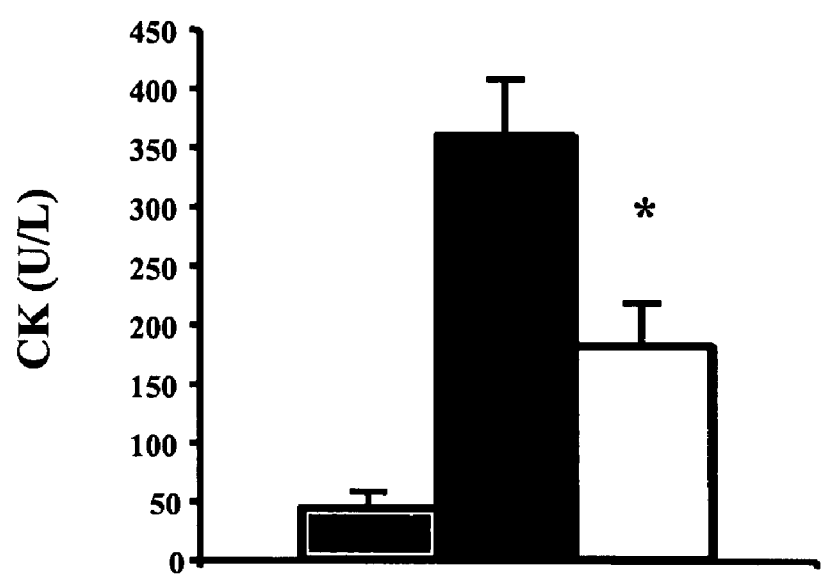
FIG. 5 shows the effect of Compound 3 on creatine kinase (CK) release, a marker of myocardial necrosis induced by left anterior descending coronary artery (LAD) occlusion and reperfusion in the rat. The three bars represent, from left to right, before ischemia, vehicle, and 6 mg/kg Compound 3.
Figure 6:
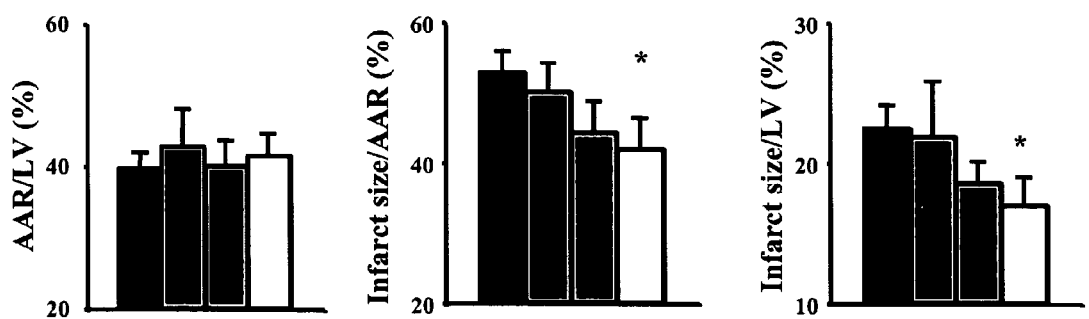
FIG. 6 shows the effect of Compound 3 on myocardial necrosis induced by LAD occlusion and reperfusion in the rat, where AAV represents area at risk and LV represents left ventricular. The four bars in each graph represent, from left to right, vehicle, 1 mg/kg Compound 3, 3 mg/kg Compound 3, and 6 mg/kg Compound 3.
Figure 7:
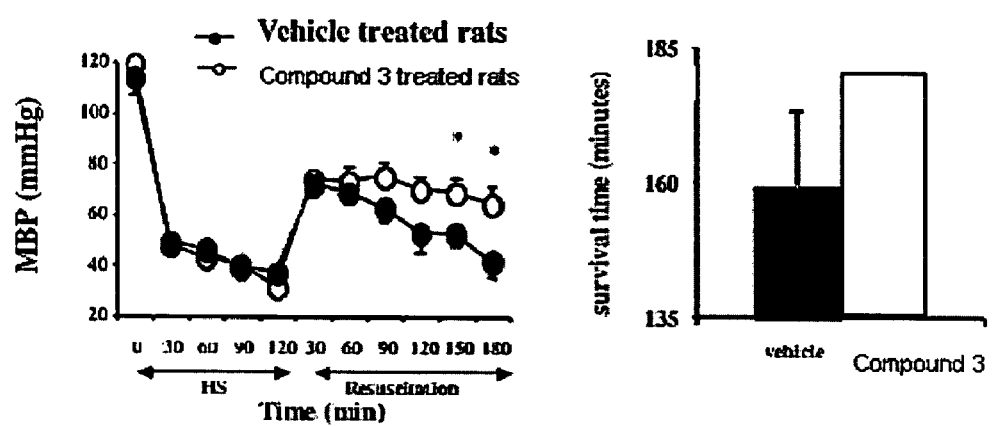
FIG. 7 shows time course of mean blood pressure (BP) and mean survival time in rats subjected to hemorrhagic shock and resuscitation. Values are shown as means±SEM. *, $P<0.05$ vs. vehicle treated rats.

Rats were subjected to myocardial infarction by occlusion and reperfusion of the left anterior descending coronary artery as previously described in C. Y. Xiao et al., *J Pharmacol Exp Ther.*, August 2004;310(2):498-504. Compound 3 was administered at doses of 1, 3, or 6 mg/kg i.v., 5 minutes prior to reperfusion. At 6 mg/kg, Compound 3 reduced plasma levels of creatine kinase (indicative of reduced myocardial necrosis, FIG. 5). 6 mg/kg of Compound 3 produced a significant protective effect. Compound 3 was also effective for reducing infarct size in the rats (FIG. 6).

These data indicate that Compound 3 is useful for protecting myocardial tissues from damage when administered during myocardial reperfusion, and for treating or preventing myocardial infarction and reperfusion injury resulting from cardiopulmonary bypass.

Effect of Compound 3 on Hemorrhagic Shock in Rats

Rats were subjected to 2 hours of hemorrhage, followed by resuscitation as previously described in O. V. Evgenov et al., *Crit Care Med.*, October 2003;31(10):2429-36. Compound 3 was administered at a dose of 6 mg/kg i.v., 5 minutes prior to resuscitation. Compound 3 reduced plasma levels of creatine kinase and ALT (indicative of reduced cell necrosis). Compound 3 was also effective for stabilizing blood pressure and increasing survival rate in the rats (FIGS. 7-10). To obtain the results shown in FIG. 7, rats were bled to reach mean BP of 40 mm Hg. This mean BP was maintained for 2 hours, followed by resuscitation with saline at a volume of 2× the shed blood volume. Rats were then observed for 3 hours, and the survival time was recorded. Compound 3 (6 mg/kg) was administered intravenously before the start of resuscitation. To obtain the results shown in FIG. 8, left intraventricular systolic pressure (LVSP), dP/dt, -dP/dt were monitored continuously for 20 minutes from 40 minutes after resuscitation. Compound 3 (6 mg/kg) was administered intravenously before the start of resuscitation. To obtain the results shown in FIG. 9, blood was taken 1 hour after resuscitation. Compound 3 (6 mg/kg) was administered intravenously before the start of resuscitation. To obtain the results shown in FIG. 10, blood was taken at 1 hour after resuscitation. Compound 3 (6 mg/kg) was administered intravenously before the start of resuscitation.

These data indicate that Compound 3 is useful for protecting a subject from various forms of circulatory shock and for treating or preventing sepsis, systemic inflammatory response syndrome, hemorrhagic shock, cardiogenic shock, and systemic inflammation induced by anticancer therapies, such as IL-2.

Effect of Compound 3 on Heart Failure in Mice

Mice were subjected to heart failure induced by aortic banding as previously described in C. Y. Xiao et al., *J Pharmacol Exp Ther.*, March 2005;312(3):891-8. Compound 3 was administered at a dose of 3 mg/kg/day orally. Compound 3 reduced the degree of myocardial hypertrophy (FIG. 11).

These data indicate that Compound 3 is useful for treating heart failure.

Effect of Compound 3 on Rejection of Hearts During Heterotopic Heart Transplantation Rats were subjected to heterotopic heart transplantation as described previously in H. Jiang et al., *Transplantation*, Jun.

15, 2002;73(11):1808-17. Compound 3 was administered at a dose of 10 mg/kg/day orally. Compound 3 reduced the degree of myocardial hypertrophy (FIG. 12).

These data indicate that Compound 3 is useful for treating or preventing a reperfusion injury resulting from organ transplantation.

Effect of Compound 3 on Vascular Injury

Rats were subjected to balloon-induced vascular injury of the carotid artery as previously described in C. Zhang et al., *Am J Physiol Heart Circ Physiol.*, August 2004;287(2): H659-66. Compound 3 (1 mg/kg bid) prevented the development of endothelial dysfunction after balloon-induced vascular injury and reduced the degree of intimal hypertrophy (FIG. 13 and FIG. 14). As shown in FIG. 13, the injured rat showed an impairment of the endothelium-dependent relaxations, compared to the non-injured (control) side, and Compound 3 treatment completely prevented this loss of the endothelial function (n=4-7).

These data indicate that Compound 3 is useful for reducing the degree of vascular injury associated with cardiovascular diseases including balloon-induced vascular injury, coronary stenting, and atherosclerosis.

Effect of Compound 3 on Diabetes Mellitus

Mice were subjected to multiple low dose streptozocin diabetes as previously described in J. G. Mabley et al., *Br J Pharmacol.*, July 2001;133(6):909-19. Compound 3 (3 or 10 mg/kg/day ip) prevented the development of hyperglycemia and normalized pancreatic insulin content (FIG. 15).

These data indicate that Compound 3 is useful for treating or preventing diabetes or one or more of its complications.

The present invention is not to be limited in scope by the specific embodiments disclosed in the examples, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety.

What is claimed is:

1. A compound having the formula (A)

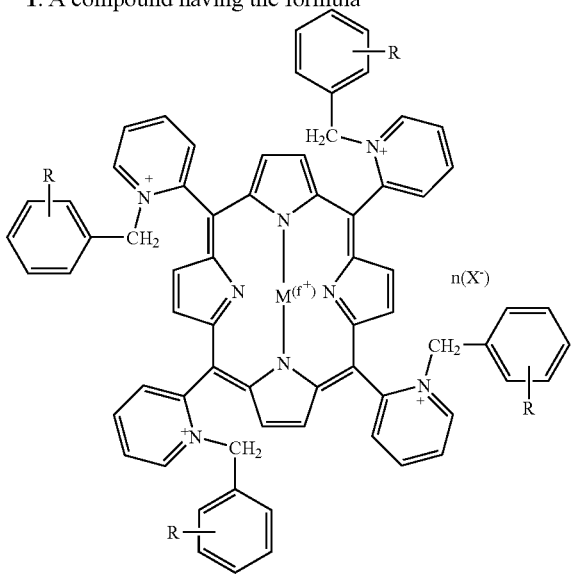

wherein:

M is Fe or Mn;

f is 0 or 1;

each R is independently —C(O)OH or —C(O)O$^-$;

each X$^-$ is independently a negatively-charged counterion; and n=(f)+ (the total number of R groups where R is —C(O)OH).

2. The compound of claim 1, having the formula:

(I)

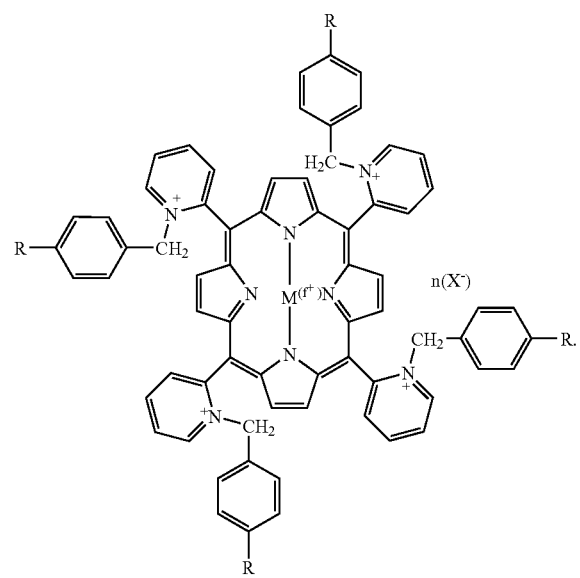

3. The compound of claim 1, having the formula (II)

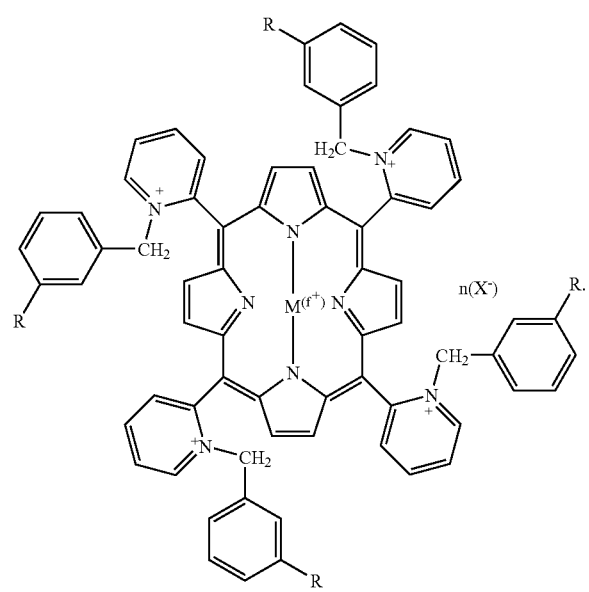

4. The compound of claim 1, having the formula

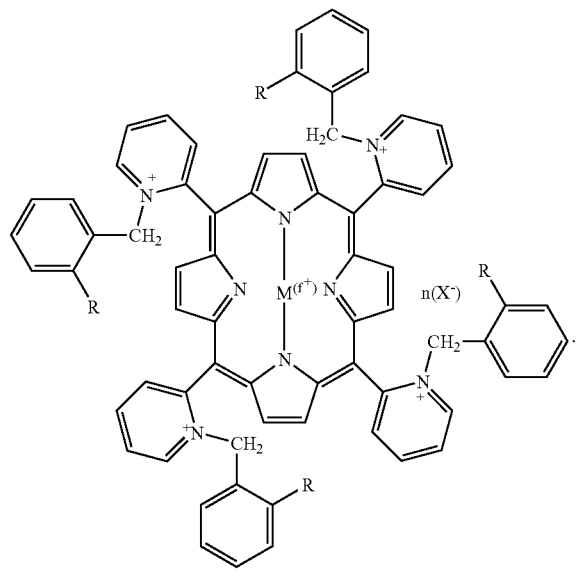

(III)

5. The compound of claim 1, wherein M is Fe.
6. The compound of claim 1, wherein M is Mn.
7. The compound of claim 1, wherein f is 0.
8. The compound of claim 1, wherein f is 1.
9. The compound of claim 1, wherein $X^-$ is $Cl^-$ or $Br^-$.
10. The compound of claim 1, wherein an $X^-$ forms a bond with M.
11. The compound of claim 1, wherein $X^-$ is $F^-$, $Cl^-$, $Br^-$, $I^-$, $HO^-$, or $CH_3C(O)O^-$.
12. The compound of claim 1, wherein each R is —C(O)O$^-$.
13. The compound of claim 1, wherein each R is —C(O)OH.
14. The compound of claim 1, wherein n is 0.
15. The compound of claim 1, wherein n is 5.
16. The compound of claim 5, wherein f is 1, and X is $Cl^-$.
17. The compound of claim 16, wherein each R is —C(O)O$^-$.
18. The compound of claim 1, having the structure

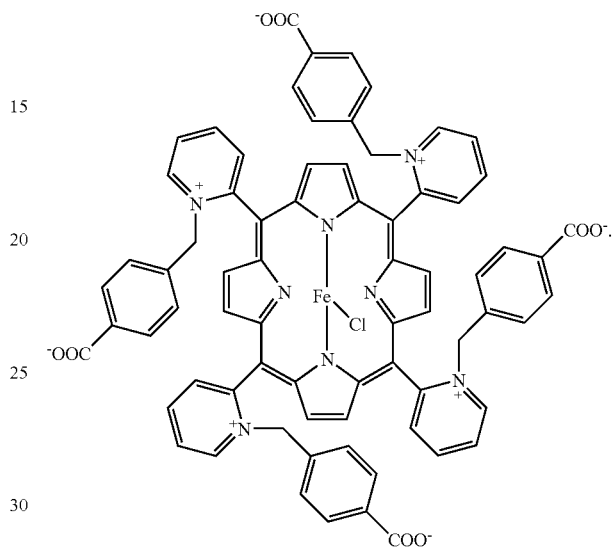

19. A composition comprising an effective amount of the compound of claim 1 and a physiologically acceptable carrier or vehicle.

* * * * *

UNITED STATES PATENT AND TRADEMARK OFFICE
CERTIFICATE OF CORRECTION

PATENT NO. : 7,432,369 B2  Page 1 of 1
APPLICATION NO. : 11/090447
DATED : October 7, 2008
INVENTOR(S) : William Williams et al.

It is certified that error appears in the above-identified patent and that said Letters Patent is hereby corrected as shown below:

Title Page, Item (75) Inventors; replace "Garry Southan, Lynn, MA (US)" with -- Garry Southan, Swampscott, MA (US) --

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,432,369 B2 | Page 1 of 1 |
| APPLICATION NO. | : 11/090447 | |
| DATED | : October 7, 2008 | |
| INVENTOR(S) | : William Williams | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (171) days Delete the phrase "by 171 days" and insert -- by 337 days --

Signed and Sealed this

Fourth Day of May, 2010

David J. Kappos
*Director of the United States Patent and Trademark Office*